United States Patent
Pudil et al.

(10) Patent No.: US 10,583,236 B2
(45) Date of Patent: Mar. 10, 2020

(54) RECIRCULATING DIALYSATE FLUID CIRCUIT FOR BLOOD MEASUREMENT

(71) Applicant: MEDTRONIC, INC., Minneapolis, MN (US)

(72) Inventors: Bryant J. Pudil, Plymouth, MN (US); Thomas E. Meyer, Stillwater, MN (US); David B. Lura, Maple Grove, MN (US); Martin T. Gerber, Maple Grove, MN (US)

(73) Assignee: Medtronic, Inc., Minneapolis, MN (US)

(*) Notice: Subject to any disclaimer, the term of this patent is extended or adjusted under 35 U.S.C. 154(b) by 227 days.

(21) Appl. No.: 15/398,069

(22) Filed: Jan. 4, 2017

(65) Prior Publication Data
US 2017/0112991 A1     Apr. 27, 2017

Related U.S. Application Data

(62) Division of application No. 13/836,538, filed on Mar. 15, 2013, now Pat. No. 9,713,666.
(Continued)

(51) Int. Cl.
*A61M 1/16* (2006.01)
*A61M 1/14* (2006.01)
(Continued)

(52) U.S. Cl.
CPC .......... *A61M 1/1696* (2013.01); *A61M 1/14* (2013.01); *A61M 1/165* (2014.02); *A61M 1/1605* (2014.02); *A61M 1/1613* (2014.02); *A61M 1/1619* (2014.02); *A61M 1/1694* (2013.01); *A61M 1/28* (2013.01); *A61M 1/3406* (2014.02); *A61M 1/3472* (2013.01); *B01D 15/08* (2013.01);
(Continued)

(58) Field of Classification Search
CPC .... A61M 1/14; A61M 1/1605; A61M 1/1613; A61M 1/1619; A61M 1/165; A61M 1/1694; A61M 1/1696; A61M 1/28; A61M 1/3406; A61M 1/3472; A61M 2202/0498; A61M 2205/15; A61M 2205/3317; A61M 2205/3324; A61M 2205/3334; B01D 15/08; B01D 15/362
See application file for complete search history.

(56) References Cited

U.S. PATENT DOCUMENTS 3,840,835 A  10/1974 Kussy
3,850,835 A  11/1974 Marantz
(Continued)

OTHER PUBLICATIONS

Office Action in European Application No. 14746193.3 dated Apr. 19, 2017.
(Continued)

*Primary Examiner* — John Kim
(74) *Attorney, Agent, or Firm* — Kenneth Collier; Roger Hahn

(57) ABSTRACT

A blood based solute monitoring system for measuring at least one blood solute species that has a first recirculation flow path in fluid communication with a dialyzer. The first recirculation flow path is configured to allow a fluid to recirculate through a dialyzer such that the concentration of at least one solute species in the fluid becomes equilibrated to the solute species concentration of the blood in a blood compartment of the dialyzer. The blood solute monitoring system has at least one sensor to measure a fluid characteristic.

6 Claims, 30 Drawing Sheets

Related U.S. Application Data

(60) Provisional application No. 61/760,033, filed on Feb. 1, 2013, provisional application No. 61/750,760, filed on Jan. 9, 2013.

(51) Int. Cl.
*A61M 1/34* (2006.01)
*A61M 1/28* (2006.01)
*B01D 15/08* (2006.01)
*B01D 15/36* (2006.01)

(52) U.S. Cl.
CPC ... *B01D 15/362* (2013.01); *A61M 2202/0498* (2013.01); *A61M 2205/15* (2013.01); *A61M 2205/3317* (2013.01); *A61M 2205/3324* (2013.01); *A61M 2205/3334* (2013.01)

(56) References Cited

U.S. PATENT DOCUMENTS

| | | |
|---|---|---|
| 4,612,122 A | 9/1986 | Ambrus |
| 4,687,582 A | 8/1987 | Dixon |
| 5,080,653 A | 1/1992 | Voss |
| 5,092,886 A | 3/1992 | Dobos-Hardy |
| 5,097,122 A | 3/1992 | Coiman |
| 5,127,404 A | 7/1992 | Wyborny |
| 5,192,132 A | 3/1993 | Pelensky |
| 5,230,702 A | 7/1993 | Lindsay |
| 5,284,470 A | 2/1994 | Beltz |
| 5,302,288 A | 4/1994 | Meidl |
| 5,305,745 A | 4/1994 | Zacouto |
| 5,308,315 A | 5/1994 | Khuri |
| 5,318,750 A | 6/1994 | Lascombes |
| 5,399,157 A | 3/1995 | Goux |
| 5,441,049 A | 8/1995 | Masano |
| 5,442,969 A | 8/1995 | Troutner |
| 5,445,610 A | 8/1995 | Evert |
| 5,468,388 A | 11/1995 | Goddard |
| 5,507,723 A | 4/1996 | Keshaviah |
| 5,662,806 A | 9/1997 | Keshaviah et al. |
| 5,683,432 A | 11/1997 | Goedeke |
| 5,685,988 A | 11/1997 | Malchesky |
| 5,716,400 A | 2/1998 | Davidson |
| 5,744,031 A | 4/1998 | Bene |
| 5,762,782 A | 6/1998 | Kenley |
| 5,770,086 A | 6/1998 | Indriksons |
| 5,849,179 A | 12/1998 | Emerson |
| 5,858,186 A | 1/1999 | Glass |
| 5,938,634 A | 8/1999 | Packard |
| 5,938,938 A | 8/1999 | Bosetto |
| 5,944,684 A | 8/1999 | Roberts |
| 6,036,858 A | 3/2000 | Carlsson |
| 6,048,732 A | 4/2000 | Anslyn |
| 6,052,622 A | 4/2000 | Holmstrom |
| 6,058,331 A | 5/2000 | King |
| 6,114,176 A | 9/2000 | Edgson et al. |
| 6,126,831 A | 10/2000 | Goldau |
| 6,171,480 B1 | 1/2001 | Lee |
| 6,230,059 B1 | 5/2001 | Duffin |
| 6,248,093 B1 | 6/2001 | Moberg |
| 6,254,567 B1 | 7/2001 | Treu |
| 6,321,101 B1 | 11/2001 | Holmstrom |
| 6,362,591 B1 | 3/2002 | Moberg |
| 6,363,279 B1 | 3/2002 | Ben-Haim |
| 6,390,969 B1 | 5/2002 | Bolling et al. |
| 6,521,184 B1 | 2/2003 | Edgson et al. |
| 6,554,798 B1 | 4/2003 | Mann |
| 6,555,986 B2 | 4/2003 | Moberg |
| 6,565,525 B1 | 5/2003 | Burbank et al. |
| 6,572,769 B2 | 6/2003 | Rajan |
| 6,579,460 B1 | 6/2003 | Willis |
| 6,585,675 B1 | 7/2003 | O'Mahony et al. |
| 6,589,229 B1 | 7/2003 | Connelly |
| 6,593,747 B2 | 7/2003 | Puskas |
| 6,596,234 B1 | 7/2003 | Schnell et al. |
| 6,602,399 B1 | 8/2003 | Fromherz |
| 6,627,164 B1 | 9/2003 | Wong |
| 6,666,840 B1 | 12/2003 | Falkvall et al. |
| 6,676,608 B1 | 1/2004 | Keren |
| 6,695,807 B2 | 2/2004 | Bell et al. |
| 6,711,439 B1 | 3/2004 | Bradley |
| 6,719,745 B1 | 4/2004 | Taylor |
| 6,773,412 B2 | 8/2004 | O'Mahony et al. |
| 6,814,724 B2 | 11/2004 | Taylor |
| 6,818,196 B2 | 11/2004 | Wong |
| 6,861,266 B1 | 3/2005 | Sternby |
| 6,878,258 B2 | 4/2005 | Hughes |
| 6,878,283 B2 | 4/2005 | Thompson |
| 6,878,285 B2 | 4/2005 | Hughes |
| 6,890,315 B1 | 5/2005 | Levin |
| 6,923,782 B2 | 8/2005 | O'Mahony et al. |
| 6,960,179 B2 | 11/2005 | Gura |
| 7,029,456 B2 | 4/2006 | Ware et al. |
| 7,033,498 B2 | 4/2006 | Wong |
| 7,077,819 B1 | 7/2006 | Goldau |
| 7,097,630 B2 | 8/2006 | Gotch |
| 7,101,519 B2 | 9/2006 | Wong |
| 7,128,750 B1 | 10/2006 | Stergiopulos |
| 7,153,693 B2 | 12/2006 | Tajiri |
| 7,208,092 B2 | 4/2007 | Micheli |
| 7,241,272 B2 | 7/2007 | Karoor |
| 7,309,323 B2 | 12/2007 | Gura |
| 8,449,487 B2 | 5/2013 | Hovland et al. |
| 8,480,607 B2 | 7/2013 | Davies |
| 8,499,780 B2 | 8/2013 | Wilt |
| 8,518,260 B2 | 8/2013 | Raimann |
| 8,535,525 B2 | 9/2013 | Heyes |
| 8,597,227 B2 | 12/2013 | Childers |
| 8,647,506 B2 | 2/2014 | Wong |
| 8,696,626 B2 | 4/2014 | Kirsch |
| 8,733,559 B2 | 5/2014 | Wong |
| 8,764,981 B2 | 7/2014 | Ding |
| 8,777,892 B2 | 7/2014 | Sandford |
| 8,903,492 B2 | 12/2014 | Soykan |
| 9,144,640 B2 | 9/2015 | Pudil |
| 9,254,355 B2 | 2/2016 | Sandford |
| 9,527,015 B2 | 12/2016 | Chau |
| 2001/0007931 A1 | 7/2001 | Blatter |
| 2001/0009756 A1 | 7/2001 | Hei et al. |
| 2002/0027106 A1 | 3/2002 | Smith |
| 2002/0042561 A1 | 4/2002 | Schulman |
| 2002/0062098 A1 | 5/2002 | Cavicchioli et al. |
| 2002/0112609 A1 | 8/2002 | Wong |
| 2002/0117436 A1 | 8/2002 | Rajan |
| 2003/0080059 A1 | 5/2003 | Peterson |
| 2003/0097086 A1 | 5/2003 | Gura |
| 2003/0105435 A1 | 6/2003 | Taylor |
| 2003/0113931 A1 | 6/2003 | Pan |
| 2003/0114787 A1 | 6/2003 | Gura |
| 2003/0138348 A1 | 7/2003 | Bell et al. |
| 2004/0019312 A1 | 1/2004 | Childers |
| 2004/0019320 A1 | 1/2004 | Childers |
| 2004/0030277 A1 | 2/2004 | O'Mahony et al. |
| 2004/0037986 A1 | 2/2004 | Houston et al. |
| 2004/0054315 A1 | 3/2004 | Levin et al. |
| 2004/0082903 A1 | 4/2004 | Micheli |
| 2004/0084358 A1 | 5/2004 | O'Mahony et al. |
| 2004/0099593 A1 | 5/2004 | DePaolis |
| 2004/0147900 A1 | 7/2004 | Polaschegg |
| 2004/0168963 A1 | 9/2004 | King |
| 2004/0215090 A1 | 10/2004 | Erkkila |
| 2004/0257409 A1 | 12/2004 | Cheok |
| 2005/0006296 A1 | 1/2005 | Sullivan |
| 2005/0056592 A1 | 3/2005 | Braunger |
| 2005/0065760 A1 | 3/2005 | Murtfeldt |
| 2005/0101901 A1 | 5/2005 | Gura |
| 2005/0113796 A1 | 5/2005 | Taylor |
| 2005/0126961 A1 | 6/2005 | Bissler |
| 2005/0131332 A1 | 6/2005 | Kelly |
| 2005/0126998 A1 | 7/2005 | Childers |
| 2005/0148923 A1 | 7/2005 | Sternby |
| 2005/0150832 A1 | 7/2005 | Tsukamoto |
| 2005/0230313 A1 | 10/2005 | O'Mahony et al. |
| 2005/0234381 A1 | 10/2005 | Niemetz |

(56) References Cited

U.S. PATENT DOCUMENTS

| | | |
|---|---|---|
| 2005/0274658 A1 | 12/2005 | Rosenbaum |
| 2006/0025661 A1 | 2/2006 | Sweeney |
| 2006/0217771 A1 | 2/2006 | Soykan |
| 2006/0157413 A1 | 7/2006 | Bene |
| 2006/0189926 A1 | 8/2006 | Hall et al. |
| 2006/0195064 A1 | 8/2006 | Plahey |
| 2006/0226079 A1 | 10/2006 | Mori |
| 2006/0241543 A1 | 10/2006 | Gura |
| 2006/0241709 A1 | 10/2006 | Soykan |
| 2006/0264894 A1 | 11/2006 | Moberg |
| 2007/0007208 A1 | 1/2007 | Brugger |
| 2007/0055296 A1 | 3/2007 | Stergiopulos |
| 2007/0066928 A1 | 3/2007 | Lannoy |
| 2007/0138011 A1 | 6/2007 | Hofmann |
| 2007/0175827 A1 | 8/2007 | Wariar |
| 2007/0179431 A1 | 8/2007 | Roberts |
| 2007/0213665 A1 | 9/2007 | Curtin |
| 2007/0215545 A1 | 9/2007 | Bissler |
| 2007/0243113 A1 | 10/2007 | DiLeo |
| 2007/0255250 A1 | 11/2007 | Moberg |
| 2008/0006570 A1 | 1/2008 | Gura |
| 2008/0011664 A1 | 1/2008 | Karoor |
| 2008/0015493 A1 | 1/2008 | Childers et al. |
| 2008/0021337 A1 | 1/2008 | Li |
| 2008/0051696 A1 | 2/2008 | Curtin |
| 2008/0053905 A9 | 3/2008 | Brugger |
| 2008/0067132 A1 | 3/2008 | Ross |
| 2008/0215247 A1 | 9/2008 | Tonelli |
| 2008/0217245 A1 | 9/2008 | Rambod |
| 2008/0292935 A1 | 11/2008 | Roelofs |
| 2009/0020471 A1 | 1/2009 | Tsukamoto |
| 2009/0078636 A1 | 3/2009 | Uchi |
| 2009/0084199 A1 | 4/2009 | Wright |
| 2009/0101552 A1 | 4/2009 | Fulkerson |
| 2009/0101577 A1 | 4/2009 | Fulkerson |
| 2009/0120864 A1 | 5/2009 | Fulkerson |
| 2009/0127193 A1 | 5/2009 | Updyke |
| 2009/0149795 A1 | 6/2009 | O'Mahony et al. |
| 2009/0216045 A1 | 8/2009 | Singh |
| 2009/0266358 A1 | 10/2009 | Sacristan Rock |
| 2009/0275849 A1 | 11/2009 | Stewart |
| 2009/0275883 A1 | 11/2009 | Chapman |
| 2009/0281484 A1 | 11/2009 | Childers |
| 2010/0004588 A1 | 1/2010 | Yeh |
| 2010/0007838 A1 | 1/2010 | Fujimoto |
| 2010/0010429 A1 | 1/2010 | Childers |
| 2010/0018923 A1 | 1/2010 | Rohde et al. |
| 2010/0030151 A1 | 2/2010 | Kirsch |
| 2010/0051529 A1 | 3/2010 | Grant |
| 2010/0051552 A1 | 3/2010 | Rohde |
| 2010/0076364 A1 | 3/2010 | O'Mahony |
| 2010/0078381 A1 | 4/2010 | Merchant |
| 2010/0084330 A1 | 4/2010 | Wong |
| 2010/0094158 A1 | 4/2010 | Solem |
| 2010/0100027 A1 | 4/2010 | Schilthuizen |
| 2010/0101195 A1 | 4/2010 | Clements |
| 2010/0102190 A1 | 4/2010 | Zhu et al. |
| 2010/0114001 A1 | 5/2010 | O'Mahony |
| 2010/0114012 A1 | 5/2010 | Sandford |
| 2010/0137693 A1 | 6/2010 | Porras |
| 2010/0168546 A1 | 7/2010 | Kamath |
| 2010/0168641 A1 | 7/2010 | O'Mahony |
| 2010/0217181 A1 | 8/2010 | Roberts et al. |
| 2010/0224492 A1 | 9/2010 | Ding et al. |
| 2010/0234795 A1 | 9/2010 | Wallenas |
| 2010/0241045 A1 | 9/2010 | Kelly |
| 2010/0252490 A1 | 10/2010 | Fulkerson |
| 2010/0312174 A1 | 12/2010 | Hoffman |
| 2010/0314314 A1 | 12/2010 | Ding |
| 2010/0326911 A1 | 12/2010 | Rosenbaum |
| 2011/0009798 A1 | 1/2011 | Kelly |
| 2011/0048949 A1 | 3/2011 | Ding et al. |
| 2011/0066043 A1 | 3/2011 | Banet |
| 2011/0077574 A1 | 3/2011 | Sigg |
| 2011/0079558 A1 | 4/2011 | Raimann |
| 2011/0087187 A1 | 4/2011 | Beck |
| 2011/0130666 A1 | 6/2011 | Dong |
| 2011/0163034 A1 | 7/2011 | Castellarnau |
| 2011/0171713 A1 | 7/2011 | Bluchel |
| 2011/0184340 A1 | 7/2011 | Tan |
| 2011/0220562 A1 | 9/2011 | Beiriger |
| 2011/0247973 A1 | 10/2011 | Sargand |
| 2011/0272352 A1 | 11/2011 | Braig |
| 2011/0297593 A1 | 12/2011 | Kelly |
| 2011/0315611 A1 | 12/2011 | Fulkerson |
| 2011/0315632 A1 | 12/2011 | Freije |
| 2012/0016228 A1 | 1/2012 | Kroh |
| 2012/0018377 A1 | 1/2012 | Tsukamoto |
| 2012/0083729 A1 | 4/2012 | Childers |
| 2012/0085707 A1 | 4/2012 | Beiriger |
| 2012/0092025 A1 | 4/2012 | Volker |
| 2012/0115248 A1 | 5/2012 | Ansyln |
| 2012/0220528 A1 | 8/2012 | VanAntwerp |
| 2012/0248017 A1 | 10/2012 | Beiriger |
| 2012/0258545 A1 | 10/2012 | Ash |
| 2012/0258546 A1 | 10/2012 | Marran |
| 2012/0273415 A1 | 11/2012 | Gerber |
| 2012/0273420 A1 | 11/2012 | Gerber |
| 2012/0277546 A1 | 11/2012 | Soykan |
| 2012/0277552 A1 | 11/2012 | Gerber |
| 2012/0277604 A1 | 11/2012 | Gerber |
| 2012/0277650 A1 | 11/2012 | Gerber |
| 2012/0277655 A1 | 11/2012 | Gerber |
| 2012/0277722 A1 | 11/2012 | Gerber |
| 2013/0006128 A1 | 1/2013 | Olde et al. |
| 2013/0018095 A1 | 1/2013 | Vath |
| 2013/0019179 A1 | 1/2013 | Zhao |
| 2013/0020237 A1 | 1/2013 | Wilt et al. |
| 2013/0023812 A1 | 1/2013 | Hasegawa et al. |
| 2013/0025357 A1 | 1/2013 | Noack et al. |
| 2013/0027214 A1 | 1/2013 | Eng |
| 2013/0028809 A1 | 1/2013 | Barton |
| 2013/0030347 A1 | 1/2013 | Sugioka |
| 2013/0030348 A1 | 1/2013 | Lauer |
| 2013/0037142 A1 | 2/2013 | Farrell |
| 2013/0037465 A1 | 2/2013 | Heyes |
| 2013/0056418 A1 | 3/2013 | Kopperschmidt et al. |
| 2013/0072895 A1 | 3/2013 | Kreischer et al. |
| 2013/0075314 A1 | 3/2013 | Nikolic |
| 2013/0087210 A1 | 4/2013 | Brandl et al. |
| 2013/0110028 A1 | 5/2013 | Bachmann et al. |
| 2013/0199998 A1 | 8/2013 | Kelly |
| 2013/0213890 A1 | 8/2013 | Kelly |
| 2013/0213891 A1 | 8/2013 | Karoor |
| 2013/0228516 A1 | 9/2013 | Jonsson |
| 2013/0274642 A1 | 10/2013 | Soykan |
| 2013/0324915 A1 | 12/2013 | (Krensky)Britton |
| 2013/0330208 A1 | 12/2013 | Ly |
| 2013/0331774 A1 | 12/2013 | Farrell |
| 2014/0001112 A1 | 1/2014 | Karoor |
| 2014/0018728 A1 | 1/2014 | Plahey |
| 2014/0042092 A1 | 2/2014 | Akonur |
| 2014/0065950 A1 | 3/2014 | Mendelsohn |
| 2014/0088442 A1 | 3/2014 | Soykan |
| 2014/0110340 A1 | 4/2014 | White |
| 2014/0110341 A1 | 4/2014 | White |
| 2014/0138294 A1 | 5/2014 | Fulkerson |
| 2014/0158538 A1 | 6/2014 | Collier |
| 2014/0158588 A1 | 6/2014 | Pudil |
| 2014/0190876 A1 | 7/2014 | Meyer |

OTHER PUBLICATIONS

Office Action in European Application No. 14746415.0 dated Apr. 19, 2017.

U.S. Appl. No. 61/760,033, dated Feb. 1, 2013, Medtronic.

U.S. Appl. No. 14/637,606_OA Office Action dated Jul. 13, 2017 in U.S. Appl. No. 14/637,606.

U.S. Appl. No. 14/645,394_OA.

[NPL105] Brynda, et. al., The detection of toman 2-microglcbuiin by grating coupler immunosensor with three dimensional antibody networks. Biosensors & Bioelectronics, 1999, 363-368, 14(4).

(56) References Cited

OTHER PUBLICATIONS

[NPL111] Zhong, et. al., Miniature urea sensor based on H(+)-ion sensitive field effect transistor and its application in clinical analysis, Chin. J. Biotechnol., 1992, 57-65. 8(1).
[NPL119] PCT/US2012/034331, International Search Report and Written Opinion dated Jul. 9, 2012.
[NPL121] Roberts M, The regenerative dialysis (REDY) sorbent system. Nephrology, 1998, 275-278:4.
[NPL138] U.S. Appl. No. 61/480,544 dated Apr. 29, 2011.
[NPL139] U.S. Appl. No. 61/480,541 dated Apr. 29, 2011.
[NPL142] Hemametrics, Crit-Line Hematocrit Accuracy, 2003, 1-5, vol. 1, Tech Note No. 11 (Rev. D).
[NPL144] Weissman, S., et al., Hydroxyurea-induced hepatitis in human immunodeficiency virus-positive patients. Clin. Infec. Dis, (Jul. 29, 1999): 223-224.
[NPL146] PCT/US2012/034334, International Search Report, dated Jul. 6, 2012.
[NPL147] PCT/US2012/034335, International Search Report, dated Sep. 5, 2012.
[NPL148] PCT/US/2012/034327, International Search Report, dated Aug. 13, 2013.
[NPL163] U.S. Appl. No. 61/526,209 dated Aug. 22, 2011.
[NPL169] Wang, Fundamentals of intrathoracic impedance monitoring in heart failure, Am. J. Cardiology, 2007, 3G-10G: Suppl.
[NPL16] PCT/US2014/067650 International Search Report Written Opinion dated Mar. 9, 2015.
[NPL176] Bleyer, et. al., Sudden and cardiac death rated in hemodialysis patients, Kidney International. 1999, 1553-1559: 55.
[NPL187] PCT/US2012/034333, International Preliminary Report on Patentability, dated Oct. 29, 2013.
[NPL188] PCT/US2012/034333, International Search Report, dated Aug. 29, 2012.
[NPL197] PCT/US2012/034330, International Preliminary Report on Patentability, dated Oct. 29, 2013.
[NPL1] PCT/US2014/065950 International Search Report and Written Opinion dated Feb. 24, 2015.
[NPL205] Culleton, BF et al. Effect of Frequent Nocturnal Hemodialysis vs. Conventional Hemodialysis on Left Ventricular Mass and Quality of Life. 2007 Journal of the American Medical Association 298 (11), 1291-1299.
[NPL217] U.S. Appl. No. 13/757,722, filed Feb. 1, 2013.
[NPL218] U.S. Appl. No. 13/757,794, filed Feb. 2, 2012.
[NPL219] U.S. Appl. No. 13/791,755, filed Mar. 8, 2013.
[NPL21] U.S. Appl. No. 13/424,479 dated Nov. 1, 2012.
[NPL220] U.S. Appl. No. 13/757,792, filed Feb. 2, 2013.
[NPL222] U.S. Appl. No. 13/757,794, filed Feb. 2, 2013.
[NPL227] U.S. Appl. No. 13/837,287, filed Mar. 15, 2013.
[NPL22] U.S. Appl. No. 13/424,429 dated Nov. 1, 2012.
[NPL230] Redfield, et. al, Restoration of renal response to atria! natriuretic factor in experimental low-output heat failure, Am. J. Physiol., Oct. 1, 1989, R917-923:257. no.
[NPL231] Rogoza, et. al., Validation of A&D UA-767 device for the self-measurement of blood pressure, Blood Pressure Monitoring, 2000, 227-231, 5(4).
[NPL234] Lima, et. al., An electrochemical sensor based on nanostructure hollsndite-type manganese oxide for detection of potassium ion, Sensors, Aug. 24, 2009, 6613-8625, 9.
[NPL235] Maclean, et, al., Effects of hindlimb contraction on pressor and muscle interstitial metabolite responses in the cat, J. App. Physiol., 1998, 1583-1592, 85(4).
[NPL237] U.S. Appl. No. 13/757,693, dated Feb. 1, 2013.
[NPL23] U.S. Appl. No. 13/424,525, filed Mar. 20, 2012.
[NPL240] U.S. Appl. No. 13/836,973, filed Mar. 15, 2013.
[NPL241] U.S. Appl. No. 14/259,655, filed Apr. 23, 2014.
[NPL242] U.S. Appl. No. 14/259,589, filed Apr. 23, 2014.
[NPL243] U.S. Appl. No. 13/757,693, filed Jan. 4, 2013.
[NPL244] U.S. Appl. No. 13/836,079, filed Mar. 15, 2013.
[NPL245] U.S. Appl. No. 14/240,129, filed Aug. 22, 2013.
[NPL246] PCT/US2014/014346 International Search Report and Written Opinion dated May 23, 2014.
[NPL247] U.S. Appl. No. 13/835,735, filed Mar. 15, 2013.
[NPL248] PCT/US2014/014345 International Search Report and Written Opinion, dated May 2014.
[NPL250] U.S. Appl. No. 13/835,735 IDS, filed Jun. 13, 2013.
[NPL264] PCT/US2014/014357 International Search Report and Written Opinion dated May 19, 2014.
[NPL268] Ronco et al. 2008, Cardiorenal Syndrome, Journal American College Cardiology, 52:1527-1539, Abstract.
[NPL26] Overgaard, et. al., Activity-induced recovery of excitability in K+-depressed rat soleus muscle, Am. J. P 280: R48-R55, Jan. 1, 2001.
[NPL27] Overgaard. et. al., Relations between excitability and contractility in rate soleusmuscle: role of the NA+-K+ pump and NA+-K-S gradients. Journal of Physiology, 1999, 215-225, 518(1).
[NPL2] PCT/US2015/032492 International Search Report dated Nov. 19, 2015.
[NPL306] Coast, et al. 1990, An approach to Cardiac Arrhythmia analysis Using Hidden Markov Models, IEEE Transactions on Biomedical Engineering. 1990, 37(9):826-835.
[NPL310] U.S. Appl. No. 61/480,532 dated Apr. 29, 2011.
[NPL317] U.S. Appl. No. 61/480,530 dated Apr. 29, 2011.
[NPL318] U.S. Appl. No. 61/480,528 dated Apr. 29, 2011.
[NPL32] Secemsky, et. al, High prevalence of cardiac autonomic dysfunction and T-wave alternans in dialysis patients. Heart Rhythm, Apr. 2011, 592-598 : vol. 8, No. 4.
[NPL35] Wei, et. al., Fullerene-cryptand coated piezoelectric crystal urea sensor based on urease, Analytica Chimica Acta, 2001,77-85:437.
[NPL376] Gambro AK 96 Dialysis Machine Operators Manual, Dec. 2012. p. 1-140.
[NPL376] Gambro AK 96 Dialysis Machine Operators Manual, Dec. 2012. p. 141-280.
[NPL376] Gambro AK 96 Dialysis Machine Operators Manual, Dec. 2012. p. 281-420.
[NPL376] Gambro AK 96 Dialysis Machine Operators Manual, Dec. 2012. p. 421-534.
[NPL37] U.S. Appl. No. 13/368,225 dated Feb. 7, 2012..
[NPL383] Leifer et al., A Study on the Temperature Variation of Rise Velocity for Large Clean Bubbles, J. Atmospheric & Oceanic Tech., vol. 17, pp. 1392-1402, Oct. 2000.
[NPL384] Talaia, Terminal Velocity of a Bubble Rise in a Liquid Column, World Acad. of Sci., Engineering & Tech., vol. 28, pp. 264-268, Published Jan. 1, 2007.
[NPL386] The FHN Trial Group. In-Center. Hemodialysis Six Times per Week versus Three Times per Week, New England Journal of Medicine, 2010 Abstract.
[NPL387] Gotch FA, Sargent JA A mechanistic analysis of the National Cooperative Dialysis Study (NCDS). Kidney int. 1985: 28:526-34.
[NPL388] Daugirdas JT. Second generation logarithmic estimates of single-pool variable volume Kt/V and analysis of error. J Am Soc Nephrol, 1993: 4:1205-13.
[NPL389] Steil et al. Intl Journ Artif Organs, 1993, In Vivo Verification of an Automatic Noninvasive System for Real Time Kt Evaluation, Asaio J., 1993, 39:M348-52.
[NPL39] PCT/US2012/034332, International Search Report, dated Jul. 5, 2012.
[NPL3] PCT/US2015/019901 International Search Report and Written Opinion dated Jun. 5, 2015.
[NPL46] Siegenthaler, et al., Pulmonary fluid status monitoring with intrathoracic impedance, Journal of Clinical Monitoring and Computing, 24:449-451, published Jan. 12, 2011.
[NPL47] U.S. Appl. No. 61/480,544 dated Apr. 29, 2011.
[NPL494] John Wm Agar: Review: Understanding sorbent dialysis systems, Nephrology, vol. 15, No. 4, Jun. 1, 2010, pp. 406-411.
[NPL499] EP. App. 14746193.3 Search Report dated Oct. 19, 2016.
[NPL4] PCT/US2015/016270 International Search Report and Written Opinion dated Jun. 5, 2015.
[NPL519] Office Action in U.S. Appl. No. 13/586,824 dated Dec. 21, 2015.
[NPL520] Office Action in U.S. Appl. No. 13/586,824 dated Jun. 4, 2015.

(56) References Cited

OTHER PUBLICATIONS

[NPL532] Eureopean Search Report for App. No. EP14745643 dated Oct. 6, 2016.
[NPL534] Office Action in U.S. Appl. No. 13/586,824 dated Dec. 21, 2015.
[NPL548] PCT/US15/18587 International Preliminary Report on Patentability dated Jun. 6, 2016.
[NPL550] European Search Opinion for App. No. EP12826180 dated Mar. 19, 2015.
[NPL551] European Search Opinion for App. No. EP12826180 dated Jan. 18, 2016.
[NPL552] Khanna, Ramesh, R.T. Krediet, and Karl D. Nolph. Nolph and Gokals Textbook of Peritoneal Dialysis New York: Springer 2009. Print.
[NPL553] Ruperez et al., Comparison of a tubular pulsatile pump and a volumetric pump for continuous venovenous renal replacement therapy in a pediatric animal model, 51 ASAIO J. 372, 372-375 (2005).
[NPL554] St. Peter et al., Liver and kidney preservation by perfusion, 359 The Lancet 604, 606(2002).
[NPL555] Dasselaar et al., Measurement of relative blood volume changes during hemodialysis: merits and limitations, 20 Nephrol Dial Transpl. 2043, 2043-2044 (2005).
[NPL556] Ralph T. Yang, Adsorbents: Fundamentals and Applications 109 (2003).
[NPL557] Henny H. Billett, Hemoglobin and Hematocrit, in Clinical Methods: The History, Physical, and Laboratory Examinations 719(HK Walker, WD Hall, & JW Hurst ed., 1990).
[NPL558] Office Action in U.S. Appl. No. 13/565,733 dated Jan. 11, 2016.
[NPL559] Office Action in U.S. Appl. No. 13/565,733 dated Jun. 11, 2015.
[NPL55] U.S. Appl. No. 13/424,454, filed Mar. 20, 2012.
[NPL560] Office Action in U.S. Appl. No. 13/586,824 dated Jun. 4, 2015.
[NPL561] Office Action in U.S. Appl. No. 13/757,792 dated Jun. 2, 2016.
[NPL562] Office Action U.S. Appl. No. 13/757,796 dated Apr. 13, 2015.
[NPL563] Office Action in U.S. Appl. No. 13/757,796 dated Dec. 21, 2015.
[NPL564] Office Action U.S. Appl. No. 13/835,735 dated Oct. 13, 2015.
[NPL565] Office Action in U.S. Appl. No. 13/836,079 dated Apr. 17, 2015.
[NPL566] Office Action in U.S. Appl. No. 13/836,079 dated Jun. 30, 2016.
[NPL569] Office Action in U.S. Appl. No. 13/791,755 dated Mar. 16, 2016.
[NPL570] Office Action in U.S. Appl. No. 13/791,755 dated Aug. 9, 2016.
[NPL571] Office Action in U.S. Appl. No. 13/835,735 dated Jun. 16, 2016.
[NPL572] Office Action in U.S. Appl. No. 13/836,079 dated Nov. 6, 2015.
[NPL57] U.S. Appl. No. 13/424,467, filed Mar. 20, 2012.
[NPL584] Office Action in App. No. AU 2015280604 dated Apr. 8, 2016.
[NPL586] International Search Report from International Application No. PCT/US2014/014347 dated May 9, 2014.
[NPL590] PCT/US2016/030319 Written Opinion dated Jul. 27, 2016.
[NPL591] PCT/US2016/030320 Written Opinion dated Jul. 27, 2016.
[NPL596] PCT/US2012/014347, International Search Report dated May 9, 2014.
[NPL5] PCT/US2015/016273 International Search Report and Written Opinion dated Jun. 9, 2015.
[NPL601] Wester et al., A regenerable postassium and phosphate sorbent system to enhance dialysis efficacy and device portability: an in vitro study Nephrol Dial Transplant (2013) 28: 2364-2371 Jul. 3, 2013.
[NPL602] Office Action in App. No. JP 2016-515476 dated Dec. 26, 2016.
[NPL603] Japanese Patent Publication No. S50-70281A.
[NPL605] PCT/US2015/032494 Written Opinion dated Nov. 19, 2015.
[NPL606] PCT/US2015/032494 International Search Report dated Nov. 19, 2015.
[NPL607] PCT/US2015/019901 International Preliminary Report on Patentability dated May 27, 2016.
[NPL608] PCT/US2015/019901 Written Opinion dated May 27, 2016.
[NPL609] PCT/US2015/019901 Written Opinion dated Jun. 5, 2015.
[NPL610] PCT/US2015/019901 International Search Report dated Jun. 5, 2015.
[NPL611] PCT/US2015/032485 International Preliminary Report on Patentability dated May 11, 2016.
[NPL612] PCT/US2015/032485 International Preliminary Report on Patentability dated May 11, 2016.
[NPL614] PCT/US2016/030304 International Search Report dated Jul. 27, 2016.
[NPL615] PCT/US2016/030304 Written Opinion dated Jul. 27, 2016.
[NPL616] PCT/US2016/030312 Written Opinion dated Jul. 28, 2016.
[NPL617] PCT/US2016/030312 International Search Report dated Jul. 28, 2016.
[NPL618] PCT/US2016/030319 International Search Report dated Jul. 27, 2016.
[NPL619] PCT/US2016/030319 Written Opinion dated Jul. 27, 2016.
[NPL620] PCT/US2016/030320 Written Opinion dated Jul. 28, 2016.
[NPL621] PCT/US2016/030320 International Search Report dated Jul. 28, 2016.
[NPL622] PCT/US2015/032485 Written Opinion dated Oct. 16, 2015.
[NPL626] PCT/US2015/032485 International Search Report and Written Opinion dated Oct. 16, 2015.
[NPL62] U.S. Appl. No. 13/424,533.
[NPL634] PCT/US2016/030320 International Preliminary Report on Patentability, dated Apr. 20, 2017.
[NPL655] European Search Report from European Application No. EP 14746193.3 dated Oct. 19, 2016.
[NPL656] European Search Report from European Application No. EP 14746193.3 dated Jun. 8, 2016.
[NPL657] PCT/US2014/014345 Written Opinion dated Jun. 24, 2015.
[NPL658] PCT/US2014/014345 International Search Report and Written Opinion dated May 30, 2014.
[NPL659] Office Action in European Application No. 14746428.03 dated Feb. 8, 2017.
[NPL660] European Search Report in European Application No. 14746428.03 dated Aug. 25, 2016.
[NPL661] PCT/US2014/014346 Writtent Opinion dated Apr. 10, 2015.
[NPL662] PCT/US2014/014346 International Search Report and Writtent Opinion dated May 23, 2014.
[NPL663] EP 14746415.0 European Search Report dated Aug. 22, 2016.
[NPL664] Office Action in European Application No. EP 14746415.0 dated Apr. 19, 2017.
[NPL67] U.S. Appl. No. 13/424,490, filed Mar. 20, 2012.
[NPL681] PCT/US2015/020047 International Search Report and Written Opinion dated Jun. 29, 2015.
[NPL682] PCT/US2015/020047 International Preliminary Report on Patentability dated Jun. 30, 2016.
[NPL684] PCT/US2015/020044 Written Opinion dated Jun. 21, 2016.

(56) References Cited

OTHER PUBLICATIONS

[NPL685] PCT/US2015/020044 International Preliminary Report on Patentability dated Nov. 4, 2016.
[NPL686] PCT/US2015/020044 International Search Report dated Jun. 30, 2015.
[NPL688] US2015/019881 Written Opinion dated Jun. 16, 2016.
[NPL689] US2015/0199881 Written Opinion dated May 9, 2016 in PCT/US2015/019881.
[NPL68] U.S. Appl. No. 13/424,517, filed Mar. 20, 2012.
[NPL690] US2015/019881 International Search Report and Written Opinion dated Jun. 29, 2015 in PCT/US2015/019881.
[NPL692] PCT/US2014/065950 International Preliminary Report on Patentability dated Oct. 28, 2015.
[NPL696] PCT/US2015/032485 Written Opinion dated May 9, 2016.
[NPL6] PCT/US2015/032492 Written Opinion dated Nov. 19, 2015.
[NPL720] PCT/US2015/019901 International Search Report and Written Opinion dated Jun. 5, 2015.
[NPL721] PCT/US2015/019901 International Preliminary Report on Patentability dated May 27, 2016.
[NPL722] PCT/US2015/032494 International Preliminary Report on Patentablity dated Dec. 27, 2016.
[NPL730] Office Action for Chinese Application No. 201580009562.5 dated Jul. 3, 2017.
[NPL734] International Preliminary Report on Patentability for Application No. PCT/US2015/032492 dated Jun. 30, 2017.
[NPL737] International Preliminary Report on Patentability for Application No. PCT/US2015/016273 dated Feb. 19, 2016.
[NPL747] European Search Report for App. No. 15751391.2 dated Aug. 4, 2017.
[NPL755] European Search Report and supplementary Search Report for App. No. 14865374.4 dated Jun. 12, 2017.
[NPL756] European Search Report and Supplemental Search Report in European Application No. 14865374.4 dated Jun. 12, 2017.
[NPL7] PCT/US2015/020046 International Search Report and Written Opinion dated Jun. 29, 2015.
[NPL81] U.S. Appl. No. 61/480,539 dated Apr. 29, 2011.
[NPL84] U.S. Appl. No. 61/480,535 dated Apr. 29, 2011.
[NPL8] PCT/US2015/020044 International Search Report Written Opinion dated Jun. 30, 2015.
[NPL] European Search Report App 14865374.4, dated Jun. 12, 2017.

RECIRCULATING DIALYSATE FLUID CIRCUIT FOR BLOOD MEASUREMENT

CROSS-REFERENCE

This application claims the priority of U.S. Provisional Application No. 61/760,033 filed on Feb. 1, 2013 and U.S. Provisional Application No. 61/750,760 filed on Jan. 9, 2013, the entire contents thereof are incorporated herein by reference.

FIELD OF THE INVENTION

The invention relates to systems and methods for utilizing a sorbent cartridge and quantifying chemistry changes that occur as dialysate passes through material layers of the cartridge as a means to determine solute concentrations in the solution flowing through the cartridge. The systems and methods of the invention can be used in systems and methods for managing blood urea and quantifying urea clearance during dialysis therapy including, but not limited to, hemodialysis, hemodiafiltration, hemofiltration, and peritoneal dialysis.

BACKGROUND

Chronic Kidney Disease (CKD), also known as chronic renal disease, may be a sudden or progressive loss in renal function. As the disease severity progresses, a patient with severe renal failure develops many symptoms that, if left untreated, eventually result in death. The most severe stage of CKD is End Stage Renal Disease (ESRD). ESRD, also referred to as kidney failure or renal failure, is the medical condition wherein a person's kidneys fail to sufficiently remove toxins, waste products, and excess fluid, and to maintain proper electrolyte levels.

Urea is among the many waste products often found in the blood of an ESRD patient's blood in an unhealthy amount. Urea is not very toxic by itself, but its level represents the levels of many other waste products that build up in the blood when the kidneys fail.

Kidney dialysis is a medical procedure that is performed to aid or replace some of the kidney functions in severe renal failure. Hemodialysis, hemofiltration, hemodiafiltration, and peritoneal dialysis are all replacement therapies for patients who have lost most or all of their kidney function. In connection with a hemodialysis session, waste products such as urea are removed from the blood. Hemodialysis artificially separates the waste products and excess water from the patient's blood by diffusion and ultra-filtration, by circulating through a machine with a special filter that removes wastes and extra fluids, with the clean blood then being returned to the body.

Urea is generally accepted to be the best marker for evaluating the level of uremic toxins. Dialysis procedures are therefore often aimed at reduction of urea in the blood stream. Currently, urea measurements in most dialysis clinics are often done infrequently to lower cost. Turnaround time for these samples can be quite long, and often the patient must be recalled for further dialysis if the percentage reduction of urea in the blood is not sufficient. In the absence of a blood check, the use of time of dialysis alone as a measure of completion, especially if hemodialysis is not carried out long enough, can clearly lead to morbidity and mortality.

Moreover, these measurements often require blood sampling before and after treatment and require time consuming chemical analyses. As a consequence, the measurements cannot be used to determine actual urea clearance efficiency or control the extent and duration of an individual patient's dialysis session.

Management of patients undergoing continuous hemodialysis requires a means of determining the adequacy of their treatment, which is typically reported as the unitless quantity Kt/V, where K is dialyzer clearance, t is time of hemodialysis treatment and V is body fluid volume. A simple measurement of blood urea nitrogen (BUN) is generally an insufficient indication of adequacy of dialysis since, for instance, a low BUN can reflect inadequate nutrition rather than sufficient urea removal by dialysis. In a patient with little or no urine output, the protein catabolic rate (PCR) (g/day) is equal to the sum of the dialysis and stool losses of urea, protein, and amino acids. PCR is roughly equal to protein intake when a patient is in a steady state with a relatively constant pre-dialysis BUN. As such, BUN is largely reflective of patient diet rather than the adequacy of dialysis treatment. Monitoring the patient's symptoms alone is also insufficient, since the combination of dialysis plus with other treatments (e.g. erythropoietin to increase red blood cell count) can eliminate most uremic symptoms although the patient may be underdialyzed.

In accessing the adequacy of hemodialysis, blood tests for hemodialysis patients are typically, however, performed only on a monthly basis. Many factors can compromise the effective clearance achieved during a dialysis session. These factors include blood access recirculation, access connection errors, dialyzer clotting, blood flow errors, dialysis session interruptions, and dialyzer variability. However, monthly or periodic testing is inadequate to determine if effective clearance is achieved by any individual dialysis treatment.

A number of approaches have been described in the art for determining BUN and urea content:

U.S. Pat. No. 3,776,819 describes a method to measure BUN by means of a cation sensitive electrode having a urease layer on its surface. The electrode configured in this manner is then placed in a solution containing urea and a millivolt signal is analyzed to determine the urea concentration.

U.S. Pat. No. 5,308,315 describes an enzymatic urease sensor to measure the urea concentration electrometrically in spent dialysate, combined together with measured flows for arterial blood, venous blood, and dialysate to calculate the arterial BUN by a method based on principle of solute mass balance across the dialyzer. The enzymatic urease sensing method used is a modified Nova 12 chemistry analyzer for Nova Biomedical, Waltham, Mass. The arterial BUN measurements are used to measure URR for purposes of determining when the prescribed dialysis dose is completed.

U.S. Pat. No. 5,849,179 describes a method for obtaining a pre-dialysis BUN measurement by equilibrating the dialysate urea concentration to the blood urea concentration before the start of dialysis. The method of equilibration is to start blood flow through the primed dialyzer while preventing flow of the dialysate until the concentrations between blood and dialysate are equilibrated. The equilibrated sample is then analyzed by passing the sample to an ammonium sensitive electrode covered by a cap containing urease.

U.S. Pat. No. 5,662,806 further describes how a continuing sequence of non-equilibrated samples of spent dialysate with urea concentration measured by this sensor system can be used to monitor the progress of a dialysis dose with quantification of Kt/V and URR.

U.S. Pat. No. 5,858,186 describes an electrochemical sensor that quantifies urea concentration by measuring pH changes in an aqueous environment that occur when enzyme catalyzed hydrolysis of urea occurs.

European Patent 0 614 081 B1 describes a method and apparatus that passes ultrafiltrate from a hemofilter through a urease containing reactor. Inductive type conductivity sensors are positioned in the fluid circuit before the urease reactor inlet and after the urease reactor outlet. The difference in conductivity is used to determine the urea concentration of the ultrafiltrate. The BUN is determined in this method because ultrafiltrate has the same urea concentration as the arterial blood.

U.S. Pat. Nos. 6,114,176 and 6,521,184 describe a method and apparatus to measure urea in spent dialysate by measuring the conductivity of the dialysate before and after passing through a column containing urease. The method discloses infusion of carbon dioxide into the dialysate as a buffer to maximize conversion of urea to the ionic byproducts ammonium and bicarbonate so that the maximum conductivity signal is obtained. Use of single or dual conductivity sensors is discussed.

U.S. Pat. No. 6,666,840 describes a method and apparatus for determining waste products in dialysate, including urea by means of measuring absorption of ultraviolet light.

U.S. Pat. No. 7,326,576 describes the use of Raman spectroscopy to measure urea concentration in blood through the tubing of the extracorporeal circuit.

US patent application publication 2011/0163034 describes measurement of urea in spent dialysate by means of UV sensing or other urea sensors and methods to determine the K/V slope and assess whether the dialysis therapy session is proceeding according to the prescribed dialysis dose.

There is a need for determining BUN and urea content for hemodialysis patients more frequently than on a monthly basis. There is also a need for assessing the adequacy of dialysis during treatment. There is a need for improved methods and devices for assessing and monitoring the effective clearance achieved during a given dialysis session. There is a need for obtaining a measured clearance of waste products during each dialysis session and determining if delivery of less or more than the prescribed dialysis clearance has occurred.

In particular, there is a need to provide a blood based solute monitoring system for measuring at least one blood solute species, wherein a first recirculation flow path can be in fluid communication with a dialyzer and can be configured to allow a fluid to recirculate through a dialyzer such that the concentration of at least one solute species in the fluid becomes equilibrated to the solute species concentration of the blood in a blood compartment of the dialyzer.

SUMMARY OF THE INVENTION

The present invention relates to a blood based solute monitoring system for measuring at least one blood solute species. In any embodiment, a first recirculation flow path can be in fluid communication with a dialyzer. In any embodiment, the first recirculation flow path can be configured to allow a fluid to recirculate through a dialyzer such that the concentration of at least one solute species in the fluid becomes equilibrated to the solute species concentration of the blood in a blood compartment of the dialyzer. In any embodiment, the blood solute monitoring system can have at least one sensor to measure a fluid characteristic.

In any embodiment, the blood based solute monitoring system can have a second flow path that passes the fluid through the dialyzer. In any embodiment, the at least one solute species in the fluid does not become equilibrated with the solute species in the blood in the blood compartment of the dialyzer.

In any embodiment, the blood based solute monitoring system can have the at least one solute species in the fluid in the second flow path not being equilibrated with solute species in the blood in the blood compartment of the dialyzer.

In any embodiment, the blood based solute monitoring system can have the second flow path being a sorbent regenerated dialysate flow path.

In any embodiment, the blood based solute monitoring system can have the second flow path being a controlled compliant flow path.

In any embodiment, the blood based solute monitoring system can have the first recirculation flow path having a small volume and a control valve for selectively metering fluid in and out of the first recirculation flow path.

In any embodiment, the blood based solute monitoring system can have the first recirculation flow path being in fluid communication with a REDY system.

In any embodiment, the blood based solute monitoring system can have dialysate being recirculated through the sorbent cartridge and not the dialyzer to create a baseline concentration and directed through the dialyzer and a solute concentration profile can be measured and used to determine the solute clearance through the dialyzer.

In any embodiment, the blood based solute monitoring system can have the equilibration time taking less than any one of 10 minutes, 7 minutes, 5 minutes, 3 minutes, 2 minutes, and 1 minute.

In any embodiment, the blood based solute monitoring system can have a control mechanism to decrease equilibration time by increasing dialysate and/or blood flow during fluid flow through the first recirculation flow path.

In any embodiment, the blood based solute monitoring system can have a control mechanism to decrease equilibration time by continuing to perform ultrafiltration during fluid flow through the first recirculation flow path with or without increased rate of fluid flows.

In any embodiment, the blood based solute monitoring system can have the void volume of the components and conduits that make up the first recirculation flow path being less than a volume from the group consisting of 1.0 L, 0.5 L, 0.4 L, 0.3 L, 0.2 L, and 0.1 L.

In any embodiment, the blood based solute monitoring system can have a valve. In any embodiment, operation of the valve can determine whether the fluid flows through the first recirculation flow path or the second flow path.

In any embodiment, the blood based solute monitoring system can have a pump. In any embodiment, operation of the pump can cause the fluid to flow through the first recirculation flow path.

In any embodiment, the blood based solute monitoring system can have the sensor being an ion selective sensor.

In any embodiment, the blood based solute monitoring system can have at least two sensors to measure a fluid characteristic.

In any embodiment, the blood based solute monitoring system can have the sensor being a conductivity sensor.

In any embodiment, the blood based solute monitoring system can have the sensor being any one of a potassium sensor, a bicarbonate sensor, or an ammonia sensor.

In any embodiment, the blood based solute monitoring system can have the conductivity sensor being used to determine when equilibration with the blood has been achieved.

In any embodiment, the blood based solute monitoring system can have the conductivity sensor being used as a measure of the sodium concentration of the blood.

In any embodiment, the blood based solute monitoring system can have the sodium concentration being measured at the start of a therapy session to determine a pre-dialysis blood sodium concentration of a subject and being used to profile the dialysate sodium concentration during the therapy session.

In any embodiment, the blood based solute monitoring system can have the sensor being a pH sensor.

In any embodiment, the blood based solute monitoring system can have the blood solute monitoring system being in fluid communication with a controlled compliant flow path.

In any embodiment, the blood based solute monitoring system can have a sorbent system for regenerating the dialysate and returning the dialysate to the dialyzer.

In any embodiment, the blood based solute monitoring system can have fluid flowing in the first recirculation flow path through the dialyzer that does not pass through one or more material layer of a sorbent system.

In any embodiment, the blood based solute monitoring system can have at least one material layer contains one or more selected from a urease-containing material, alumina, zirconium phosphate, zirconium oxide, a divalent cation, activated carbon, and mixtures thereof.

In any embodiment, the blood based solute monitoring system can have at least one material layer containing urease present in the first recirculation flow path.

In any embodiment, the blood based solute monitoring system can have dialysate flowing in the first recirculation flow path contacting a defined sequence of material layers within the sorbent system.

In any embodiment, the blood based solute monitoring system can have an electrolyte bolus injector.

In any embodiment, the blood based solute monitoring system can have the electrolyte bolus injector being located in the first recirculation flow path at a position downstream from a dialysate outlet of the dialyzer and upstream of the sorbent system, and the system monitoring fluid at one or more positions in the first recirculation flow path selected from the group consisting of: a first position downstream from the dialyzer outlet and downstream from the electrolyte bolus injector where the fluid has not contacted any material layer of the sorbent system; a second position where the fluid has contacted a urease-containing material layer; a third position where the fluid has contacted an additional material layer that is not a urease-containing material layer; and a fourth position in fluid communication with dialysate eluted from an outlet of the dialyzer and positioned upstream from the electrolyte bolus injector.

In any embodiment, the blood based solute monitoring system can have the fluid at the second position having only contacted the urease-containing material layer.

In any embodiment, the blood based solute monitoring system can measure the conductivity of the fluid at one or more positions within the controlled compliant flow path.

In any embodiment, the blood based solute monitoring system can measure the conductivity of the fluid at one or more positions within the sorbent system.

In any embodiment, the blood based solute monitoring system can have one or more selected from the group consisting of: an acid feed supplied to the controlled compliant flow path; a bicarbonate feed; and a water feed.

In any embodiment, the blood based solute monitoring system can have a sorbent system having a plurality of material layers within the sorbent system. In any embodiment, dialysate exiting a dialyzer can be conveyed through the sorbent system.

In any embodiment, the blood based solute monitoring system can have a controlled compliant flow path circulating the dialysate between a dialyzer and the sorbent system.

In any embodiment, the blood based solute monitoring system can form part of a hemodialysis or hemodiafiltration system.

The present invention also relates to a method for measuring the solute concentration of at least one blood solute species, including the steps of: switching fluid flow in a fluid therapy device from a first flow path to a dialyzer recirculation flow path; equilibrating the dialysate with a blood side of the dialyzer; and measuring the solute concentration in the dialysate that has been equilibrated with the blood side of the dialyzer.

In any embodiment, the method for measuring the solute concentration of at least one blood solute species can include the step of switching flow from the dialyzer recirculation flow path to the first flow path for continuing with a fluid therapy.

The present invention also relates to a method for measuring BUN, including the steps of: switching fluid flow in a fluid therapy device having a sorbent system and a dialyzer from a first flow path to a sorbent bypass fluid path; recirculating the dialysate through the dialyzer; and equilibrating the dialysate with blood in the blood side of the dialyzer.

In any embodiment, the method for measuring BUN can include switching the fluid flow from the sorbent bypass fluid path to a non-bypass path; and measuring an ammonium ion concentration of the equilibrated dialysate after contacting urease in the sorbent system.

In any embodiment, the method for measuring BUN can include the step of continuing with dialysis.

The present invention also relates to a method for measuring the solute concentration of at least one blood solute species, including the steps of: switching fluid flow in a fluid therapy device having a sorbent system and a dialyzer from a first flow path to a sorbent bypass fluid path; recirculating the dialysate through the dialyzer; and equilibrating the dialysate with blood in the blood side of the dialyzer; and measuring the conductivity of the equilibrated dialysate before the dialysate has contacted a predetermined layer or sequence of layers to provide a first conductivity value; and switching the fluid flow from the sorbent bypass fluid path to cause the equilibrated dialysate to contact a predetermined material layer or sequence of material layers in the sorbent system; and measuring the conductivity of the equilibrated dialysate after it has contacted the predetermined material layer or sequence of material layers to provide a second conductivity value.

In any embodiment, the method for measuring the solute concentration of at least one blood solute species can include the step of determining a solute concentration according to a predetermined relationship between conductivity and solute concentration.

In any embodiment, the method for measuring the solute concentration of at least one blood solute species can have the solute concentration being based upon a difference of the second conductivity value and the first conductivity value.

In any embodiment, the method for measuring the solute concentration of at least one blood solute species can include the step of continuing with dialysis.

In any embodiment, the method for measuring the solute concentration of at least one blood solute species can have the contacted material containing urease, the blood solute concentration measured being BUN and the sensed fluid characteristic being the conductivity of the fluid.

In any embodiment, the method for measuring the solute concentration of at least one blood solute species can include measuring the conductivity of a second non-equilibrated dialysate before contacting a urease containing material to provide a third conductivity value; measuring the conductivity of the second non-equilibrated dialysate after contacting a urease containing material to provide a fourth value; and determining the effective urea clearance of the dialyzer from the first, second, third and fourth conductivity values.

In any embodiment, the method for measuring the solute concentration of at least one blood solute species can include one or more determinations of the effective clearance of a dialyzer. In any embodiment, these determinations can be used to monitor the performance of a therapy session.

The present invention also relates to a method to measure BUN, including measuring a first conductivity value of a dialysate flowing from an outlet of a dialyzer not having contacted a urease containing material layer of a sorbent system; measuring a second conductivity value of the dialysate flowing from the outlet of a dialyzer after the fluid has contacted a urease containing material layer of a sorbent system; intermittently providing an electrolyte bolus or diluent to the dialysate flow path and measuring a bolus conductivity of the dialysate passing to the dialyzer to provide a third conductivity value; measuring a bolus conductivity of the dialysate passing from the dialyzer to provide a fourth conductivity value; and determining the effective clearance of the dialyzer from the third and fourth conductivity values.

In any embodiment, the method to measure BUN can include determining the BUN from the effective clearance of the dialyzer from the first and second conductivity values.

In any embodiment, the method to measure BUN can include determining the blood concentration of a solute from the said effective clearance of the dialyzer from the first and second equilibrated conductivity values.

In any embodiment, the method of the blood based solute monitoring system for measuring at least one blood solute species can include the step of determining the urea content of the dialysate flowing from the dialyzer based at least in part on the difference in conductivity between at least a first and second sensor values.

In any embodiment, the method of the blood based solute monitoring system for measuring at least one blood solute species can include the dialysate contacting the plurality of materials in a sequential order.

In any embodiment, the method to measure BUN can have the one or more sorbent cartridges having an ion exchange resin selective for calcium ions and magnesium ions and releasing hydrogen ions in exchange.

In any embodiment, the method to measure BUN can include a third conductivity value of the equilibrated dialysate that has contacted an additional material layer is not contacted by the fluid of the first or second conductivity value; and determining the blood solute concentration of at least a second blood solute from either the second and third conductivity values or the first and third conductivity values.

In any embodiment, the method to measure BUN can include calculating one of the selected measures BUN (blood urea nitrogen), URR (urea reduction ratio), Kt/V, eKt/V (equilibrated Kt/V), and PCR (protein catabolic rate), wherein k stands for dialyzer clearance rate, t stands for dialysis time, and V stands for volume of distribution of urea.

In any embodiment, URR can be determined by calculating a first BUN prior to dialysis and a second BUN post dialysis.

In any embodiment, Kt/V, eKt/V and PCR can each be determined based on a difference between the first and second conductivity values.

In any embodiment, the method to measure BUN can include determining the level or concentration of a solute selected from the group of K, Mg, Ca, pH, bicarbonate, and glucose.

Figure 1:
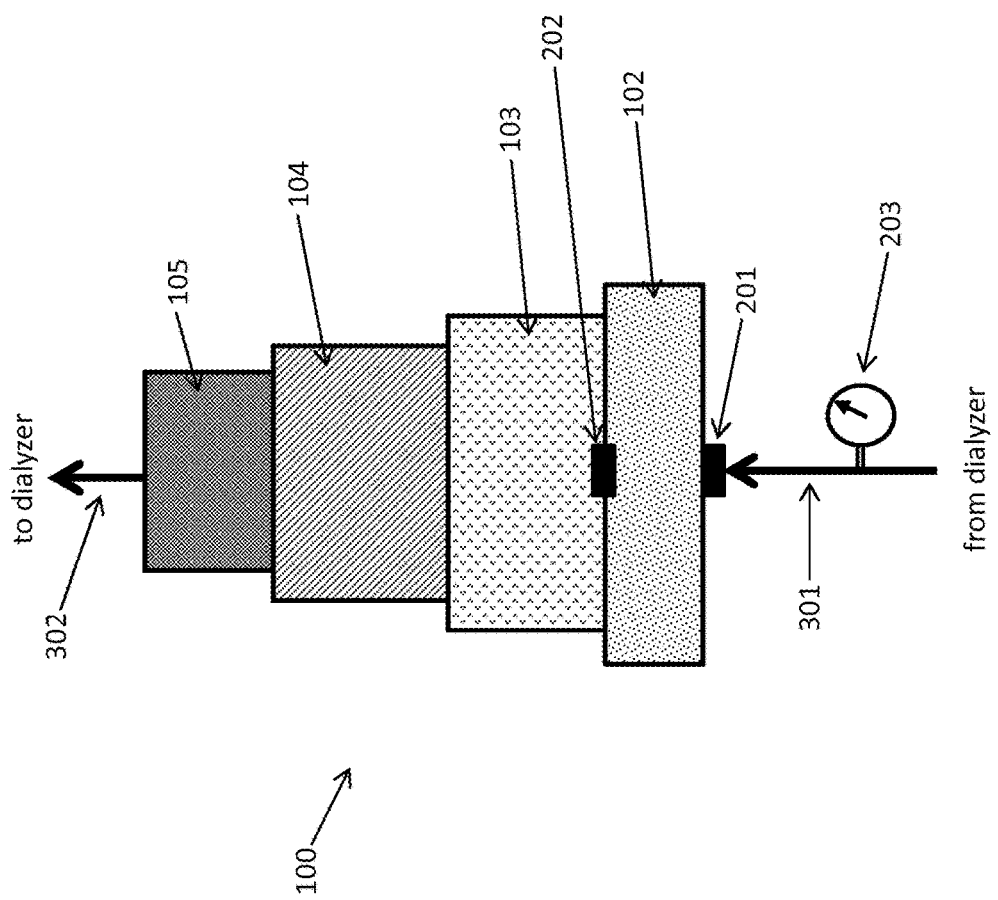
FIG. 1 shows a dialysate regeneration cartridge operating in accordance with certain embodiments.

Like reference numbering between FIGS. represents like features and elements.

DETAILED DESCRIPTION

Definitions

Unless defined otherwise, all technical and scientific terms used herein generally have the same meaning as commonly understood by one of ordinary skill in the relevant art. The definitions provided herein should not be rigidly construed without taking into account the context and other ascribed meanings provided, or by their use, in other parts of the specification, claims, and drawings.

The articles "a" and "an" are used herein to refer to one or to more than one (i.e., to at least one) of the grammatical object of the article. By way of example, "an element" means one element or more than one element.

The term "substantially" refers to an extent of similarity between any two given values that is at least 75 percent, 80 percent, 85 percent, 90 percent, 95 percent, or 99.9 percent, the given values optionally including values in weight, height, length, area, temperature, angle dimensions, among others.

The term "acid or base equivalents" refers to an equivalent acid or base donating or accepting an equal number of moles of hydrogen or hydronium ions per mole of the acid to which the equivalent acid is being equated, or mole of hydroxide ions to which the equivalent base is being equated.

The term "cation infusate pump" historically known as an "acid concentrate pump" in dialysis systems refers to a pump that serves the function to move or control the flow of a fluid to and/or from a reservoir having a substance that contains at least one cation species, such as calcium, magnesium and potassium ions. In the present invention, the historically used term of "acid concentrate pump" is used.

The term "acid feed" refers a state of fluid communication that enables an acid solution to be obtained from an acid source and connected or feed into a receiving source or flow path.

An "acid" can be either an Arrhenius acid, a Brønsted-Lowry acid, or a Lewis acid. The Arrhenius acids are substances or fluids which increase the concentration of hydronium ions ($H_3O^+$) in solution. The Brønsted-Lowry acid is a substance which can act as a proton donor. Lewis acids are electron-pair acceptors.

The term "activated carbon" may refer to a porous carbon material having a surface area greater than 500 $m^2$ per gram. Activated carbon can be capable of absorbing several species including heavy metals such as lead, mercury, arsenic, cadmium, chromium and thallium among others, oxidants such as chlorine and chloramines, fluoride ions, and waste species such as phosphate and certain nitrogen-containing waste species such as creatinine and uric acid.

The terms "administering," "administer," "delivering," "deliver," "introducing," and "introduce" can be used, in context, interchangeably to indicate the introduction of water or a dialysate having an altered concentration of at least one component, including electrolytes and alkali and/or alkali earth ions, to a patient in need thereof, and can further mean the introduction of water, any agent or alkali and/or alkali earth ions to a dialysate or dialysis circuit where such water, agent or alkali and/or alkali earth ion will enter the blood of the patient by diffusion, transversal of a diffusion membrane or other means.

The term "air trap" refers to a structure for separating a gas from a mixture of a gas and a liquid or any other separation means known in the art. An air trap can include a hydrophobic membrane for allowing gases to pass and for preventing the passage of water.

The term "albumin sieving coefficient" can be used to describe the amount of albumin that will cross a membrane.

The terms "ammonia sensing module" and "ammonia detector" refer to a unit that performs all or part of the function to detect a predetermined level of, or measure a concentration of, ammonia and/or ammonium ions in a fluid.

The term "anion exchange membrane" refers to a positively charged membrane, which allows negatively charged ions (anions) to pass through.

The term "anticoagulant" is a substance that prevents or delays the clotting of blood, such as heparin, Fragmin®, and sodium citrate.

The term "atmospheric pressure" refers to the local pressure of air in the environment in proximity to the system at the time that the system is operating.

The term "base concentrate pump" refers to a device that performs work on a fluid solution to cause fluid flow to control the volume transfer of a basic or alkaline solution into a circuit.

The term "base concentrate reservoir" refers to a vessel or container, optionally accessible by a pump that contains a variable amount of a basic or alkaline fluid solution.

The term "base module" refers to a basic unit of an apparatus for hemodialysis, hemodiafiltration, or hemofiltration that incorporates one or more fluid pathways. Exemplary, non-limiting components that can be included in the base module include conduits, valves, pumps, fluid connection ports, sensing devices, a controller and a user interface. The base module can be configured to interface with reusable or disposable modules of the apparatus for hemodialysis, hemodiafiltration, or hemofiltration to form at least one complete fluid circuit, such as a dialysis, cleaning, disinfection, priming or blood rinse back circuit.

A "base" can be either a substance that can accept hydrogen cations (protons) or more generally, donate a pair of valence electrons. A soluble base is referred to as an alkali if it contains and releases hydroxide ions (OH—) quantitatively. The Brønsted-Lowry theory defines bases as proton (hydrogen ion) acceptors, while the more general Lewis theory defines bases as electron pair donors, allowing other Lewis acids than protons to be included. The Arrhenius bases act as hydroxide anions, which is strictly applicable only to alkali.

The term "base feed" refers a state of fluid communication that enables a base solution to be obtained from a base source and connected or feed into a receiving source or flow path.

The term "bicarbonate buffer component" refers to any composition contain bicarbonate ($HCO_3^-$) ion or a conjugate acid of bicarbonate ion in any amount, proportion or pH of the composition. The bicarbonate buffering system is an important buffer system in the acid-base homeostasis of living things, including humans. As a buffer, it tends to maintain a relatively constant plasma pH and counteract any force that would alter it. In this system, carbon dioxide (CO2) combines with water to form carbonic acid ($H_2CO^3$), which in turn rapidly dissociates to form hydrogen ions and bicarbonate ($HCO_3^-$) as shown in the reactions below. The carbon dioxide-carbonic acid equilibrium is catalyzed by the enzyme carbonic anhydrase; the carbonic acid-bicarbonate equilibrium is simple proton dissociation/association and needs no catalyst.

$$CO_2 + H_2O \rightleftharpoons H_2CO_3 \rightleftharpoons HCO_3^- + H^+$$

Any disturbance of the system will be compensated by a shift in the chemical equilibrium according to Le Chatelier's principle. For example, if one attempted to acidify the blood by dumping in an excess of hydrogen ions (acidemia), some of those hydrogen ions will associate with bicarbonate, forming carbonic acid, resulting in a smaller net increase of acidity than otherwise.

The term "bicarbonate buffer concentrate" refers to a bicarbonate ($HCO_3^-$) buffer component composition at a higher concentration than found at normal physiological levels that can be used to for instants to readjusted the pH of the dialysate (see also definition of bicarbonate buffer component relating to its use).

The term "bicarbonate cartridge" refers to a container that can be a stand-alone container or alternatively can be integrally formed with an apparatus for hemodialysis, hemodiafiltration, or hemofiltration. The bicarbonate cartridge can store a source of buffering material, such as sodium bicarbonate, and can be configured to interface with at least one other functional module found in systems for hemodialysis, hemodiafiltration, or hemofiltration. For example, the bicarbonate cartridge can contain at least one fluid pathway and include components such as conduits, valves, filters or fluid connection ports. The bicarbonate cartridge can be disposable or be consumable wherein the cartridge is recharged upon depletion. Specifically, the term "bicarbonate consumables container" refers to an object or apparatus having or holding a material in solid and/or solution form that is a source of bicarbonate, such as sodium bicarbonate, that is depleted during operation of the system. The object or apparatus may be single use, or may be replenished and used multiple times, for example, by refilling the object to replace the consumed material.

The term "bicarbonate feed" refers to fluid solution introduced into part of the dialysis or ultrafiltrate system. For example a "bicarbonate feed" is a conduit that contains a bicarbonate buffer concentrate that is used to readjust the pH of the dialysate.

The term "bidirectional pump" refers to a device configured to perform work on a fluid to cause the fluid to flow alternatively in either of two opposing directions.

A "biocompatible material" is a material that has the ability to interface with living biological tissues with an acceptable host response in any of specific medical systems, methods of treatment or delivery contemplated herein. The biocompatible material can consist of synthetic, natural or modified natural polymers intended to contact or interact with the biological systems during application of any of the inventions contained herein.

The term "bipolar electrodialysis system" refers to an electrochemical separation process in which ions are selectively transferred through a bipolar membrane.

The term "bipolar membrane" refers to a membrane formed by bonding an anion exchange and a cation exchange membrane together wherein the membranes result in the dissociation of water into hydrogen ions. The anion- and cation-exchange membranes can either be bound together physically or chemically such that the bipolar membrane has a thin interface where water diffuses into the membrane from outside aqueous salt solutions.

The term "blood access connection" refers to a junction or aperture through which the blood of a subject is conveyed to or from an extracorporeal circuit. Commonly, the blood access connection is made between a terminal end of a conduit of an extracorporeal circuit and the terminal end of a catheter or fistula needle that is distal to the subject receiving therapy. A subject may have more than one blood access connection when receiving therapy. In the case of two blood access connections they can be referred to as an arterial blood access connection and a venous blood access connection.

The term "blood solute" refers to a substance dissolved, suspended, or present in blood or dialysate.

The term "bolus" refers to an increase (or at times a decrease) of limited duration in an amount or concentration of one or more solutes, for example sodium, glucose and potassium, or a solvent, for example water, such that the concentration of a solution is changed. The term "bolus" includes delivery of solute and/or solvent to the dialysate fluid path such that it is delivered to the blood of a subject via diffusion and/or convection across a dialysis membrane such that the amount or concentration in the subject is increased or decreased. A "bolus" may also be delivered directly to the extracorporeal flow path or the blood of a subject without first passing through the dialysis membrane.

The term "bottled water" refers to water that may be filtered or purified and has been packaged in a container. Bottled water can include water that has been packaged and provided to a consumer as drinking water. The term "breakthrough capacity" refers to the amount of solute a sorbent material can remove until breakthrough occurs. Breakthrough occurs when the concentration of a certain solute exiting a regeneration module becomes non-zero.

The terms "bubble detector", "bubble sensor", "gas detector" and "air detector" refer to a device that can detect the presence of a void, void space, or gas bubble in a liquid.

The term "buffer conduit flow path" refers to a fluid flow path in fluid communication with a stored source of a buffering material, such as bicarbonate.

The term "buffer source" refers to a stored material, such as bicarbonate, acetate or lactate that provides buffering.

The terms "buffer source container" and "buffer source cartridge" refer to objects that have or hold one or more materials, in solid and/or solution form, that are a source of buffering, for example a bicarbonate, a lactate, or acetate; and the object further having at least one port or opening to allow at least a portion of the buffering material to be released from the object during operation of the system.

The term "blood based solute monitoring system" refers to a system for monitoring a substance dissolved or suspended or present in blood or dialysate.

The term "blood rinse back" refers to returning the blood from a dialyzer and/or extracorporeal circuit to a subject, normally at conclusion of a therapy session and prior to disconnecting or removing the subject's blood access connection or connections. The procedure can include conveying a physiologically compatible solution through the extracorporeal circuit to push or flush the blood from the extracorporeal circuit to the subject via the subject's blood access connection or connections.

The terms "bypass circuit" "bypass conduit," "bypass flow path," "bypass conduit flow path" and "bypass" refer to a component or collection of components configured or operable to create an alternate fluid pathway to convey a fluid around one or more other components of a fluid circuit such that at least a portion of the fluid does not contact or pass through the one or more other components. At times the term "shunt" may be used interchangeable with the term "bypass." When any of the above "bypass" terms listed in this paragraph are used in context as being part of a controlled compliant system, then the relevant referenced "bypass" has the proper characteristics as to operate within a controlled compliant system as defined herein.

The term "bypass regulator" refers to a component such as valve that can determine the amount of fluid that can pass through a by-pass portion of a fluid circuit.

The term "capacitive deionization" refers to a process for directly removing salts from solution by applying an electric field between two electrodes.

The term "cartridge" refers to a compartment or collection of compartments that contains at least one material used for operation of the system of the present invention.

The term "cassette" refers to a grouping of components that are arranged together for attachment to, or use with the device, apparatus, or system. One or more components in a cassette can be any combination of single use, disposable, consumable, replaceable, or durable items or materials.

The term "cation exchange membrane" refers to a negatively charged membrane, which allows positively charged ions (cations) to pass. By convention, electrical current flows from the anode to the cathode when a potential is applied to an electrodialysis cell. Negatively charged anions such as chloride ions are drawn towards the anode, and positively charged cations such as sodium ions are drawn towards the cathode.

The term "cation infusate source" refers to a source from which cations can be obtained. Examples of cations include, but are not limited to, calcium, magnesium and potassium. The source can be a solution containing cations or a dry composition that is hydrated by the system. The cation infusate source is not limited to cations and may optionally include other substances to be infused into a dialysate or replacement fluid, non-limiting examples can be glucose, dextrose, acetic acid and citric acid.

The term "cation concentrate reservoir" refers to an object having or holding a substance that is comprised of at least one cation, for example calcium, magnesium, or potassium ions.

The terms "communicate" and "communication" include, but are not limited to, the connection of system electrical elements, either directly or remotely, for data transmission among and between said elements. The terms also include, but are not limited, to the connection of system fluid elements enabling fluid interface among and between said elements.

The terms "conduit", "conduit" or "flow path" refer to a vessel or passageway having a void volume through which a fluid can travel or move. A conduit can have a dimension parallel to the direction of travel of the fluid that is significantly longer than a dimension orthogonal to the direction of travel of the fluid.

The term "central axis" refers to (a) a straight line about which a body or a geometric figure rotates or may be supposed to rotate; (b) a straight line with respect to which a body or figure is symmetrical—called also axis of symmetry; (c) a straight line that bisects at right angles a system of parallel chords of a curve and divides the curve into two symmetrical parts; or (d): one of the reference lines of a coordinate system.

The term "chelating resins" refers to a class of resins that interacts and selectively binds with selected ions and ligands (the process is referred to as chelation). According to IUPAC, the formation or presence of two or more separate coordinate bonds.

The term "chronic kidney disease" (CKD) refers to a condition characterized by the slow loss of kidney function over time. The most common causes of CKD are high blood pressure, diabetes, heart disease, and diseases that cause inflammation in the kidneys. CKD can also be caused by infections or urinary blockages. If CKD progresses, it can lead to end-stage renal disease (ESRD), where the kidneys fail to function at a sufficient level.

The term "citric acid" refers to an organic acid having the chemical formula $C_6H_8O_7$, and may include anhydrous and hydrous forms of the molecule, and aqueous solutions containing the molecule.

The term "cleaning and/or disinfection concentrate" refers to a dry substance, or concentrated solutions containing at least one material for use in cleaning and/or disinfection of an apparatus.

The term "cleaning and/or disinfection solution" refers to a fluid that is used for the purpose of removing, destroying or impairing at least a portion of at least one contaminant. The contaminant may be organic, inorganic or an organism. The fluid may accomplish the purpose by transmission of thermal energy, by chemical means, flow friction or any combination thereof.

The terms "cleaning manifold" and "cleaning and disinfection manifold" refer to an apparatus that has fluid connection ports and one or more fluid pathways, or fluid port jumpers, that, when connected to jumpered ports of a base module, create one or more pathways for fluid to be conveyed between the jumpered ports of the base module. A cleaning manifold may be further comprised of additional elements, for example valves and reservoirs.

The term "container" as used herein is a receptacle that may be flexible or in-flexible for holding fluid or solid, such as for example a spent dialysate fluid, or a sodium chloride or sodium bicarbonate solution or solid.

The terms "common container," "common cartridge," or "common reservoir," and the like refer to an object or apparatus that can hold more than one material; however, the time of holding more than one material may or may not necessarily be at the same time. The material(s) may be in solid and/or solution forms and may be held in separate compartments within the object or apparatus.

The term "common fluid inlet port" refers to an opening or aperture through which all fluid first passes to enter an object, apparatus or assembly.

The term "common fluid outlet port" refers to an opening or aperture through which all fluid passes to exit an object, apparatus or assembly.

The terms "communicate" and "communication" include, but are not limited to, the connection of system electrical elements, either directly or remotely, for data transmission among and between said elements. The terms also include, but are not limited, to the connection of system fluid elements enabling fluid interface among and between said elements.

The terms "component" and "components" refer to a part or element of a larger set or system. As used herein, a component may be an individual element, or it may itself be a grouping of components that are configured as a set, for example, as a cassette or a cleaning and/or disinfection manifold.

The term "comprising" includes, but is not limited to, whatever follows the word "comprising." Thus, use of the term indicates that the listed elements are required or mandatory but that other elements are optional and may or may not be present.

The term "concentrate pump" refers to a device that can perform work on a fluid solution to cause the fluid flow and can actively control the transfer of fluid volume such as an infusate or an acid concentrate, base concentrate, or buffer concentrate into a circuit.

The terms "concentrate flow channel," "concentrate flow loop," "concentrate stream," refer to a fluid line in which ion concentration is increased during electrodialysis.

The terms "conditioning conduit flow path" and "conditioning flow path" refer to a fluid pathway, circuit or flow loop that incorporates a source of a conditioning material, for example a sodium salt or bicarbonate.

The term "conditioning flow path inlet" refers to a location on a conditioning flow path where fluid enters the conditioning flow path.

The term "conditioning flow path outlet" refers to a location on a conditioning flow path where fluid exits the conditioning flow path.

The terms "conductivity meter," "conductivity sensor," "conductivity detector", conductivity electrode or the like, refer, in context, to a device for measuring the electrical conductance of a solution and/or the ion, such as a sodium ion, concentration of a solution. In specific examples, the conductivity sensor, meter, or conductor can be directed to a specific ion such as sodium and be referred to as a "sodium electrode," "sodium sensor," "sodium detector," or "sodium meter."

The term "conductive species" refers to a material's ability to conduct an electric current. Electrolytes are an example of a conductive species in dialysate fluids, such as, but not limited to the presence sodium, potassium, magnesium, phosphate, and chloride ions. A fluid's ability to conduct an electrical current is due in large part to the ions present in the solution. A fluid's ability to conduct an electrical current is due in large part to the ions present in the solution.

The terms "conduit", "circuit", and "flow path" refer to a vessel or passageway having a void volume through which a fluid can travel or move. A conduit can have a dimension parallel to the direction of travel of the fluid that is significantly longer than a dimension orthogonal to the direction of travel of the fluid.

The term "connectable" refers to being able to be joined together for purposes including but not limited to maintaining a position, allowing a flow of fluid, performing a measurement, transmitting power, and transmitting electrical signals. The term "connectable" can refer to being able to be joined together temporarily or permanently.

The term "consisting of" includes and is limited to whatever follows the phrase "consisting of." Thus, the phrase indicates that the limited elements are required or mandatory and that no other elements may be present.

The term "consisting essentially of" includes whatever follows the term "consisting essentially of" and additional elements, structures, acts or features that do not affect the basic operation of the apparatus, structure or method described.

The term "consumables" refers to components that are dissipated, wasted, spent or used up during the performance of any function in the present invention. Examples include a quantity of sodium, bicarbonate, electrolytes, infusates, sorbents, cleaning and disinfecting ingredients, anticoagulants, and components for one or more concentrate solutions.

The terms "consumables cartridge" and "consumables container" refer to an object or apparatus having or holding one or more materials that are depleted during operation of the system. The one or more materials may be in solid and/or solution form and can be in separate compartments of the object or apparatus. The object or apparatus may be single use, or may be replenished and used multiple times, for example, by refilling the object to replace the consumed material.

The terms "contact", "contacted", and "contacting" refers, in context, to (1) a coming together or touching of objects, fluids, or surfaces; (2) the state or condition of touching or of immediate proximity; (3) connection or interaction. For example, in reference to a "dialysate contacting a sorbent material" refers to dialysate that has come together, has touched, or is in immediate proximity to connect or interact with any material or material layer of a sorbent container, system or cartridge.

The term "container" as used herein is a receptacle that may be flexible or inflexible for holding fluid or solid, such as for example a spent dialysate fluid, or a sodium chloride or sodium bicarbonate solution or solid, or the like.

The term "contaminant" refers to an undesirable or unwanted substance or organism that may cause impairment of the health of a subject receiving a treatment or of the operation of the system.

The term "control pump," such as for example an "ultrafiltrate pump," refers to a pump that is operable to pump fluid bi-directionally to actively control the transfer of fluid volume into or out of a compartment or circuit.

The terms "control reservoir," "ultrafiltrate reservoir," "solution reservoir," "therapy solution reservoir," and "waste reservoir", as the case may be, refers, in context, to a vessel or container, optionally accessible by a control pump that contains a variable amount of fluid, including fluid that can be referred to as an ultrafiltrate. These reservoirs can function as a common reservoir to store fluid volume from multiple sources in a system. Other fluids that can be contained by these reservoirs include, for example, water, priming fluids, waste fluids, dialysate, including spent dialysate, and mixtures thereof. In certain embodiments, the reservoirs can be substantially inflexible, or non-flexible. In other embodiments, the reservoirs can be flexible containers such as a polymer bag.

The term "control signals" refers to energy that is provided from one element of a system to another element of a system to convey information from one element to another or to cause an action. For example, a control signal can energize a valve actuator to cause a valve to open or close. In another example a switch on a valve can convey the open or close state of a valve to a controller.

A "control system" consists of combinations of components that act together to maintain a system to a desired set of performance specifications. The control system can use processors, memory and computer components configured to interoperate to maintain the desired performance specifications. It can also include fluid control components, and solute control components as known within the art to maintain the performance specifications.

The terms "control valve" and "valve" refer to a device that can be operated to regulate the flow of fluid through a conduit or flow path by selectively permitting fluid flow, preventing fluid flow, modifying the rate of fluid flow, or selectively guiding a fluid flow to pass from one conduit or flow path to one or more other conduits or flow paths.

The terms "controlled compliant flow path", "controlled compliant dialysate flow path" and "controlled compliant solution flow path" refer to flow paths operating within a controlled compliant system having the characteristic of controlled compliance, or of being controlled compliant as defined herein.

A "controller," "control unit," "processor," or "microprocessor" is a device which monitors and affects the operational conditions of a given system. The operational conditions are typically referred to as output variables of the system wherein the output variables can be affected by adjusting certain input variables.

The terms "controlled compliance" and "controlled compliant" describe the ability to actively control the transfer of fluid volume into or out of a compartment, flow path or circuit. In certain embodiments, the variable volume of fluid in a dialysate circuit or controlled compliant flow path expands and contracts via the control of one or more pumps in conjunction with one or more reservoirs. The volume of fluid in the system is generally constant (unless additional fluids are added to a reservoir from outside of the system) once the system is in operation if the patient fluid volume(s), flow paths, and reservoirs are considered part of the total volume of the system (each individual volume may sometimes be referred to as a fluid compartment). The attached reservoirs allow the system to adjust the patient fluid volume by withdrawing fluid and storing the desired amount in an attached control reservoir and/or by providing purified and/or rebalanced fluids to the patient and optionally removing waste products. The terms "controlled compliance" and "controlled compliant" are not to be confused with the term "non-compliant volume," which simply refers to a vessel, conduit, container, flow path, conditioning flow path or cartridge that resists the introduction of a volume of fluid after air has been removed from a defined space such as a vessel, conduit, container, flow path, conditioning flow path or cartridge. In one embodiment, and as discussed herein and shown in the drawings is that the controlled compliant system can move fluids bi-directionally. In certain cases, the bi-directional fluid movement is across a semi-permeable membrane either inside or outside a dialyzer. The bi-directional fluid flow can also occur across, through, or between vessels, conduits, containers, flow paths, conditioning flow paths or cartridges of the invention in selected modes of operation. The term "moving fluid bi-directionally" as used in connection with a barrier, such as a semi-permeable membrane, refers to the ability to move a fluid across the barrier in either direction. "Moving fluid bi-directionally" also can apply to the ability to move fluid in both directions in the flow path or between a flow path and reservoir in a controlled compliant system.

The terms "controlled compliant flow path", "controlled compliant dialysate flow path" and "controlled compliant solution flow path" refer to flow paths operating within a controlled compliant system having the characteristic of controlled compliance, or of being controlled compliant as defined herein.

The term "convective clearance" refers to the movement of solute molecules or ions across a semi-permeable barrier due to force created by solvent molecules moving across the semi-permeable barrier.

The terms "controller," "control unit," "processor," and "microprocessor" refers, in context, to a device which monitors and affects the operational conditions of a given system.

The operational conditions are typically referred to as output variables of the system wherein the output variables can be affected by adjusting certain input variables.

The terms "coordinately operates" and "coordinately operating" refer to controlling the function of two or more elements or devices so that the combined functioning of the two or more elements or devices accomplishes a desired result. The term does not exclusively imply that all such elements or devices are simultaneously energized.

The term "deaeration" refers to removing some or all of the air contained in a liquid including both dissolved and non-dissolved air contained in the liquid.

The terms "de-aeration flow path" and "de-aeration flow path" refer to a set of elements that are configured in fluid communication along a fluid flow pathway such that a liquid can be passed through the fluid flow pathway to accomplish removal of some or all of the air or gas contained in the liquid, including removal of air or gas that is dissolved in the liquid.

The terms "degas module" and "degassing module" refer to a component that separates and removes any portion of one or more dissolved or undissolved gas from a liquid. A degas module can include a hydrophobic membrane for allowing ingress or egress of gases through a surface of the module while preventing the passage of liquid through that surface of the module.

The term "deionization resin" refers to any type of resin or material that can exchange one type of ion for another. In one specific case, the term can refer to the removal of ions such as potassium, magnesium, sodium and calcium in exchange for hydrogen and/or hydroxide ions.

The term "detachable" refers to a characteristic of an object or apparatus that permits it to be removed and/or disconnected from another object or apparatus.

The term "dialysate" describes a fluid into or out of which solutes from a fluid to be dialyzed diffuse through a membrane. A dialysate typically contains electrolytes that are close in concentration to the physiological concentration of electrolytes found in blood. A common sodium level for dialysate is approximately 140 mEq/L. Normal blood sodium levels range from approximately 135 mEq/L to 145 mEq/L. The REDY system typically uses dialysate ranging from 120 mEq/L to 160 mEq/L. In certain embodiment, a "predetermined limit" or "predetermined concentration" of sodium values can be based off the common sodium levels for dialysate and normal blood sodium levels. "Normal" saline at 0/9% by weight and commonly used for priming dialyzers and extracorporeal circuits is 154 mEq/L.

The terms "dialysate flow loop", "dialysate flow path", and "dialysate conduit flow path" refers, in context, to a fluid pathway that conveys a dialysate and is configured to form at least part of a fluid circuit for hemodialysis, hemofiltration, hemodiafiltration or ultrafiltration.

The terms "dialysate regeneration unit" and "dialysate regeneration system" refer to a system for removing certain electrolytes and waste species including urea from a dialysate after contact with a dialyzer. In certain instances, the component contained within the "dialysate regeneration unit" or "dialysate regeneration system" can decrease the concentration or conductivity of at least one ionic species, or release and/or absorb at least one solute from a dialysate.

"Dialysis" is a type of filtration, or a process of selective diffusion through a membrane. Dialysis removes solutes of a specific range of molecular weights via diffusion through a membrane from a fluid to be dialyzed into a dialysate. During dialysis, a fluid to be dialyzed is passed over a filter membrane, while dialysate is passed over the other side of that membrane. Dissolved solutes are transported across the filter membrane by diffusion between the fluids. The dialysate is used to remove solutes from the fluid to be dialyzed. The dialysate can also provide enrichment to the other fluid.

The terms "dialysis membrane," "hemodialysis membrane," "hemofiltration membrane," "hemodiafiltration membrane," "ultrafiltration membrane," and generally "membrane," refer, in context, to a semi-permeable barrier selective to allow diffusion and convection of solutes of a specific range of molecular weights through the barrier that separates blood and dialysate, or blood and filtrate, while allowing diffusive and/or convective transfer between the blood on one side of the membrane and the dialysate or filtrate circuit on the other side of the membrane.

The term "dialyzer" refers to a cartridge or container with two flow paths separated by semi-permeable membranes. One flow path is for blood and one flow path is for dialysate. The membranes can be in the form of hollow fibers, flat sheets, or spiral wound or other conventional forms known to those of skill in the art. Membranes can be selected from the following materials of polysulfone, polyethersulfone, poly(methyl methacrylate), modified cellulose, or other materials known to those skilled in the art.

"Diffusive permeability" is a property of a membrane describing permeation by diffusion. Diffusion is the process of solutes moving from an area of higher concentration to an area of lower concentration.

The terms "diluate flow channel," "feed stream," "diluate stream," and the like, refer, in context, to a fluid line of solution entering an electrodialysis cell or electrodialysis unit wherein the ion concentration in the fluid solution is changed.

The terms "diluent" and "diluate" refer to a fluid having a concentration of a specific species less than a fluid to which the diluent is added.

A "disc electrode" consists of an electrode with an electrode head in the shape of a disc. A "rod electrode" refers to an electrode in the shape of a rod or cylinder, with one end functioning as an electrode head. A "sheet electrode" refers to an electrode with an electrode head in the shape of a sheet. The sheet can be square, rectangular, circular or other solid planar geometries. A "mesh electrode" refers to an electrode with an electrode head consisting of a mesh, where a mesh is the same as that described for a mesh electrode. An "antenna electrode" refers to an electrode with an electrode head in the shape of an antenna, where antenna shape refers to a serpentine structure of conductive wires or strips. A "pin electrode refers" to a rod electrode with a small diameter. Other electrode and electrode head geometries can be considered.

The term "disinfection fluid" refers to a solution for use in cleaning and disinfecting an apparatus for hemodialysis, hemodiafiltration or hemofiltration. The disinfection fluid may act thermally, chemically, and combinations thereof to inhibit growth of or to destroy microorganisms. The "disinfection fluid" may further act to remove, at least in part, a buildup of microorganisms on a surface of a fluid flow path, such buildups of microorganisms may be commonly referred to as a biofilm.

The terms "diverted sample stream" and "diverting a sample stream" refer redirecting part of a fluid from the main flow path to accomplish another purpose, such as to measure a fluid characteristic, remove a portion of the fluid stream in order to take a sample. More that one sample stream may be diverted, such as a "first sample stream, "second sample stream", "third sample stream", "fourth sample stream", and the like.

The term "dry" as applied to a solid or a powder contained in a cartridge means not visibly wet, and may refer interchangeably to anhydrous and also to partially hydrated forms of those materials, for example, monohydrates and dihydrates.

The term "downstream" refers to a direction in which a moving dialysate or other fluid moves within a conduit or flow path.

The term "downstream conductivity" refers to the conductivity of a fluid solution as measured at a location of a fluid flow path in the direction of the normal fluid flow from a reference point.

The term "drain connection" refers to being joined in fluid communication with a conduit or vessel that can accept fluid egress from the system.

The term "dry composition" refers to a compound that does not contain a substantial quantity of water and can include anhydrous forms as well as hydrates for example, monohydrates and dihydrates.

The term "effluent dialysate," as used herein describes the discharge or outflow after the dialysate has been used for dialysis.

The term "electrode" as used herein describes an electrical conductor used to make contact with a part of a fluid, a solid or solution. For example, electrical conductors can be used as electrodes to contact any fluid (e.g. dialysate) to measure the conductivity of the fluid or deliver or receive charge to the fluid. A "disc electrode" consists of an electrode with an electrode head in the shape of a disc. A "rod electrode" refers to an electrode in the shape of a rod or cylinder, with one end functioning as an electrode head. A "sheet electrode" refers to an electrode with an electrode head in the shape of a sheet. The sheet can be square, rectangular, circular or other solid planar geometries. A "mesh electrode" refers to an electrode with an electrode head consisting of a mesh, where a mesh is the same as that described for a mesh electrode. An "antenna electrode" refers to an electrode with an electrode head in the shape of an antenna, where antenna shape refers to a serpentine structure of conductive wires or strips. A "pin electrode" refers to a rod electrode with a small diameter. Other electrode and electrode head geometries can be considered.

The term "electrode array" refers to an array of one or more electrodes contained in an insulator substrate. The insulator substrate can be rigid or flexible and acts to isolate the electrodes from each other. A non-limiting example of an "electrode array" is a flex-circuit, which is a flexible circuit board containing electrodes.

The term "electrode head" refers to the portion of an electrode that is in physical contact with a fluid, that conductivity is to be measured from.

The terms "electrode rinse" and "electrode rinse solution" refer to any suitable solution such as sodium sulfate solution that prevents undesirable oxidation and flushes reactants from an electrode surface.

The terms "electrode rinse flow channel," "electrode rinse stream," and the like refer to a fluid line of an electrode rinse or "electrode rinse solution."

The term "electrode rinse reservoir" refers to a vessel or container for holding the electrode rinse or electrode rinse solution. The reservoir may have an inflexible or flexible volume capacity.

The term "electrodialysis" refers to an electrically driven membrane separation process capable of separating, purifying, and concentrating desired ions from aqueous solutions or solvents.

The term "electrodialysis cell" refers to an apparatus having alternating anion- and cation-exchange membranes that can perform electrodialysis using an electrical driving force between an anode and cathode housed at opposite ends of the cell. The cell consists of a diluate compartment fed by a diluate stream and a concentrate compartment fed by a concentrate stream. One or more electrodialysis cells can be multiply arranged to form an "electrodialysis stack."

The term "electrolyte" refers to an ion or ions dissolved in an aqueous medium, including but not limited to sodium, potassium, calcium, magnesium, acetate, bicarbonate, and chloride.

The terms "electrolyte source" and "electrolyte source" refer to a stored substance that provides one or more electrolytes.

The terms "equilibrated," "equilibrate," "to equilibrate," and the like, refer to a state where a concentration of a solute in a first fluid has become approximately equal to the concentration of that solute in the second fluid. However, the term equilibrated as used herein does not imply that the concentration of the solute in the first fluid and the second fluid have become equal. The term can also be used in reference to the process of one or more gases coming into equilibrium where the gases have equal pressures or between a liquid and a gas.

The term "equilibrated to the solute species concentration" refers to more specifically where a concentration of a particular solute species in a first fluid has become approximately equal to the concentration of that solute species in the second fluid. The concentration need not be exact.

The terms "evacuation volume", "priming volume" and "void volume" refer to the internal volume of a component or collection of components comprising a fluid flow path and are the volume of fluid that can be removed from the fluid flow path to empty the fluid flow path if it has been filled with fluid.

The term "extracorporeal," as used herein generally means situated or occurring outside the body.

The term "extracorporeal circuit" refers to a fluid pathway incorporating one or more components such as, but not limited to, conduits, valves, pumps, fluid connection ports or sensing devices configured therein such that the pathway conveys blood from a subject to an apparatus for hemodialysis, hemofiltration, hemodiafiltration or ultrafiltration and back to the subject.

The terms "extracorporeal flow path pump" and "blood pump" refer to a device to move or convey fluid through an extracorporeal circuit. The pump may be of any type suitable for pumping blood, including those known to persons of skill in the art, for example peristaltic pumps, tubing pumps, diaphragm pumps, centrifugal pumps, and shuttle pumps.

The term "feed solution" refers to a dialysate or ultrafiltrate fluid solution introduced into part of the dialysis or ultrafiltrate system. For example a "feed solution" can refer to a dialysate or ultrafiltrate fluid solution introduced to an electrodialysis cell.

The term "filtering media" refers to a material that can allow a fluid to pass through, but which inhibits passage of non-fluid substances that are larger than a predetermined size.

The terms "filtrate regeneration unit" and "filtrate regeneration system" refer to a system for removing certain electrolytes and waste species including urea from a filtrate produced using filtration.

The terms "filtrate regeneration circuit", "filtrate regeneration loop", and the like, refer to a flow path containing fluid resulting from filtration; for the removal of certain electrolytes and waste species including urea.

The term "filtration" refers to a process of separating solutes from a fluid, by passing the fluid through a filter medium across which certain solutes or suspensions cannot pass. Filtration is driven by the pressure difference across the membrane.

The term "first terminal end" of a flow path refers to one end of the flow path and "second terminal end" refers to another end of the flow path. Neither the "first terminal end" nor the "second terminal end" has any limitation on placement on an arterial or venous side.

The term "first terminal valve" refers to a valve substantially located at one end of a first fluid conduit without any requirement that the valve be place on an arterial or venous side. Similarly, the term "second terminal valve" refers to a valve substantially located at one end of a second fluid conduit and so on without any limitation on placement on an arterial or venous side.

The term "flow loop" refers to a grouping of components that may guide the movement of a fluid, convey the fluid, exchange energy with the fluid, modify the composition of the fluid, measure a characteristic of the fluid and/or detect the fluid. A flow loop comprises a route or a collection of routes for a fluid to move within. Within a flow loop there may be more than one route that a volume of fluid can follow to move from one position to another position. A fluid volume may move through a flow loop such that it recirculates, or passes the same position more than once as it moves through a flow loop. A flow loop may operate to cause fluid volume ingress to and fluid volume egress from the flow loop. The term "flow loop" and "flow path" often may be used interchangeably.

The term "flow path" refers to a route or a collection of routes for a fluid to move within. Within a flow path there may be more than one route that a fluid can follow to move from a first position to a second position. A fluid may move through a flow path such that it recirculates, or passes the same position more than once as it moves through a flow path. A flow path may be a single element such as a tube, or a flow path may be a grouping of components of any type that guide the movement of a fluid. The term "flow loop" and "flow path" often may be used interchangeably. Further types of flow paths may be further defined; for example, (1) a recirculation flow path, would be a flow path whose function is in whole or part is to recirculate fluid through the defined flow path; (2) a dialyzer recirculation flow path would be a flow path whose function is in whole or part is to recirculate fluid through the defined flow path having a dialyzer' (3) a controlled compliant flow path would be a flow path would be a flow path that is controlled compliant as defined herein. Any of the defined flow paths may be referred to numerically, as a first flow path, second, third flow path, or fourth flow path, and the like flow paths.

The terms "flow restriction", "flow restriction device" and "flow restrictor" refer to an element or grouping of elements that resist the flow of fluid through the element or grouping of elements such that the fluid pressure within a flow stream that passes through the element or grouping of elements is greater upstream of the element or grouping of elements than downstream of the element or grouping of elements. A flow restrictor may be an active or passive device. Non-limiting examples of passive flow restriction devices are orifices, venturis, a narrowing, or a simple length of tubing with flow cross section that produces the desired pressure drop when the fluid flows through it, such tubing being essentially rigid or compliant. Non-limiting examples of active flow restrictors are pinch valves, gate valves and variable orifice valves.

The term "flow stream" refers to fluid moving along a flow path

The term "fluid balance control pump" refers to where a control pump is used to adjust the concentration or amount of a solute or fluid in the system. For example, a fluid balance control pump is used for selectively metering in or selectively metering out a designated fluid wherein the concentration or amount of a solute or fluid is adjusted.

The term "fluid characteristic" refers to any chemical or biological components that make up or can be found dissolved or suspended in the fluid or gas properties associated with the fluid; or to any physical property of the fluid including, but not limited to temperature, pressure, general or specific conductivities associated with the fluid or related gases.

The term "fluid communication" refers to the ability of fluid to move from one component or compartment to another within a system or the state of being connected, such that fluid can move by pressure differences from one portion that is connected to another portion.

The term "fluid port" refers to an aperture through which a liquid or gas can be conveyed.

The term "fluid port cap or plug" refers to a device that can be connected to a fluid port to prevent fluid from passing through the fluid port. A fluid cap or plug may be configured into an apparatus having multiple caps or plugs to prevent fluid from passing through multiple fluid ports when the apparatus is connected to the multiple fluid ports.

The term "flush reservoir" is used to describe a container that can accept or store fluid that is removed from the system during rinsing or cleaning of fluid pathways of the system, including draining the system after cleaning and/or disinfection has been completed.

The term "forward osmosis" refers to a filtration method using an osmotic pressure gradient wherein a permeate side of a membrane contains a "draw" solution which has a higher osmotic potential than a feed solution on the other side of the membrane. That higher osmotic potential in the "draw" solution drives the filtration process wherein fluid moves through the membrane and is filtered in the process to dilute the higher solute concentration fluid on the permeate side.

The term "gas port" refers to an aperture through which any gaseous form of matter can be conveyed.

"Gas phase pressure", also known as "vapor", is the equilibrium pressure from a liquid or a solid at a specific temperature. If the vapor is in contact with a liquid or solid phase, the two phases will be in a state of equilibrium.

"Hemodiafiltration" is a therapy that combines hemofiltration and hemodialysis.

"Hemofiltration" is a therapy in which blood is filtered across a semi-permeable membrane. Water and solutes are removed from the blood via pressure-driven convection across the membrane. The sieving properties of the membrane exclude certain solutes above a certain threshold from crossing the membrane. One common sieving property is "albumin sieving." In most situations it is not desirable to remove albumin during renal replacement therapy, as lower blood serum albumin is associated with increased mortality rates. In hemofiltration, solutes small enough to pass through the membrane in proportion to their plasma concentration are removed. The driving force is a pressure gradient rather than a concentration gradient. A positive hydrostatic pressure drives water and solutes across the filter membrane from the blood compartment to the filtrate compartment, from which it is drained. Solutes, both small and large, get dragged through the membrane at a similar rate by the flow of water that has been engineered by the hydrostatic pressure. Hence, convection overcomes the reduced removal rate of larger solutes (due to their slow speed of diffusion) observed in hemodialysis. The rate of solute removal is proportional to the amount of fluid removed from the blood circuit, which can be adjusted to meet the needs of a clinical situation. In general, the removal of large amounts of plasma water from the patient requires volume substitution. Substitution fluid, typically a buffered solution close to the plasma water composition a patient needs, can be administered pre or post filter (pre-dilution mode, post-dilution mode).

"Hemodialysis" is a technique where blood and a "cleansing fluid" called dialysate are exposed to each other separated by a semi-permeable membrane. Solutes within the permeability range of the membrane pass while diffusing along existing concentration gradients. Water and solutes are also transferred by convection across a pressure gradient that may exist across the dialysis membrane. The dialysate employed during hemodialysis has soluble ions such as sodium, calcium and potassium ions and is not pure water. The sieving properties of the membrane exclude certain solutes above a certain threshold from crossing the membrane. One common sieving property is "albumin sieving." In most situations it is not desirable to remove albumin during renal replacement therapy, as lower blood serum albumin is associated with increased mortality rates.

The term "hemofilter" refers to a apparatus (or may refer to a filter) used in hemofiltration. A hemofilter apparatus can be connected to an extracorporeal circuit and configured to operate with a semipermeable membrane that separates at least a portion of the fluid volume from blood to produce a filtrate fluid.

The term "horizontal to a central axis" refers to a relative position of components such as sensors that can be placed in a plane having portions generally horizontal to the central axis.

The term "hydrophobic membrane" refers to a semipermeable porous material that may allow gas phases of matter to pass through, but which substantially resists the flow of water through the material due to the surface interaction between the water and the hydrophobic material.

The terms "hydrophobic vent" and "hydrophobic vent membrane" refer to a porous material layer or covering that can resist the passage of a liquid such as water through the pores while allowing the passage of a gas. The pores may also be of a sufficiently small size to substantially prevent the passage of microorganisms.

"Hemodiafiltration" is a therapy that combines hemofiltration and hemodialysis.

The term "perpendicular to a central axis" refers to the position of components, e.g. sensors that can be placed in a plane having portions generally perpendicular to the central axis.

The term "in contact" as referred to herein denotes (a) a coming together or touching, as of objects or surfaces; or (b) the state or condition of touching or of being in immediate proximity. "In contact" also includes fluids that are "in fluid communication with" with a solid, such as for example, a fluid, like a dialysate, in contact with a material layer of a sorbent cartridge, or a fluid in contact with a sensor.

The term "impedance meter" refers to a device for measuring the opposition of an object or structure to an alternating current.

The term "impurity species" refers to solutes in the blood that are in too high of a concentration in the blood from standard ranges known in the art or that are solutes that have resulted from metabolism to generate a non-healthy component now residing in the blood. An "impurity species" is one which is also regarded as a "waste species," or "waste products".

The term "ion selective electrode" refers to electrodes coated with a material that only allows certain ions to pass through. An "ion selective electrode" (ISE), also known as a specific ion electrode (SIE), is a transducer (or sensor) that converts the activity of a specific ion dissolved in a solution into an electrical potential, which can be measured by a voltmeter or pH meter. The voltage is theoretically dependent on the logarithm of the ionic activity, according to the Nernst equation. The sensing part of the electrode is usually made as an ion-specific membrane, along with a reference electrode.

The terms "infusate container" and "infusate reservoir" refer to a vessel, which can be substantially inflexible or non-flexible for holding a solution of one or more salts for the adjustment of the composition of a dialysate.

The term "infusate solution" refers to a solution of one or more salts for the adjustment of the composition of a dialysate, such as salts of calcium, magnesium, potassium, and glucose.

The term "infusate system" refers to a system that incorporates at least one fluid pathway including components such as conduits, valves, pumps or fluid connection ports, an infusate container or a controller configured to add an infusate solution to the dialysate.

The term "interchangeable bicarbonate cartridge" refers to a bicarbonate cartridge that can be configured for removal and replacement with a like bicarbonate cartridge. Interchangeable bicarbonate cartridges can be single use disposable, or re-fillable, re-usable containers.

The term "interchangeable sodium chloride cartridge" refers to a sodium chloride cartridge that can be configured for removal and replacement with a like sodium chloride cartridge. Interchangeable sodium chloride cartridges can be single use disposable, or re-fillable, re-usable containers.

The terms "introduce" and "introducing" refer to causing a substance to become present where it was not present, or to cause the amount or concentration of a substance to be increased.

The term "ion-exchange material" refers to any type of resin or material that can exchange one type of ion for another. The "ion-exchange material" can include anion and cation exchange materials. In one specific case, the term can refer to the removal of ions such as potassium, magnesium, sodium, phosphate and calcium in exchange for other ions such as potassium, sodium, acetate, hydrogen and/or hydroxide.

An "ion-exchange resin" or "ion-exchange polymer" is an insoluble matrix (or support structure) that can be in the form of small (1-2 mm diameter) beads, fabricated from an organic polymer substrate. The material has a developed structure of pores on the surface of which are sites with easily trapped and released ions. The trapping of ions takes place only with simultaneous releasing of other ions; thus the process is called ion-exchange. There are multiple different types of ion-exchange resin which are fabricated to selectively prefer one or several different types of ions. In one specific case, the term can refer to the removal of ions such as potassium, magnesium, sodium, phosphate and calcium in exchange for other ions such as potassium, sodium, acetate, hydrogen and/or hydroxide.

The term "junction" refers to a common point of connection between two or more flow paths or conduits that allows a liquid and/or a gas to move from one pathway or conduit to another. A junction may be a reversible connection that can be separated when transfer of a liquid and/or gas between the flow paths or conduits is not needed.

The term "kidney replacement therapy" as used herein describes the use of a provided system to replace, supplement, or augment the function of a patient with impaired kidney function, such as would occur for a patient with Chronic Kidney Disease. Examples of kidney replacement therapy would include dialysis, hemofiltration, hemodialysis, hemodiafiltration, peritoneal dialysis, and the like.

The terms "luer connector" and "luer adapter" refer to adapters or connectors conforming to International Standards Organization (ISO) standards 594-2.

The term "manifold" refers to a collection of one or more fluid pathways that are formed within a single unit or subassembly. Many types of manifolds can be used, e.g. a cleaning and/or disinfecting manifold is used to clean or disinfect the defined flow loop when the flow loop is connected to the cleaning and/or disinfecting manifold.

The term "material layer" refers to the layers of materials found in a sorbent cartridge. The material layers in a sorbent cartridge may have one or more layers selected from a urease-containing material, alumina, zirconium phosphate, zirconium oxide, and activated carbon.

The term "memory" refers to a device for recording digital information that can be accessed by a microprocessor, such as RAM, Dynamic RAM, microprocessor cache, FLASH memory, or memory card.

The term "mesh electrode" refers to an electrode in the shape of a mesh, where a mesh consists of a planar structure with openings. The mesh can be made from; overlapping wires or strips, a sheet machined or manufactured to contain holes or openings, or a sheet with a permeable, porous structure. In all cases the mesh is manufactured from materials that result in electrodes, such as titanium, platinum, stainless steel, and iridium. In the case of an electrode mesh consisting of overlapping wires or strips, certain wires or strips can be isolated from other wires or strips with an insulator material in order to apply one polarity to certain wires or strips and the opposite polarity to other wires or strips.

The term "metabolic waste species," as used herein describes organic and inorganic components generated by a patient. They can be metabolic products such as urea, uric acid, creatinine, chlorides, inorganic sulfates and phosphate, or excess electrolytes such as sodium, potassium, etc. It will be understood that the specific "metabolic waste species" can vary between individuals depending on diet and environmental factors. Hence, the term is intended to encompass any waste component that is normally removed by a kidney or by dialysis without restriction on the specific type of waste substance.

The term "mid-weight uremic wastes" refers to uremic wastes that can pass through a dialysis membrane and have a molecular weight less than about 66,000 g/mol and greater than about 1000 g/mol. An example of a middle molecule is beta-2 microglobulin.

The term "mixing chamber" refers to a chamber or vessel, with one or more inlet and outlet fluid streams, that provides mixing between the fluid streams entering the chamber.

The term "moving fluid bi-directionally" as used in connection with a barrier, such as a semi-permeable membrane, refers to the ability to move a fluid across the barrier in either direction. "Moving fluid bi-directionally" also can apply to the ability to move fluid in both directions in the flow loop in a controlled compliant system.

A multiplexer" or "mux" is an electronic device that selects one of several analog or digital input signals and forwards the selected input into a single line.

The term "nitrogenous waste" refers to any non-polymeric nitrogen-containing organic compound originating from the blood of a patient. Nitrogenous waste includes urea and creatinine, which are both "waste species."

The term "one-way valve" refers to a device that allows flow to pass in one direction through the valve, but prevents or substantially resists flow through the valve in the opposite direction. Such devices can include devices commonly referred to as check valves "Osmolarity" is defined as the number of osmoles of a solute per liter of solution. Thus, a "hyperosmolar solution" represents a solution with an increase in osmolarity compared to physiologic solutions. Certain compounds, such as mannitol, may have an effect on the osmotic properties of a solution as described herein.

The term "parallel or wound hollow fiber assembly" refers to any device that incorporates a porous or non-porous hollow fiber material that allows a gas to pass through the material wall of the hollow fibers, but resists the passage of a liquid through the material wall and is configured as multiple strands aligned in parallel or wrapped around a core. The liquid to be degassed may be conveyed through either the inside of the hollow fibers or around the outside of the hollow fibers. Optionally, a gas may be conveyed on the side of the material wall that is opposite the liquid to be degassed. Optionally, a vacuum may be applied on the side of the material wall that is opposite the liquid to be degassed.

A "patient" or "subject" is a member of any animal species, preferably a mammalian species, optionally a human. The subject can be an apparently healthy individual, an individual suffering from a disease, or an individual being treated for a disease.

The term "parallel to a central axis" refers to the position of components, e.g. sensors that can be placed in a plane having portions generally parallel to the central axis.

The terms "pathway," "conveyance pathway" and "flow path" refer to the route through which a fluid, such as dialysate or blood travels.

The term "patient fluid balance" refers to the amount or volume of fluid added to or removed from a subject undergoing a treatment.

The term "peristaltic pump" refers to a pump that operates by compression of a flexible conduit or tube through which the fluid to be pumped passes.

The term "perpendicular to a central axis" refers to the position of components, e.g. sensors that can be placed in a plane having portions generally perpendicular to the central axis.

"Peritoneal dialysis" is a therapy wherein a dialysate is infused into the peritoneal cavity, which serves as a natural dialyzer. In general, waste components diffuse from a patient's bloodstream across a peritoneal membrane into the dialysis solution via a concentration gradient. In general, excess fluid in the form of plasma water flows from a patient's bloodstream across a peritoneal membrane into the dialysis solution via an osmotic gradient.

The term "pH-buffer modifying solution" refers to a solution that can reduce the acidity (pH) of the working dialysate solution when added to the dialysate.

The term "pH-buffer sensor" refers to a device for measuring the acidity or basicity (pH) and the buffer concentration of the dialysate solution.

The term "pH-buffer management system" refers to a system managing the pH and buffer concentration of a dialysate by adding, removing or generating a fluid to the dialysate such that the dialysate is modified by the pH-buffer management system to have a different pH and buffer concentration.

The term "pH-buffer measurement system" refers to a system measuring the pH and/or buffer concentration of a dialysate or fluid within the system.

The terms "portable system" and "wearable system" refers to a system in whole or in part having a mass and dimension to allow for transport by a single individual by carrying the system or wearing the system on the individual's body. The terms are to be interpreted broadly without any limitation as to size, weight, length of time carried, comfort, ease of use, and specific use by any person whether man, woman or child. The term is to be used in a general sense wherein one of ordinary skill will understand that portability as contemplated by the invention encompasses a wide range of weights, geometries, configurations and size.

The term "potable water" refers to drinking water or water that is generally safe for human consumption with low risk of immediate or long term harm. The level of safety for human consumption can depend on a particular geography where water safe for human consumption may be different from water considered safe in another jurisdiction. The term does not necessarily include water that is completely free of impurities, contaminants, pathogens or toxins. Other types of water suitable for use in the present invention can include purified, deionized, distilled, bottled drinking water, or other pre-processed water that would be understood by those of ordinary skill in the art as being suitable for use in dialysis.

The term "potassium-modified fluid" refers to fluid having a different conductivity or potassium concentration compared to a second fluid to which the potassium-modified fluid is added to modify the conductivity or potassium concentration of the second fluid.

The terms "physiologically compatible fluid" and "physiological compatible solution" refer to a fluid that can be safely introduced into the bloodstream of a living subject.

The term "plumbing," as used herein generally describes any system of valves, conduits, channels, and lines for supplying any of the fluids used in the invention.

The term "porosity," as used herein describes the fraction of open pore volume of a membrane.

The terms "pressure differential" and "pressure drop" refer to the difference in pressure measurements of a fluid between two points of measurement.

The terms "pressure meter" and "pressure sensor" refer to a device for measuring the pressure of a gas or liquid in a vessel or container.

The terms "priming process" and "priming" refer to the process of conveying a liquid into the void volume of a fluid pathway to fill the pathway with liquid.

The term "priming volume" refers to the volume of priming fluid required to fill the void volume of the subject pathway, device, or component, as the particular case may be.

The term "priming overflow reservoir" refers to a reservoir which during priming is used to collect the overflow of fluid during the priming process.

The terms "processor," "computer processor," and "microprocessor" as used herein are broad terms and are to be given their ordinary and customary meaning to a person of ordinary skill in the art. The terms refer without limitation to a computer system, state machine, processor, or the like designed to perform arithmetic or logic operations using logic circuitry that responds to and processes the basic instructions that drive a computer. In some embodiments, the terms can include ROM ("read-only memory") and/or RAM ("random-access memory") associated therewith.

The term "programmable" as used herein refers to a device using computer hardware architecture with a stored program and being capable of carrying out a set of commands, automatically that can be changed or replaced.

The term "pump" refers to any device that causes the movement of fluids or gases by the application of suction or pressure.

The term "pulsatile pump" refers to a pump where the pumped fluid undergoes periodic variation in velocity and/or pressure.

The terms "pump rate" and "volumetric pumping rate" refer to the volume of fluid that a pump conveys per unit of time.

The term "purified water" refers to water that has been physically processed to remove at least a portion of at least one impurity from the water.

The term "outlet stream" refers to a fluid stream exiting a chamber, vessel or cartridge.

The terms "reconstitute" and "reconstituting" refer to creating a solution by addition of a liquid to a dry material or to a solution of higher concentration to change the concentration level of the solution. A "reconstitution system" in one use, is a system that rebalances the dialysate in the system to ensure it contains the appropriate amount of electrolytes and buffer.

The term "refilled" refers to having replenished or restored a substance that has been consumed or degraded.

The terms "sorbent regeneration", "sorbent regeneration system", "sorbent system, and the like, refer, in context, to devices that are part of a sorbent regenerated dialysate delivery system for hemodialysis, functioning as an artificial kidney system for the treatment of patients with renal failure or toxemic conditions, and that consists of a sorbent cartridge and the means to circulate dialysate through this cartridge and the dialysate compartment of the dialyzer. The device is used with the extracorporeal blood system and the dialyzer of the hemodialysis system and accessories. The device may include the means to maintain the temperature, conductivity, electrolyte balance, flow rate and pressure of the dialysate, and alarms to indicate abnormal dialysate conditions. The sorbent cartridge may include absorbent, ion exchange and catalytics.

The term "shunt," as most often used herein describes a passage between channels, in the described filtration and purification systems, wherein the shunt diverts or permits flow from one pathway or region to another. An alternate meaning of "shunt" can refer to a pathway or passage by which a bodily fluid (such as blood) is diverted from one channel, circulatory path, or part to another. The term "bypass" can often be used interchangeably with the term "shunt."

The term "sodium-concentrate solution" refers to a solution having a high concentration of sodium ions relative to another solution or fluid.

The terms "sodium chloride cartridge" and "sodium chloride container" refer to an object that can be a stand-alone enclosure or alternatively can be integrally formed with an apparatus for hemodialysis, hemodiafiltration, or hemofiltration. The object can store a source of sodium, such as sodium chloride in solid and/or solution form, and can be configured to interface with at least one other functional module found in systems for hemodialysis, hemodiafiltration, or hemofiltration. For example, the sodium chloride cartridge or container can contain at least one fluid pathway and include components such as conduits, valves, filters or fluid connection ports.

The term "regenerative capacity of the sorbent" refers to the remaining capacity for the sorbent cartridge or a particular material layer of the sorbent cartridge to perform its intended function.

The term "regenerative substance" refers to a sorbent material contained in a "regeneration module." The term "first chosen regenerative substance," as used in the present invention refers to a particular regenerative substance, identified as "first chosen regenerative substance." The term "second chosen regenerative substance" refers to a particular regenerative substance, identified as "second chosen regenerative substance."

The term "regeneration module" refers to an enclosure having one or more sorbent materials for removing specific solutes from solution, such as urea. In certain embodiments, the term "regeneration module" refers to one or more regeneration cartridge or regeneration unit. In certain embodiments, the term "regeneration module" includes configurations where at least some of the materials contained in the module do not act by mechanisms of adsorption or absorption.

The terms "remnant volume" and "residual volume" refer to the volume of fluid remaining in a fluid flow path after the fluid flow path has been partially emptied or evacuated.

The terms "replacement fluid" and "substitution fluid" refer to fluid that is delivered to the blood of a subject undergoing convective renal replacement therapies such as hemofiltration or hemodiafiltration in order to replace at least a portion of the fluid volume that is removed from the subject's blood when the blood is passed through a hemofilter or a dialyzer.

The term "reserve for bolus infusion" refers to an amount of solution available, if needed, for the purpose of administering fluid to a subject receiving therapy, for example, to treat an episode of intradialytic hypotension.

The term "reusable" refers to an item that is used more than once. Reusable does not imply infinitely durable. A reusable item may be replaced or discarded after one or more use.

The term "reverse osmosis" refers to a filtration method of forcing a solvent from a region of high solute concentration through a semi-permeable membrane to a region of low solute concentration by applying a pressure in excess of osmotic pressure. To be "selective," this membrane should not allow large molecules or ions through the pores (holes), but should allow smaller components of the solution (such as the solvent) to pass freely.

The term "reverse osmosis rejection fraction" refers to the resulting solute that is retained on the pressurized side of the membrane and the pure solvent is allowed to pass to the other side in a reverse osmosis system.

The term "reversible connections" refers to any type of detachable, permanent or non-permanent connection configured for multiple uses.

The term "salination pump" refers to a pump configured to move fluid and/or control movement of fluid through a conditioning flow path, such as through or from a source of a conditioning material such as sodium chloride or sodium bicarbonate.

The term "salination valve" refers to a valve configured to control the flow of fluid in a conditioning flow path, such as through or from a source of a conditioning material such as sodium chloride or sodium bicarbonate.

The term "segment" refers to a portion of the whole, such as a portion of a fluid flow path or a portion of a fluid circuit. A segment is not limited to a tube or conduit, and includes any grouping of elements that are described for a particular segment. Use of the term "segment," by itself, does not imply reversible or detachable connection to another segment. In any embodiment, a segment may be permanently connected to one or more other segments or removably or detachably connected to one or more segments.

The terms "selectively meter fluid in" and "selectively meter fluid out" generally refer to a process for controllably transferring fluids from one fluid compartment (e.g. a selected patient fluid volume, flow path, or reservoir) to another fluid compartment. One non-limiting example is where a control pump may transfer a defined fluid volume container, reservoirs, flow paths, conduit of the controlled compliant system. When fluid is moved from a reservoir into another part of the system, the process is referred to as "selectively metering fluid in" as related to that part of the system. Similarly, one non-limiting example of removing a defined volume of dialysate from a dialysate flow path in a controlled compliant system and storing the spent dialysate in a control reservoir, can be referred to as "selectively metering-out" the fluid from the dialysate flow path.

The terms "semi-permeable membrane", "selectively permeable membrane", "partially permeable membrane", and "differentially permeable membrane", refer to a membrane that will allow certain molecules or ions to pass through it by diffusion and occasionally specialized "facilitated diffusion". The rate of passage depends on the pressure, concentration, and temperature of the molecules or solutes on either side, as well as the permeability of the membrane to each solute. The term "semi-permeable membrane" can also refer to a material that inhibits the passage of larger molecular weight components of a solution while allowing passage of other components of a solution having a smaller molecular weight. For example, Dialyzer membranes come with different pore sizes. Those with smaller pore size are called "low-flux" and those with larger pore sizes are called "high-flux." Some larger molecules, such as beta-2-microglobulin, are not effectively removed with low-flux dialyzers. Because beta-2-microglobulin is a large molecule, with a molecular weight of about 11,600 daltons, it does not pass effectively through low-flux dialysis membranes.

The term "sensor," which can also be referred to as a "detector" in certain instances, as used herein can be a converter that measures a physical quantity of a matter in a solution, liquid or gas, and can convert it into a signal which can be read by an electronic instrument.

The term "sensor element" refers to a device or component of a system that detects or measures a physical property.

The terms "sodium management system" and "sodium management" broadly refer to a system or process that can maintain the sodium ion concentration of a fluid in a desired range. In certain instances, the desired range can be within a physiologically-compatible range. The sodium ion concentration of an input solution can be modified by any means including application of an electrical field.

The term "sodium-modified fluid" refers to fluid having a different conductivity or sodium concentration compared to a second fluid to which the sodium-modified fluid is added to modify the conductivity or sodium concentration of the second fluid.

The term "sodium conduit flow path" refers to a flow path in fluid communication with a sodium chloride cartridge which then can pump saturated sodium solution into the dialysate by pumping and metering action of a salination pump.

The term "sodium source" refers to a source from which sodium can be obtained. For example, the sodium source can be a solution containing sodium chloride or a dry sodium chloride composition that is hydrated by the system.

The term "solid potassium" refers to a solid composition containing a salt of potassium such as potassium chloride at any purity level. In general, the solid potassium will be easily soluble in water to form a solution.

The term "solid sodium" refers to a solid composition containing a salt of sodium such as sodium chloride at any purity level. In general, the solid potassium will be easily soluble in water to form a solution and of high purity.

The term "solid bicarbonate" refers to a composition containing a salt of bicarbonate such as sodium bicarbonate at any purity level. In general, the solid bicarbonate will be easily soluble in water to form a solution.

The term "solute" refers to a substance dissolved, suspended, or present in another substance, usually the component of a solution present in the lesser amount.

The terms "sorbent cartridge" and "sorbent container" refer to a cartridge containing one or more sorbent materials for removing specific solutes from solution, such as urea. The term "sorbent cartridge" does not necessarily require the contents in the cartridge be sorbent based. In this connection, the sorbent cartridge may include any suitable amount of one or more sorbent materials. In certain instances, the term "sorbent cartridge" refers to a regeneration cartridge which may include one or more sorbent materials in addition to one or more other regeneration materials. "Sorbent cartridge" includes configurations where at least some of the materials contained in the cartridge do not act by mechanisms of adsorption or absorption.

The term "source of cations" refers a source from which cations can be obtained. Examples of cations include, but are not limited to, calcium, magnesium and potassium. The source can be a solution containing cations or a dry composition that is hydrated by the system. The cation infusate source is not limited to cations and may optionally include other substances to be infused into a dialysate or replacement fluid. Non-limiting examples include glucose, dextrose, acetic acid and citric acid.

The term "specified gas membrane permeability" refers to a determined rate at which a gas membrane will allow a gas to pass through the membrane from a first surface to a second surface, the rate being proportional to the difference in absolute pressure of the gas in proximity to the first side of the membrane and in proximity to the second side of the membrane.

The term "spent dialysate" refers to a dialysate that has been contacted with blood through a dialysis membrane and contains one or more impurity, or waste species, or waste substance, such as urea.

The term "static mixer" refers to a device that mixes two or more component materials in a fluid solution without requiring the use of moving parts.

The term "substantially inflexible volume" refers to a three-dimensional space within a vessel or container that can accommodate a maximum amount of non-compressible fluid and resists the addition of any volume of fluid above the maximum amount. The presence of a volume of fluid less than the maximum amount will fail to completely fill the vessel or container. Once a substantially inflexible volume has been filled with a fluid, removal of fluid from that volume will create a negative pressure that resists fluid removal unless fluid is added and removed simultaneously at substantially equal rates. Those skilled in the art will recognize that a minimal amount of expansion or contraction of the vessel or container can occur in a substantially inflexible volume; however, the addition or subtraction of a significant volume of fluid over a maximum or minimum will be resisted.

The term "tap water" refers to water, as defined herein, from a piped supply.

The term "temperature sensor" refers to a device that detects or measures the degree or intensity of heat present in a substance, object, or fluid.

A "therapy solution reservoir" refers to any container or reservoir that holds a physiological compatible fluid.

The term "total bicarbonate buffer concentration" refers to the total concentration of bicarbonate ($HCO_3^-$) ion and a conjugate acid of bicarbonate in a solution or composition.

A "therapy solution reservoir" refers to any container or reservoir that holds a physiological compatible fluid.

The terms "treating" and "treatment" refer to the management and care of a patient having a pathology or condition by administration of one or more therapy contemplated by the present invention. Treating also includes administering one or more methods of the present invention or using any of the systems, devices or compositions of the present invention in the treatment of a patient. As used herein, "treatment" or "therapy" refers to both therapeutic treatment and prophylactic or preventative measures. "Treating" or "treatment" does not require complete alleviation of signs or symptoms, does not require a cure, and includes protocols having only a marginal or incomplete effect on a patient.

The term "uremic wastes" refers to a milieu of substances found in patients with end-stage renal disease, including urea, creatinine, beta-2-microglobulin.

The term "ultrafiltrate" refers to fluid that is removed from a subject by convection through a permeable membrane during hemodialysis, hemofiltration, hemodiafiltration, or peritoneal dialysis. The term "ultrafiltrate," as used herein, can also refer to the fluid in a reservoir that collects fluid volume removed from the patient, but such a reservoir may also include fluids or collections of fluids that do not originate from the subject.

The term "ultrafiltration" refers to subjecting a fluid to filtration, where the filtered material is very small; typically, the fluid comprises colloidal, dissolved solutes or very fine solid materials, and the filter is a microporous, nanoporous, or semi-permeable medium. A typical medium is a membrane. During ultrafiltration, a "filtrate" or "ultrafiltrate" that passes through the filter medium is separated from a feed fluid. In general, when transport across a membrane is predominantly diffusive as a result of a concentration driving force, the process is described herein as dialysis. When transport is primarily convective as a result of bulk flow across the membrane induced by a pressure driving force, the process is ultrafiltration or hemofiltration depending on the need for substitution solution as the membrane passes small solutes but rejects macromolecules. The term "ultrafiltration" can also refer to the fluid removal from blood during a dialysis or a hemofiltration process. That is, ultrafiltration refers to the process of passing fluid through a selective membrane, such as a dialysis or hemofiltration membrane, in either a dialysis, a hemodiafiltration, or a filtration process.

The terms "unbuffered sodium bicarbonate" and "solution of unbuffered sodium bicarbonate" refer to a sodium bicarbonate composition that is not buffered with a conjugate acid or base in any amount, proportion or pH adjusted.

The term "upstream" refers to a direction opposite to the direction of travel of a moving dialysate or other fluid within a conduit or flow path.

The term "Urea Reduction Ratio" or "URR" refers to a ratio defined by the formula below:

$$URR = \frac{U_{pre} - U_{post}}{U_{pre}} \times 100\%$$

Where:
$U_{pre}$ is the pre-dialysis urea level
$U_{post}$ is the post-dialysis urea level
Whereas the URR is formally defined as the urea reduction "ratio", in practice it is informally multiplied by 100% as shown in the formula above, and expressed as a percent.

The term "urea sensor" refers to a device for measuring or allowing for the calculation of urea content of a solution. The "urea sensor" can include devices measuring urease breakdown of urea and measurement of the resulting ammonium concentration. The sensing methods can be based on any one of conductimetric, potentiometric, thermometric, magnetoinductic, optical methods, combinations thereof and other methods known to those of skill in the art.

The term "vacuum" refers to an action that results from application of a pressure that is less than atmospheric pressure, or negative to the reference fluid or gas.

The term "vent" as referred to in relationship to a gas, refers to permitting the escape of a gas from a defined portion of the system, such as, for example, as would be found in the degassing module.

The term "void volume" refers to a specific volume that can be occupied by a fluid in a defined space such as a dialysate circuit of the invention including all components contained therein.

The terms "waste species," "waste products" and "impurity species" refers to any molecular or ionic species originating from the patient or subject, including metabolic wastes, molecular or ionic species including nitrogen or sulfur atoms, mid-weight uremic wastes and nitrogenous waste. Waste species are kept within a specific homeostasis range by individuals with a healthy renal system.

The term "waste fluid" refers to any fluid that does not have a present use in the operation of the system. Non-limiting examples of waste fluids include ultrafiltrate, or fluid volume that has been removed from a subject undergoing a treatment, and fluids that are drained or flushed from a reservoir, conduit or component of the system.

The term "water feed" refers to a source of water that is added to a dialysate flow path by means of a pump or other delivery system.

The term "water source" refers to a source from which potable or unpotable water can be obtained.

The term "water source connection" or "water feed" refers to a state of fluid communication that enables water to be obtained from a water source and connected or feed into a receiving source or flow path.

The term "within" when used in reference to a sensor or electrode located "within" the sorbent cartridge refers to all, or part of the sensor or electrode is located inside, or encased by, at least part of the inner chamber formed from the sorbent cartridge wall.

The term "working dialysate solution" refers to a dialysate solution that is undergoing active circulation or movement through a system including conduits, pathways, dialyzers and cartridges.

Measuring Dialysis

End stage renal disease (ESRD) results in a clinical condition called uremia, a toxic state resulting from accumulation in blood and tissues of solutes that are normally excreted by the kidneys. An important function of hemodialysis is to treat uremia by blood purification that removes the toxic solutes directly from the blood and indirectly from other tissues. Diffusive removal of small solutes across a semipermeable membrane by concentration gradient between blood and dialysate is the technique responsible for much of the blood purification that occurs during hemodialysis. The proportion of accumulated toxins removed from the blood and tissue by hemodialysis therapy can be used to quantify the dialysis dose. There are many solutes that accumulate at different rates in association with uremia. Medical science has not fully evaluated all of the solutes nor determined acceptable blood and tissue concentrations for each solute. Given this situation, clearance of a marker solute, urea, is commonly utilized to quantify the general dialysis dose given. Further, clearance of the marker solute, urea, has been correlated to morbidity and mortality of ESRD patients being treated by dialysis The principal waste species removed during treatment of a patient is urea that accumulates in the blood of individuals based on various degrees of kidney disease or impairment. Since urea is an electrically neutral species, a dialysate regeneration unit can convert urea to a charged ammonium species that can then be removed from the circulating dialysate within the dialysate flow loop. However, in order to maintain electrical neutrality, the removal of charged ammonium species has to be matched by exchange with another charged species, which is sodium ion in certain embodiments. As such, the concentration of sodium ions can increase over time through use of the sorbent materials and can be specifically monitored by the conductivity monitoring system.

Loss of renal function also can result in loss of the ability to balance the intake and elimination of calcium, magnesium, potassium and phosphorus that is necessary to maintain homeostasis within the tight range necessary for health. Regulation of calcium and magnesium within these tight ranges is critical to physiologic function. Altered mineral metabolism, including calcium and magnesium, contributes to bone disease, cardiovascular disease, and other clinical problems in patients with end-stage renal disease.

Disorders of mineral metabolism are independently associated with mortality and morbidity associated with cardiovascular disease and fracture in hemodialysis patients, and increased serum calcium concentration is associated with increased risk of death in hemodialysis patients. Hypermagnesemia can be manifested by hypocalcaemia, hypotension, bradycardia, osteodystrophy and bone pain, impaired cardiac contractility and intradialytic hemodynamic instability, atherosclerosis and vascular calcification, and has been demonstrated as a significant determinant, inversely correlated to serum parathyroid concentration, independent of calcium and phosphorus.

Calcium and magnesium exist in the blood in free ionized and bound forms, but it is the serum ionized form that is biologically active and integrated into the body's regulatory systems that maintain homeostasis. Although ionized serum calcium is most important, total serum calcium is typically measured for hemodialysis patients, due to the lower cost and ready availability of the test for total calcium, as opposed to serum ionized calcium. Total serum calcium measurements do not assess hypocalcaemia and hypercalcaemia as accurately as ionized serum calcium measurements and, further, methods to determine adjusted serum calcium are no more accurate than total serum calcium measurements in predicting hypo and hypercalcaemia. Further, while an individual's diet and medications may cause calcium and magnesium levels to fluctuate daily, for reasons of cost and convenience, the blood tests are typically performed only monthly.

The United States National Kidney Foundation Dialysis Outcome Quality Initiative (DOQI) has approved three measures for monitoring delivered hemodialysis dose for thrice-weekly treatment: urea reduction ratio (URR), Kt/V by urea kinetic modeling (UKM), and Kt/V by the second generation Daugirdas formula. Each measurement method utilizes, at a minimum, pre- and post-dialysis blood urea (BUN) measurements.

It will be understood by those of skill in the art that URR is a relatively simple method to quantify dialysis dose as proposed by Lowrie et al. (Lowrie E G, Lew N L. "The urea reduction ratio (URR): A simple method for evaluating hemodialysis treatment." Contemp Dial Nephrol. 1991; 12:11-20). URR is the ratio of urea removed to starting urea, calculated:

$$URR = \frac{(BUN_{pre} - BUN_{post})}{BUN_{pre}} \qquad \text{(Equation 1)}$$

where, $BUN_{pre}$—blood urea concentration at start of dialysis session $BUN_{post}$—blood urea concentration at end of dialysis session Kt/V is a dimensionless expression of the fractional clearance of urea, where, K—dialyzer clearance rate of urea (mL/min)
t—dialysis time (min)
V—volume of distribution of urea, approximately equal to patient's total body water (mL)

It will be understood by those of skill in the art that Urea Kinetic Modeling (UKM) is a complex, computer-based method of estimating urea clearance developed by Gotch and Sargent to quantify dialysis dose based on data from a National Cooperative Dialysis Study (Gotch F A, Sargent J A "A mechanistic analysis of the National Cooperative Dialysis Study (NCDS)". *Kidney int.* 1985; 28:526-34). UKM includes factors for estimated dialyzer clearance, dialysis session time, and the patient's urea distribution volume, urea generation rate, pre and post-dialysis BUN, ultrafiltration volume, interdialytic weight gain, interdialytic interval, and clearance by residual renal function. Urea distribution volume is equal to the total volume in a patient where urea is present, and is approximately equal to the volume of water in a patient. A computer is used in UKM to iteratively solve two equations until the solution converges.

A second generation Daugirdas formula calculates Kt/V from pre and post-dialysis BUN, dialysis session time, ultrafiltration volume, and post-dialysis weight (Daugirdas J T. "Second generation logarithmic estimates of single-pool variable volume Kt/V: and analysis of error." J Am Soc Nephrol. 1993; 4:1205-13).

It will be appreciated by those of skill in the art that each of the three methods approved by the United States National Kidney Foundation Dialysis Outcome Quality Initiative (DOQI) for measuring delivered hemodialysis dose require, at minimum, two measurement of the patient's blood urea concentration.

Conductivity Monitor

The present invention provides for the determination of urea content (amount or concentration) in a spent dialysate in real-time for determination of adequacy or efficiency of dialysis therapy including but not limited to hemodialysis and hemodiafiltration, and also ultrafiltration. In particular, the invention is directed toward a conductivity monitor that can operate with a dialysate regeneration unit to perform dialysis with a limited volume of dialysate. In any embodiment, a working dialysate fluid can be circulated in a dialysis flow loop between a dialyzer and a dialysate regeneration unit, certain embodiments of which include a dialysate regeneration cartridge. Spent dialysate containing at least one waste species elutes from an outlet of the dialyzer during treatment where the spent dialysate is passed through the dialysate regeneration unit where waste species including urea are removed from the dialysate. Using the dialysate regeneration unit, the working dialysate can be regenerated for recirculation through the dialyzer by the removal of waste species and the re-addition and/or re-constitution of species needed for a biocompatible dialysate, such as buffers, calcium ions, potassium ions, magnesium ions and other components typically employed for dialysate solutions. The conductivity monitor operating with systems and methods can also provide inputs for the monitoring of sodium ion concentration and/or conductivity of the dialysate and operate with a means to add a sodium-modified fluid or other infusates to the dialysate flow loop when needed to adjust conductivity or electrolyte concentration.

Blood circulating through a dialyzer via an extracorporeal circuit exchanges waste components with dialysate circulating through the dialyzer and dialysate flow loop. Waste species including ions and uremic toxins, such as uric acid, creatinine, and β2-microglobin, and urea diffuse from the blood to the dialysate within the dialyzer via a semipermeable membrane contained therein. As such, the limited volume of dialysate within the dialysate flow loop can reach equilibrium with the content of waste species in the blood without ongoing removal of waste species from the dialysate to maintain a concentration gradient of waste species between the blood and the dialysate within the dialysate flow loop. During treatment employing the dialysate regeneration unit, the urea content of the spent dialysate will normally be less than the actual urea content of the blood due to on-going removal of urea from the dialysate as part of dialysate regeneration. The urea concentration difference between the blood and the dialysate depends on several factors (e.g. point in treatment, flow rates, dialyzer efficiency, etc.) such that urea content of the blood cannot be readily determined solely through measurement of real-time concentration of urea in the dialysate.

The sensing components, systems and methods of the invention can provide real-time information regarding cleared solutes within the dialysate stream that can be applied to detect and measure these factors so that corrective action can be taken within the dialysis session or between dialysis sessions to ensure that the dialysis session clearance goals are met. Dialysis standards of care are used to establish specific session clearance goals (Kt/V) that are to be achieved by hemodialysis treatment. The invention can also demonstrate and document that a prescribed clearance, Kt/V, has been achieved by the dialysis therapy provided. The present invention can also provide for urea Kt to be measured directly such that clearance is documented in the medical record. Similarly, measurements of urea reduction ratio (URR) and equilibrated Kt/V (eKt/V) are also documented.

Many factors can compromise the effective clearance achieved during a dialysis session such that clearance, Kt/V, differs from what would be predicted by the configuration of the dialyzer, dialysis and blood flow rates, etc. Factors include blood access recirculation, access connection errors, dialyzer clotting, blood flow errors, dialysis session interruptions, and dialyzer variability. However, in any embodiment, the sensing methods of the present invention can provide real-time information regarding cleared solutes within the dialysate stream that can be applied to detect and measure these factors so that corrective action can be taken within the dialysis session or between dialysis sessions to ensure that the dialysis session clearance goals are met.

In any embodiment, a dialysate regeneration cartridge, such as a sorbent cartridge, can contain several materials and/or sorbents that are capable of removing solutes from the dialysate including: urea, phosphate, calcium, magnesium, potassium, creatinine, uric acid, beta-2-microglobulin and sulfate. The regeneration cartridge can also contain components or materials that release or bind sodium during the process of removing solutes from the dialysate. For example, the dialysate regeneration cartridge can be a sorbent cartridge containing activated carbon, urease, zirconium phosphate and hydrous zirconium oxides. In particular, a urease-containing material can convert neutral urea to an ammonium salt that affects the conductivity of the dialysate and allows for ammonium, and hence nitrogen, to be removed by cation exchange with other sorbent materials. In certain embodiments, the urease-material and sorbent materials can be contained in a single housing. In other embodiments, the urease-material and sorbent materials can be contained in multiple housings including two or more housings.

In some embodiments, a conductivity monitoring system is provided for measuring the conductivity change in the dialysate affected by specific sorbent and/or urease-containing materials individually or in combination. For example, the conductivity monitoring system can measure the change in conductivity of spent dialysate prior to contact with the urease-containing material and after completing contact with the urease-containing materials. As such, the change in conductivity caused by the conversion of urea to ammonium salts can be determined prior to downstream contact with other materials that may further affect conductivity. In other embodiments, the conductivity monitoring system can measure the change in conductivity affected by non-urease containing materials to evaluate the effectiveness and performance of sorbent materials.

Regeneration of the dialysate within the dialysate flow loop can be achieved through contacting the dialysate with sorbents contained within the dialysate generation unit. Examples of useful sorbent materials include the REDY sorbent system and U.S. Pat. Nos. 3,669,880; 3,989,622; 4,581,141; 4,460,555; 4,650,587; 3,850,835; 6,627,164; 6,818,196; and 7,566,432 and U.S. Patent Publications 2010/007838; 2010/0084330; and 2010/0078381 and International Patent Publication WO 2009/157877 A1, which are incorporated herein by reference. In some embodiments, the dialysate regeneration unit with one or more sorbent cartridges can contain one or more materials selected from the group consisting of: 1) a urease-containing material, where urease is an enzyme that catalyzes the conversion of urea to ammonium ions and carbon dioxide; 2) a zirconium phosphate (ZrP) material that has the capacity to act as a cation exchanger by absorbing a large quantity of ammonium ions in exchange for sodium and hydrogen ions; 3) a zirconium oxide material (ZrO), which acts as an anion exchanger by exchanging phosphate for acetate; and 4) an activated carbon material that has a surface area for adsorption of wide range of impurities including metal ions and uremic toxins, such as uric acid, creatinine, and β2-microglobin. The term zirconium oxide is used interchangeably with the term hydrous zirconium oxide. In some embodiments, the zirconium phosphate material can be replaced with a magnesium phosphate material.

In some embodiments, the urease and/or sorbent materials used for dialysate regeneration include a layer of urease and alumina that converts urea in spent dialysate into ammonium, which changes the conductivity of the dialysate fluid as the fluid flows through a dialysate regeneration unit. The difference in conductivity measured in the dialysate pre- and post-contact with a urease-containing material is correlated to the amount of urea removed during hemodialysis therapy.

The methods disclosed make use of solution conductivity increase that occurs as a result of the ionic byproducts of catalytic hydrolysis of urea by the enzyme urease according to Scheme 1.

(Scheme 1)

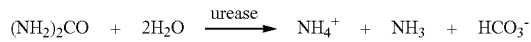

In some embodiments, a single conductivity meter or detector can measure multiple flow streams, where each flow stream represents the spent dialysate contacted with a different combination of urease-containing materials and/or sorbents, or the spent dialysate prior to any contact with urease-containing materials and/or sorbents. As such, calibration, temperature, electronic drift and other errors between separate conductivity meters can be reduced or eliminated. The ability to monitor conductivity changes affected by different combinations of urease-containing materials and/or sorbents allows for the performance or efficiency of various system components to be evaluated as well as the determination of the amount of urease in the dialysate.

In certain embodiments, the urease-containing material and additional sorbent materials are interdispersed within the same housing. The performance of conversion of urea to ammonia can be monitored and determined by intermittently providing a bolus of a sodium chloride solution to the dialysate regeneration cartridge such that the urea content of spent dialysate entering the regeneration cartridge can be determined. In certain embodiments, an equilibration bypass is provided to allow for the dialysate within the dialysate flow loop to come into equilibration with the urea concentration of the blood in contact with the dialyzer. After equilibration, the conductivity monitoring system can determine the urea content of the equilibrated dialysate, which reflects the urea content of the blood.

In certain embodiments, the components of the dialysate flow loop can have a controlled compliant volume. As such, fluid is in passive equilibrium and does not provide for net flow from the extracorporeal circuit to the dialysate flow loop due to the controlled compliant volume of the dialysate loop. The net balance of fluid is prevented from passively flowing between the flow loop to the extracorporeal circuit via the dialyzer since such a movement of fluid will leave a vacuum in the flow loop or require the flow loop to expand. Since the dialyzer can be a high-flux type that readily allows for the passage of water, there is some fluid flux back and forth across the dialyzer membrane due to the pressure differential on the blood and dialysate sides of the membrane. This is a localized phenomenon due to the low pressure required to move solution across the membrane and is called backfiltration; however, this results in no net fluid gain or loss by the patient.

The components forming the dialysate flow loop of the invention can have a controlled compliant volume wherein the dialysate flow loop further incorporates a control or ultrafiltration pump that can be operated bi-directionally to cause the net movement of fluid from an extracorporeal side of the dialyzer into the dialysis flow loop or to cause net movement of fluid from the dialysate flow loop into the extracorporeal side of the dialyzer. In particular, a control or ultrafiltration pump is operated in the efflux direction to cause the movement of fluid from the extracorporeal side of the dialyzer into the dialysis flow loop and in the influx direction to cause the movement of fluid from the dialysis flow loop into the extracorporeal side of the dialyzer. The action of typical pumps contemplated by the invention function by expanding or contracting a space wherein any suitable type of pump can be used in the present invention.

In certain embodiments, operation of the control or ultrafiltration pump in the influx direction can be substituted with operation of the infusate pump to drive liquid from the infusate reservoir into the dialysis flow loop and subsequently cause movement of fluid from the dialysis flow loop to the extracorporeal side of the dialyzer. The control or ultrafiltration pump can also be used for the movement of fluid in the opposite direction across the dialyzer into the dialysis flow loop. It is noted that the infusate reservoir or ultrafiltrate reservoir can allow the system to adjust the patient fluid volume by withdrawing fluid and storing the desired amount in the respective reservoir and/or by providing rebalanced fluids to the patient and removing waste products. For example, the fluid stored in a control reservoir attached to the dialysate circuit can be used to store a volume of fluid equal to the ultrafiltrate volume removed from the patient during ultrafiltration (UF). Alternatively, the fluid stored in the control reservoir can be an infusate delivered to the patient. In certain embodiments, the delivered fluid can contain a therapeutic component deliverable across the dialyzer and into the patient's bloodstream. Additionally, the volume of the dialysate flow loop can be actively controlled by the user or a programmed controller.

The control or ultrafiltration pump allows for fluid to move from the dialysate flow loop to the extracorporeal side without creating a vacuum, wherein the operation of the control pump is controlled as described herein. Likewise, the control pump allows for fluid to move from the extracorporeal side, and hence the patient's body via the action of the control pump. Movement of fluid between the extracorporeal side of the dialyzer and the dialysate flow loop can be accurately controlled and metered using the removed fluid in certain embodiments. In other embodiments, the removed fluid can be transferred back to the patient through the dialysate flow loop using the ultrafiltrate stored in ultrafiltration reservoir. In some embodiments, the ultrafiltration reservoir can be prefilled with water, dialysate or other fluid for addition to the dialysate flow loop and/or for use or treatment within the sodium control system.

As such, some embodiments have a controlled compliant dialysate flow loop that can be accurately controlled to precisely remove or add fluid to the extracorporeal side of the dialyzer. Due to the substantially inflexible void volume of the conduits, the dialysate regeneration unit and other components of the dialysate flow loop, the net movement of fluid over any time interval across the dialysate membrane within the dialyzer can be accurately controlled by creating a means to accurately introduce or remove fluid from the patient. This capability can further be used to enhance the convective clearance of the system for uremic impurities while controlling the net fluid removed from the patient, for example, creating periods of fluid movement across the membrane with occasional reversal of direction. In certain embodiments, an ultrafiltrate can be used as described herein. However, the present invention is not limited to a controlled compliant flow path. As such, the dialysate flow loop in certain embodiments is not a controlled compliant flow path and may include one or more open reservoir for storing or accumulating dialysate.

In certain embodiments, a control pump can be a peristaltic pump, a volumetric metering pump, diaphragm pump, or a syringe style pump. Hence, the dialysate flow loop has a substantially inflexible volume except for controlled changes in volume modulated by the control or ultrafiltration pump, the infusion pump and optionally any other pumps that add fluid to the dialysate flow loop. The contents of U.S. patent application Ser. No. 13/565,733 filed on Aug. 2, 2012 are incorporated herein by references in their totality.

In certain embodiments, the dialysate flow loop has a void volume from about 0.15 L to about 0.5 L. In other embodiments, the dialysate flow loop has a void volume from about 0.2 L to about 0.4 L or from 0.2 L to about 0.35 L. Other volumes can be envisioned by those of ordinary skill in the art depending on parameters such as patient weight, size, and health condition. The system can be designed to be a portable system, a desktop system or a large system suitable for heavy use in a clinical setting. Hence, both large volumes greater than 0.5 L to about 5 L, and micro-volumes from as small as 0.1 L to about 0.5 L such as 0.1 L to 0.2 L, 0.1 L to 0.3 L, 0.1 L to 0.4 L, 0.2 L to 0.3 L, 0.3 L to 0.4 L, or 0.3 L to 0.5 L are contemplated by the invention.

Figure 11:
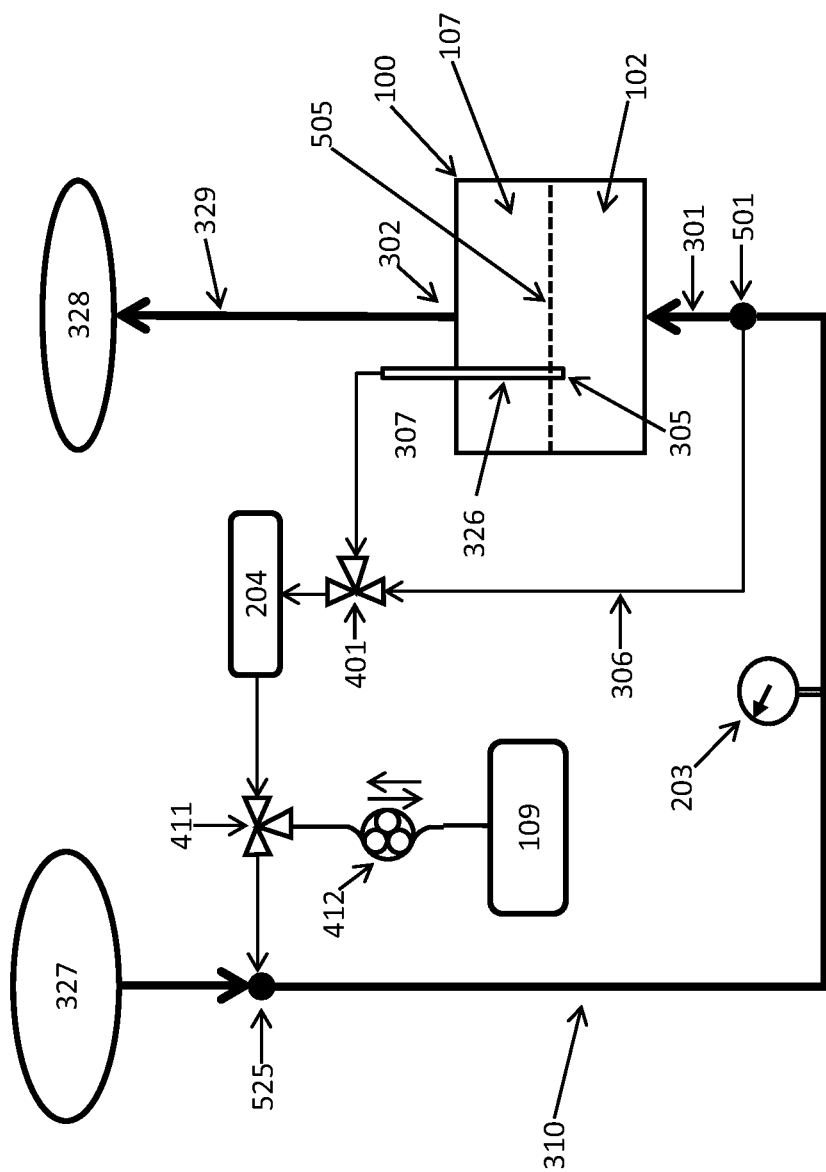
FIG. 11 shows a dialysate regeneration unit having a dialysate conductivity sensor in fluid communication with multiple sampling flow streams operating for use in hemofiltration.

Exemplary dialysate flow loops are described in more detail below including in relation to FIGS. 7, 8 and 11. A dialysate flow loop has a dialysate flow path 320 and post-dialyzer flow path 310 for transporting a dialysate between a dialyzer 318 and a dialysate regeneration cartridge or system 100. A bypass loop 308 can be present to allow for the diversion of a portion of the dialysate around the dialyzer 318 to rejoin the flow path in the post-dialyzer 310 flow path. One or more infusates can be added by an infusate injector 313, which can be present to add an infusate to either the dialysate flow path 320 or post-dialyzer 310 flow paths. Similarly, a buffer pump or source solution 311 can be present for addition to the dialysate flow loop and/or a pump or source for adding fresh water/dialysate 323. Fresh water/dialysate 323 can be added to the dialysate flow loop as a diluent to decrease the conductivity or sodium chloride content of the circulating dialysate. An ultrafiltration or control pump can also be present to add or remove volume from the dialysate flow loop (not shown). Where dilution of the sodium concentration or conductivity of the dialysate is needed, water from fresh water or dialysate source 323 can be added to the dialysate flow loop and dialysate removed from the dialysate flow loop using the control pump. The control pump can also be used to affect ultrafiltration of the blood by drawing fluid out of the blood through the membrane of the dialyzer 318 and/or the control pump can be used to add volume to the dialysate flow loop to counter hemoconcentration within the dialyzer 318.

The systems and methods disclosed herein can be broadly applied to dialysis equipment and be used in a blood based solute monitoring system. A critical principle utilized by the blood based solute monitoring system is that a small volume of dialysate can be recirculated through the dialyzer multiple times in a short period of time to equilibrate a dialysate solute concentration to a blood solute concentration on the blood side of a dialyzer in order to obtain certain measurements of patient blood solute concentration. In some embodiments a small void volume dialysate loop with sorbent based regeneration and fluid circulating in a closed loop can take advantage of this critical principle. However, a sorbent is not necessarily required as part of the present system where dialysate is recirculated. In other embodiments, addition of a small volume recirculating dialysate loop to a sorbent regenerative dialysis system having an open reservoir, such as a REDY system, can make these systems capable of utilizing this principle. In certain embodiments, a small recirculating loop and a miniature sorbent column can be added to a standard single pass dialysate system to enable this type of system to be able to utilize the measurement principles disclosed. In any embodiment, the dialysate flow rate can be increased or the volume of the dialysate loop decreased to reduce the equilibration time. In certain embodiments, a measurement can be taken by the present blood based solute monitoring system without a second flow path that is not equilibrated with blood on the blood side of a dialyzer. In other embodiments, the present blood based solute monitoring system can be in fluid communication with a sorbent regenerated dialysate loop, or a controlled compliant loop. In still further configurations, a small volume recirculation loop with a control valve could be installed in a traditional single pass system to take advantage of the principles discussed herein. For example, the small volume recirculation loop can be installed and in fluid communication with a REDY type system or a REDY open reservoir type system.

One of ordinary skill will understand that many systems known within the art can advantageously employ a small recirculating volume to equilibrate the solute concentration quickly across a dialyzer. Because the circulating volume in a recirculating flow path is sufficiently small, the system can pump in a short period of time the necessary volume of fluid to recirculate the fluid through the dialyzer a sufficient number of times to equilibrate the concentration of solutes in the dialysate to the concentration of solutes in the blood. One or more pumps can be configured in the system to reduce equilibration times or to cause fluid flows through specific fluid paths.

In certain embodiments, the small recirculating volume can be configured into a controlled compliant flow path as described herein to reduce equilibration time and/or be configured to be in fluid communication with a dialysate flow path that is also controlled compliant. However, it will be understood that the present recirculating loop having small, quickly equilibriated volumes can be configured to be in fluid communication with any dialysis machine or therapy device using combinations of tubing, one or more valves, and one or more sensors. A theoretical minimum volume for use in the blood based solute monitoring system can be a priming volume of the dialysate compartment of the dialyzer.

Various sensor types can be used to detect the chemical changes occurring as the dialysate flows through the various sorbent layers. Chemical sensing that operates by fluid conductivity measurement with a conductivity meter can be used. In any embodiment, ion selective membranes can be applied to the conductivity electrodes by techniques that are known in the art and commercially available, in order to measure pH, or other ion species such as sodium and potassium. In some embodiments, additional sensors for measuring pH, temperature, and pressure can be added to one or more flow paths containing the conductivity meter to enhance the measurement accuracy and specificity. The blood based solute monitoring system requires at least one measurement. For example, an ion selective sensor such as a potassium sensor can be used wherein only a single sensor is required and a single measurement is taken to determine the equilibrated dialysate concentration, and thus the blood concentration. Similarly, a single sensor reading from an ammonium ion sensor located post-urease can be used to measure BUN. For determining both conductivity and/or a pH-based measurement, at least 2 sensors or 2 fluid samples both before and after fluid has passed urease are required to obtain BUN. In certain embodiments, the blood based solute monitoring system need not rely solely on equilibration but can utilize an electrolyte bolus to perform the measurement of the blood solute concentration. For example, a bolus is provided between the dialyzer outlet and the sorbent inlet. As shown in the non-limiting, embodiment of FIG. 8, three sample points and a bolus injector are located between the outlet of the sorbent and the inlet of the dialyzer.

In any embodiment, the conductivity monitor of the present invention can be used to measure urea concentration in the dialysate, further enabling the determination of blood urea concentration, for example at the beginning and at the end of a dialysis session, at intermediate time points during a dialysis session, at a specific time after the end of a dialysis session (to measure rebound of urea, or other solutes, to determine equilibrated clearance, or eKt), or for determination of protein catabolic rate (PCR), a nutritional marker derived from interdialytic urea accumulation that can be important in determining the dialysis prescription.

In any embodiment, measurement of the urea concentration in the dialysate can further be used to monitor the time course of urea concentration decrease, effective dialysance, for deviations that may indicate deficiencies related to blood access recirculation, access connection errors, blood flow inaccuracy, or dialyzer clotting that requires intervention within the dialysis session to ensure therapy targets are met. In some embodiments, measurement of the urea concentration in the dialysate can further be used to determine total urea mass clearance for a dialysis session by multiplying urea concentration by dialysate flow rate and integrating over dialysis session time to obtain the urea Kt.

FIG. 1 shows a dialysate regeneration cartridge 100 in accordance with certain embodiments of the invention. The dialysate regeneration cartridge 100 can include a urease material segment or layer in sequence with one or more sorbent materials. For example, the sorbent cartridge 100 illustrated in FIG. 1 includes a segment or layer containing the enzyme urease and alumina 102, a zirconium phosphate segment or layer 103, a zirconium oxide segment or layer 104, and an activated carbon segment or layer 105. In any embodiment, the urease material 102 can also include alumina. Spent dialysate containing blood impurities, such as urea, enters the sorbent cartridge 100 through inlet stream 301, passes through the urease material 102 and the sorbent materials, and regenerated or partially regenerated dialysate exits the sorbent cartridge 100 through outlet stream 302. The sorbent materials remove the impurities from the dialysate, and the dialysate returns to the dialyzer through the sorbent outlet stream 302.

Urea can be converted to ammonium carbonate as the dialysate passes through the urease layer 102, according to Scheme 1 as described herein. As the solution passes through the urease layer 102, ammonium and bicarbonate ions produced by this reaction can result in an increase in dialysate solution conductivity proportional to the concentration of urea in the dialysate stream entering the regeneration cartridge 100 through inlet stream 301.

The dialysate regeneration cartridge 100 of FIG. 1 can be associated with a pre-urease conductivity measurement point 201 upstream from the urease material 102 in the dialysate flow loop between a dialyzer outlet and the sorbent inlet stream 301, and an integral post-urease conductivity measurement point 202 downstream of the urease material 102. A measurement point refers to a position in a flow path or sorbent cartridge that is in fluid communication with a sensor. The sensor can be in fluid communication at a particular position, or measurement point, by being physically located at the position of interest, or located away from the position of interest and have a fluid stream from the position of interest conveyed to the sensor. Conveyance of the fluid stream can occur via flow paths. In any embodiment, the post-urease measurement point can be located downstream from the sorbent outlet stream 302 between any stage or stages of the regeneration cartridge 100 and a dialyzer inlet. In any embodiment, a controller, such as a digital processor, can monitor the conductivity measurements taken at the conductivity measurement points 201 and 202. The controller can further perform calculations using the conductivity measurements and/or additional measurements, such as the dialysis flow rate taken at the dialysate flow sensor 203, for example, to determine the amount of urea removed by the urease material 102 over time. The difference between the conductivity measurements at conductivity measurement points 202 and 201 can be used to determine the urea concentration of the spent dialysate entering the sorbent cartridge 101 through the inlet stream 301. The urea concentration can further be multiplied by the dialysate flow rate as measured by flow sensor 203 to determine the urea mass flow rate cleared by the dialyzer.

Figure 2:
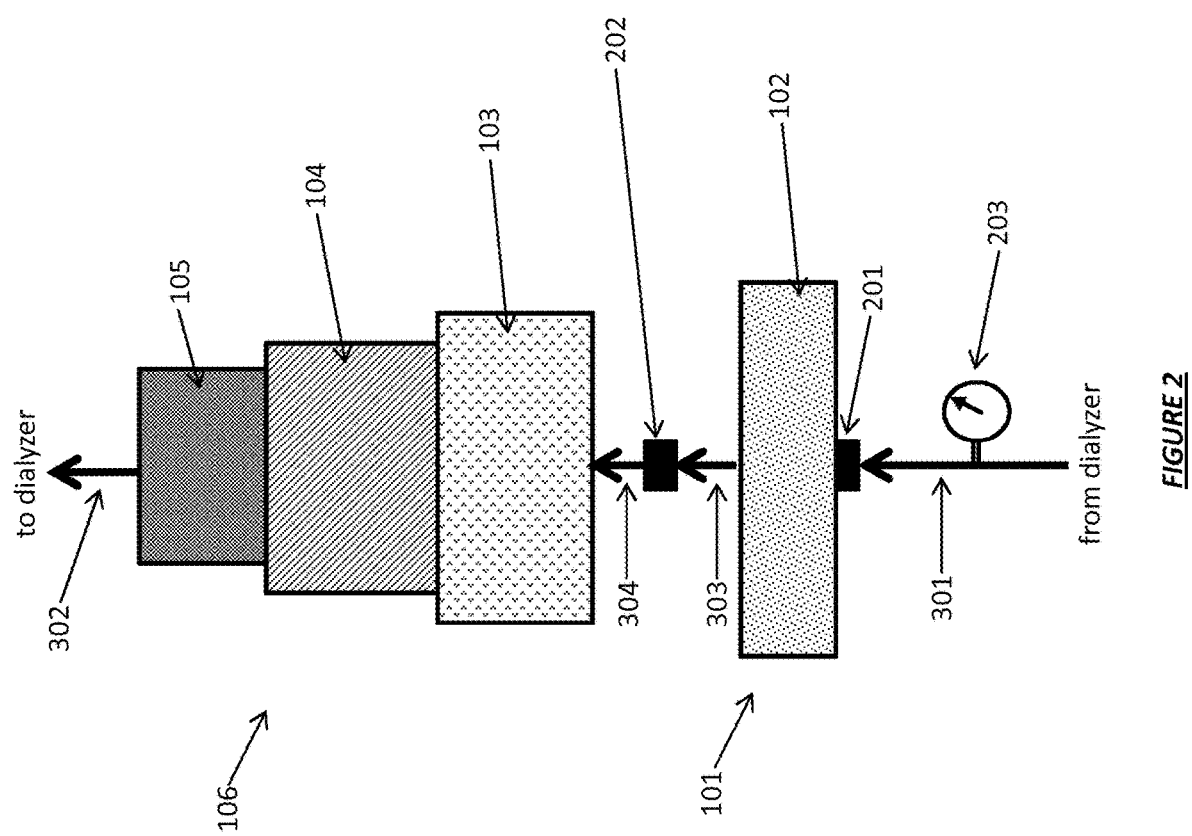
FIG. 2 shows a dialysate regeneration unit having dialysate conductivity sensors operating in accordance with certain embodiments.

FIG. 2 shows a dialysate regeneration unit that can include a urease housing 101 that contains the urease material 102 and a separate sorbent housing 106 that can contain one or more sorbent material segments or layers, for example, the zirconium phosphate segment or layer 103, the zirconium oxide segment or layer 104, and the activated carbon segment or layer 105. Spent dialysate enters the urease housing 101 through the sorbent cartridge inlet stream 301, passes through the urease material 102 and exits the urease housing 101 through the urease housing outlet stream 303, then enters the sorbent housing 106 through the sorbent housing inlet stream 304 and passes through the sorbent materials 103, 104, 105 before exiting the sorbent housing 106 by way of the sorbent cartridge outlet stream 302 as regenerated or partially regenerated dialysate.

The dialysate regeneration unit of FIG. 2 can be further associated with a pre-urease conductivity measurement point 201 upstream of the urease housing 101 and a post-urease conductivity measurement point 202 downstream of the urease housing 101 and upstream of the sorbent housing 106. In some embodiments, conductivity measurement point 202 is external to the urease housing 101 and the sorbent housing 106, which can have advantages in certain applications. For example, having the conductivity measurement point external to the sorbent cartridge can simplify placement of a conductivity sensor directly at the measurement point or simplify incorporation of a flow path used to convey a fluid stream to a sensor positioned at a location different than the measurement point. In some embodiments, sorbent housing 106 can include multiple layers of individual sorbent materials. In other embodiments, sorbent housing 106 can contain multiple sorbent materials that are blended together to form a single, uniformly mixed layer. Additional embodiments can include multiple sorbent cartridge housings that each contain an individual sorbent material. As described in FIG. 1, a controller can monitor the conductivity measurements taken from the conductivity measurement points 201 and 202, and in any embodiment the dialysate flow sensor 203 can measure the flow rate of the dialysate, which can be used in further computations.

FIGS. 1 and 2 show exemplary embodiments of dialysate regeneration units and are not exclusive. Other types of sorbent materials and other sequences of materials can be provided.

Conductivity Monitoring System

Figure 3:
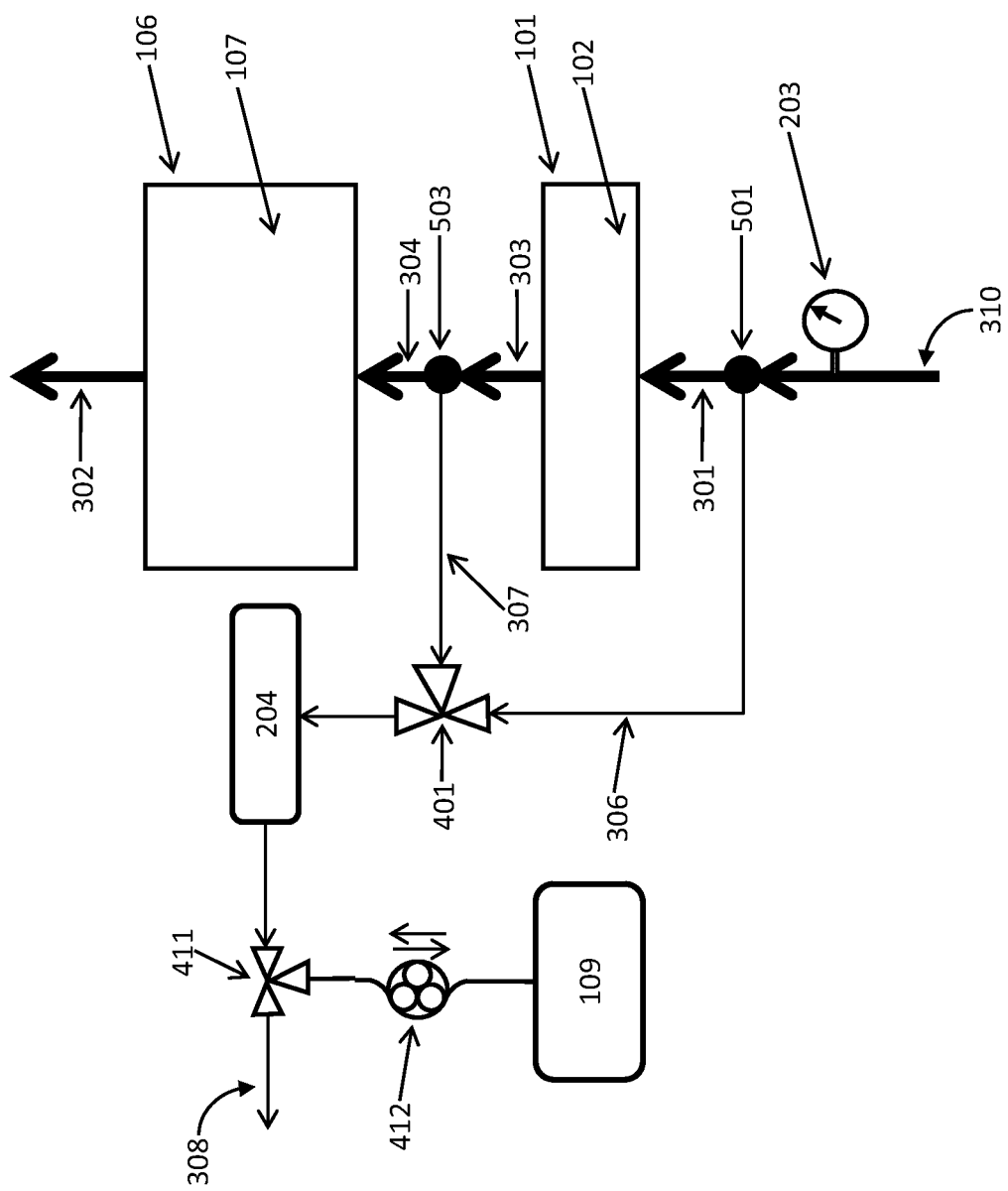
FIG. 3 shows a dialysate regeneration unit having a dialysate conductivity sensor in fluid communication with multiple sampling flow streams operating in accordance with certain embodiments.

FIG. 3 shows a dialysate regeneration unit or device that can include a urease housing 101 containing, for example, a urease material 102 and a sorbent housing 106 containing, for example, one or more sorbent materials or other regenerative materials 107 to remove waste species from the dialysate, such as the sorbent cartridge shown in FIG. 2. In some embodiments, the urease housing 101 and the sorbent housing 106 can be integral to a single unit, such as an interchangeable sorbent cartridge, whereas in other embodiments the urease housing 101 and the sorbent housing 106 can be separate and independent units. Post-dialyzer dialysate, or spent dialysate, can enter the urease housing 101 through the sorbent cartridge inlet stream 301, pass through the urease material 102 and exit the urease housing 101 through urease housing outlet stream 303 before entering the sorbent housing 106 through sorbent housing inlet stream 304, passing through one or more layers of sorbents and/or other regenerative materials 107 in sorbent housing 106 and exiting the sorbent housing 106 through the sorbent cartridge outlet stream 302. Within the sorbent housing, there may be multiple sub-layers of materials of different sorbent compositions, such as illustrated and described for FIGS. 1 and 2.

The dialysate regeneration unit or device can further include a conductivity monitoring system having a single conductivity meter 204 and a sampling valve 401, such as a three-way valve shown in FIG. 3, capable of selecting between two separate sample streams 306 or 307 that are drawn from the junction points 501 or 503, respectively. The single conductivity meter 204 may alternatively be referred to as "single conductivity sensor 204", "common conductivity meter 204", or "common conductivity sensor 204." The junction points 501 and 503 allow dialysate fluid to flow towards conductivity meter 204, depending on the position of sampling valve 401. The junction points 501 and 503 could consist of a 3-way tee-connector. One of ordinary skill in the art will recognize that junction points 501 and 503 can also include two-way valves, which could replace the three-way valve and provide equivalent functionality for any of the sampling valves described herein. In some embodiments the sample streams 306 and 307 can convey a continuous flow of dialysate from the selected flow streams 306 or 307, while in other embodiments the sample streams 306 and 307 can convey an intermittent flow of dialysate.

In any embodiment of the invention, sampling can be accomplished using tubing or a flow conduit external to or integral to the urease housing 101 and sorbent housing 106. The first sample stream 306 can be drawn from the post-dialyzer dialysate flow stream 310 upstream of the sorbent cartridge inlet stream 301 before the urease has hydrolyzed the urea into ionic byproducts, and the second sample stream 307 can be drawn from the dialysate flow downstream of the urease housing outlet 303. In some embodiments, each sample stream can convey a small fraction of the main dialysate flow stream. The sampling valve 401 can be placed in a closed position to inhibit flow through both sample streams 306 and 307 and allow dialysate to flow through the urease and sorbent housings 101 and 106 without any sampling.

In order to measure the reduction in the urea concentration of the dialysate when it passes through the urease 102 using the conductivity monitoring system, the sampling valve 401 can be intermittently toggled between a first intake position and a second intake position. When sampling valve 401 is placed in the first intake position, sample stream 306 delivers dialysate to the sampling valve 401 prior to entering the urease housing 101 and/or contacting the urease layer 102; the first sample stream 306 conveys post-dialyzer dialysate from junction point 501, which contains urea that has not yet been converted into ammonium ion species. Dialysate in sample stream 306 can be passed through the sampling valve 401 to a conductivity meter 204 and a first conductivity measurement is obtained from the post-dialyzer dialysate before urea is hydrolyzed into ionic by-products.

When first sampling valve 401 is placed in the second intake position, sample stream 307 is delivered to the sampling valve 401 and subsequently to the conductivity meter 204. The second sample stream 307 can be drawn from the dialysate flow after the dialysate has contacted the urease layer 102 but before the dialysate has contacted any downstream layers within the sorbent housing 106. More specifically, the second sample stream 307 is sampled from junction point 503 after contact with the urease layer 102 has been completed and the conversion from urea to ammonium salt is substantially complete. In some embodiments, sample stream 307 can be taken from a position at the interior of an integral sorbent cartridge. For example, sample stream 307 may result from a tube inserted part-way into the sorbent cartridge and in fluid communication with the dialysate flowing through the sorbent cartridge at a point near the urease housing outlet stream 303. In certain embodiments sample stream 307 can be drawn from a junction point between separate and independent urease and sorbent housings 101 and 106.

A second conductivity measurement can be taken by conductivity meter 204 using the second sample stream 307. Dialysate in sample stream 307 can be passed through the sampling valve 401 to a conductivity meter 204 and a second conductivity measurement can be obtained for the dialysate after some or all of the urea has been hydrolyzed into ionic byproducts.

In any embodiment, sampling valve 401 can be periodically alternated between the first sample flow stream 306 and the second sample flow stream 307 and alternating conductivity measurements can be taken by the conductivity meter 204 corresponding to the two sample streams 306 and 307 to measure the reduction in the urea concentration of the dialysate affected by the urease material 102. The period of time for performing the conductivity readings in various, non-limiting embodiments can be less than 5 minutes, less than 3 minutes, less than 1 minute, less than 45 seconds, less than 30 seconds or less than 15 seconds depending on each separate conductivity measurement. However, it will be understood that any period of time is contemplated by the present invention. In certain embodiments, the sampling valve 401 can remain in a fixed position until a conductivity reading taken by the conductivity meter 204 stabilizes to an acceptable level of drift, rather than remaining in a certain position for a fixed period of time.

The reduction in the concentration of urea in the dialysate resulting from the removal of urea as the dialysate passes through the urease material 102 can be determined by comparing the conductivity reading from sample stream 307 and the conductivity reading from sample stream 306. The monitoring of urea concentration or amount in the dialysate can be monitored in a real-time manner during the period where the sampling valve 401 is actively toggled between sample stream 306 and 307. Alternatively, the sampling valve 401 can periodically be placed in the closed position and conductivity measurements can be intermittently taken to determine the urea content of the dialysate on an intermittent basis.

In addition, any embodiment of the invention can include a dialysate flow sensor 203 to measure the rate of flow of the dialysate passing through the dialysate regeneration unit or device. In certain embodiments, the dialysate flow sensor 203 can be located along flow stream 310 to measure the flow rate of dialysate through the dialysate regeneration cartridge 100 or urease housing 101. The measured flow rate of dialysate through the regeneration cartridge 100 or urease housing 101 can be used to calculate additional data, for example, in combination with the conductivity readings to quantify the amount of urea removed from the dialysate by the dialysate regeneration cartridge 100 or urease housing 101 during a specified period of time.

After a conductivity reading is taken at conductivity meter 204, the sample stream exiting conductivity meter 204 can be diverted to the bypass loop 308 and rejoined with the working dialysate solution in the dialysate flow loop at a position downstream from the dialyzer and upstream from the dialysate regeneration unit or device. Since a single conductivity meter 204 is used to measure the conductivity of both the first and the second sample streams 306 and 307, offset slope and drift errors that may occur when comparing measurements taken by two separate sensors can be eliminated. Further, in certain embodiments thermal differences between the first and second sample streams 306 and 307 can be minimized by co-routing and/or insulating the corresponding conduits. In any embodiment, the conductivity meter 204 can be fluid temperature compensated by having a thermocouple contained in the conductivity meter, or in close proximity.

Figure 4:
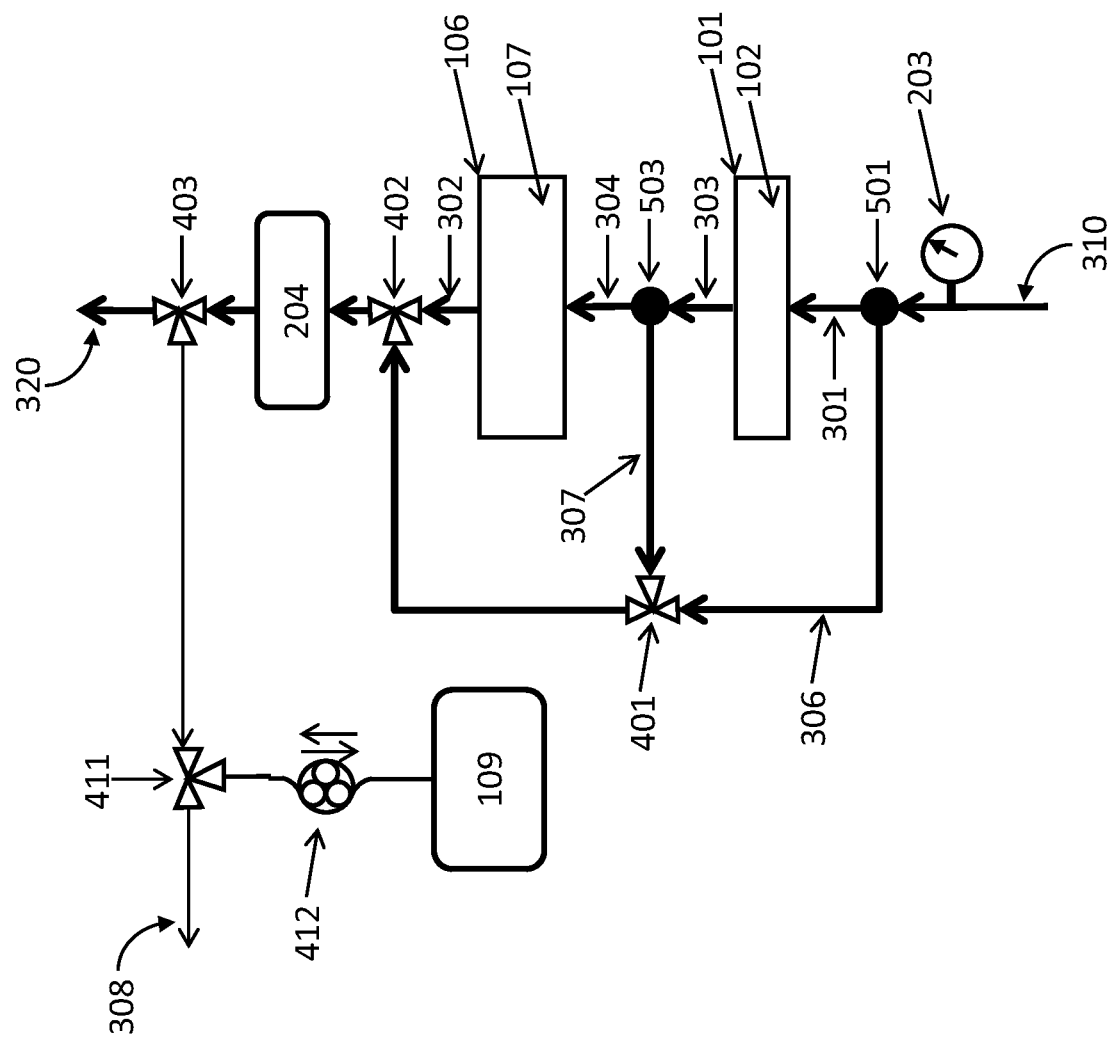
FIG. 4 shows a dialysate regeneration unit having multiple regeneration segment bypass conduits and a conductivity sensor operating in accordance with certain embodiments.

In the embodiment shown in FIG. 3, the conductivity meter 204 is configured to take a conductivity measurement from two separate sample flow streams, where each flow stream represents a stream having a different degree of contact or modification by the dialysate regeneration unit or device. In FIG. 4, a dialysate regeneration device is shown that is capable of measuring three different flow streams 306, 307 and 302 using one shared conductivity meter 204.

As described in FIG. 3, the first sample stream 306 consists of dialysate prior to contact with the urease-containing layer 102 contained in the urease housing 101. The second sample stream 307 consists of dialysate after contact with the urease-containing layer 102 contained in the urease housing 101. FIG. 4 shows an additional embodiment where a conductivity measurement can be taken from the sorbent housing outlet flow stream 302 consisting of dialysate that has passed through all layers of the dialysate regeneration unit, including the urease-containing layer 102 and the other sorbent materials 107 contained in sorbent housing 106.

In any embodiment an optional sample return buffer reservoir 109 as shown in FIGS. 3-15 can temporarily store the sample fluid before it is returned to the main dialysate flow loop via bypass loop 308, in order to prevent returned sample fluid from modifying the composition of fluid in the main dialysate flow loop while a conductivity reading is being taken. An optional buffer pump 412 can be operated in conjunction with sampling valve 411 to either transfer fluid exiting the conductivity meter 204 into the sample return buffer reservoir 109, or to transfer fluid from the sample return buffer reservoir 109 to the main fluid loop via bypass loop 308. In some embodiments, the buffer pump 412 can also function as an ultrafiltration or fluid balance control pump and the sample return buffer reservoir 109 can also serve as an ultrafiltrate or fluid balance control reservoir.

As shown in FIG. 4, the sampling valve 401 can be alternated between a closed position and first and second sampling positions to select the first 306 or second 307 flow stream, as described above. In the closed position, dialysate is prevented from entering the conduits forming the first 306 and second 307 flow paths.

A common conductivity meter 204 can intermittently measure the conductivity from all three sample streams 306, 307 and 302, as such, errors that can result from calibration differences between separate conductivity meters are eliminated. In addition to measuring urea removal by comparing conductivity differences between pre- and post-urease sample streams 306 and 307, the conductivity meter 204 can also monitor performance of the sorbents within sorbent housing 106 by comparing conductivity measurements of dialysate fluid from flow stream 302 exiting the sorbent housing 106 with conductivity measurements from the dialysate fluid taken through the second sampling conduit 307 before it has entered the sorbent housing 106 through sorbent housing inlet 304. That is, conductivity of the second sample stream 307 can be compared to the conductivity of dialysate flow stream 302 to determine performance of the materials within the sorbent housing 106. Further, the conductivity of the dialysate flow stream 302 can indicate the actual conductivity of the dialysate entering the dialysate flow loop via dialysate flow path 320 to determine if overall dialysate sodium ion concentration is within a predetermined level for the dialysis therapy session.

In the embodiment shown in FIG. 4, the urea content of the dialysate entering the dialysate regeneration unit can be measured in a real-time and/or continuous fashion as described in FIG. 3. However, in some embodiments the conductivity of flow stream 302 is measured during the majority of the period of treatment, for example, 90% of the treatment time. To obtain a reading from the first sample flow 306 (pre-urease flow), the first sampling valve 401 can be switched to a first sampling position to allow flow into the bypass conduit 306 and the second sampling valve 402 can be switched to a position to block flow from the regeneration cartridge outlet 302 from reaching conductivity meter 204. To measure the conductivity of the second sample stream 307, sampling valve 401 can be switched to the second intake position to allow flow from the second sampling conduit 307 while the second sampling valve 402 remains switched to allow the sampling flow 307 to pass through conductivity meter 204 and the post-urease conductivity measurement is taken. As described above with reference to FIG. 3, the dialysate flow sensor 203 can take dialysate flow rate measurements that can be used to calculate additional data.

Figure 5:
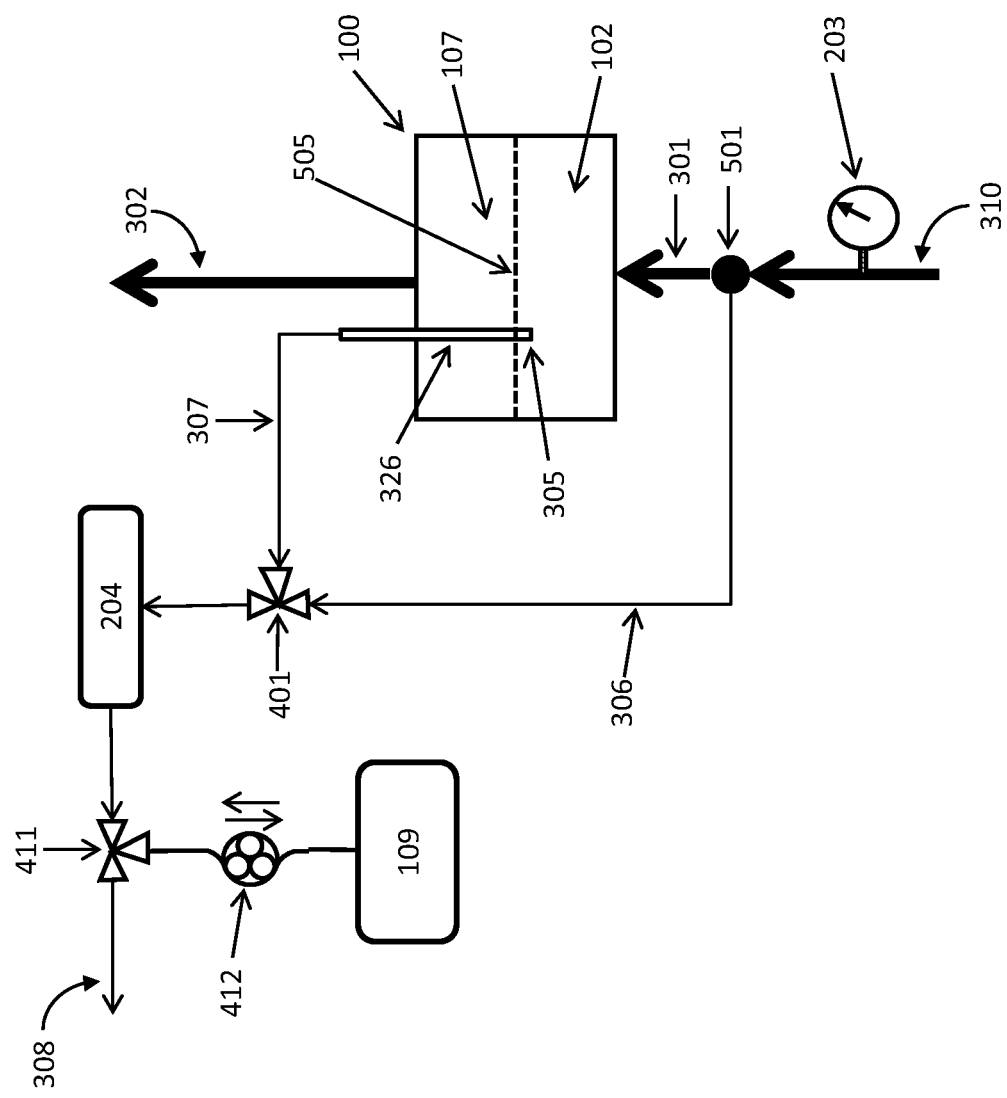
FIG. 5 shows a dialysate regeneration unit having a dialysate conductivity sensor in fluid communication with multiple sampling flow streams operating in accordance with certain embodiments.

FIG. 5 illustrates a dialysate regeneration unit or device in which the urease material 102 and the regenerative material(s) 107 can be contained in sequential layers within a single housing of the sorbent cartridge 100. In this example, either the pre-urease sample stream 306 or a post-urease sample stream 307 can be intermittently directed to the single conductivity sensor 204 by way of sampling valve 401 for conductivity measurement. In FIG. 5, the post-urease sample stream 307 is conveyed directly from the interior of the sorbent cartridge 100 at the interface 505 between the urease material layer 102 and the sorbent material(s) layer 107. Sample stream 307 is conveyed to the exterior of the regeneration cartridge 100 by way of a dedicated sampling bypass duct 326. The inlet 305 to the sampling bypass duct 326 is positioned immediately below the interface 505 between the urease material layer 102 and the sorbent material(s) layer 107, to ensure sample stream 307 has contacted a majority of the urease material layer 102, but has not contacted the sorbent material(s) layer 107, which could adversely affect the conductivity measurement.

In various embodiments, the sorbent material(s) 107 can consist of a single material, multiple layers of individual materials, or multiple intermixed materials. In any embodiment in accordance with FIG. 5, the sampling bypass duct 326 can consist of a segment of metallic, polymeric or composite tubing that extends between the urease material 102 and the sorbent material(s) 107 to the exterior of the sorbent cartridge 100. In various embodiments, the sampling bypass duct 326 can be a compatible rigid-wall, flexible or pliable material known in the art. The inlet 305 to the sampling bypass duct 326 could also contain a mesh or filter material to prevent urease material 102 from leaving the sorbent cartridge 100.

Thus, the chemical reactions and adsorption occurring in individual sorbent material layers can be monitored independently without necessitating the insertion of a sensor into the cartridge or packaging of the sorbent layers in separate containers joined by connecting fluid conduits. In various embodiments, the sensor can measure differential conductivity, pH, and/or use optical detection to analyze the dialysate.

In any embodiment in accordance with FIG. 5, the operation of sampling valve 401 is equivalent to that described above with reference to FIG. 3. Thus, conductivity measurements can be taken for the pre-urease sample stream 306 and the post-urease sample stream 307 and compared to determine the performance of the urease material 102 in removing urea from the spent dialysate. As described above with reference to FIG. 3, the dialysate flow sensor 203 can take dialysate flow rate measurements that can be used to calculate additional data.

Figure 6:
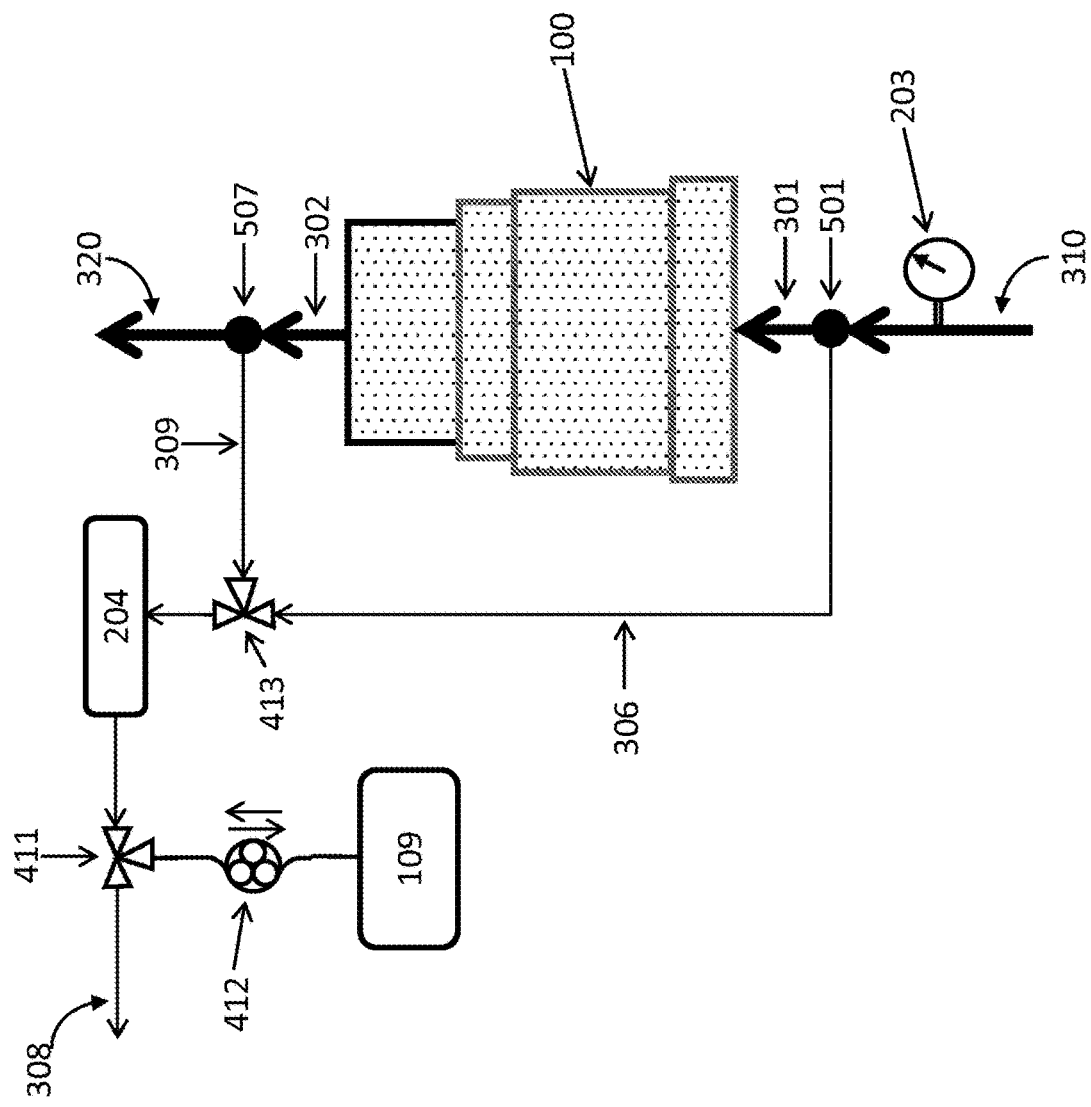
FIG. 6 shows a dialysate regeneration unit having a dialysate conductivity sensor in fluid communication with multiple sampling flow streams operating in accordance with certain embodiments for determining a differential conductivity.

FIG. 6 depicts a dialysate regeneration unit or device in which the urease material 102 and the sorbent material(s) 107 can be comingled or intermixed in the sorbent cartridge 100. Any embodiment in accordance with FIG. 6 can intermittently divert a post-dialyzer (pre-urease) sample stream 306 via junction point 501 upstream of the dialysate regeneration sorbent cartridge 100 and a post-regeneration sample stream 309 via junction point 507 downstream of the regeneration cartridge 100 by way of sampling valve 413 to conductivity sensor 204. The operation of the sampling valve 413 can be equivalent to that described above with reference to FIG. 3, except that in embodiments in accordance with FIG. 6 the difference between the measured conductivity of the post-urease sample stream 309 and that of the pre-urease sample stream 306 can determine the differential conductivity across the entire sorbent cartridge 100. For example, the differential conductivity across the sorbent cartridge 100 can be used to monitor the sodium ion concentration and/or conductivity of the dialysate, which can be used to determine an appropriate amount of a diluent to be added to the dialysate flow loop to maintain a relatively constant biocompatible saline solution.

Ionic dialysance is a method known in the art to effectively quantify effective clearance for a dialysis session (Steil et al., Int'l Journ Artif Organs, 1993, In Vivo Verification of an Automatic Noninvasive System for Real Time Kt Evaluation, ASAIO J., 1993, 39:M348-52, which is incorporated herein by reference). Periodic sodium ion boluses can be directed through the dialysate regeneration sorbent cartridge 100 to calculate the effective ionic clearance based upon the changes in pre- and post-dialyzer conductivity measurements during the bolus. The measurements can be taken multiple times during a hemodialysis session and integrated to measure session "Kt". By this method, errors due to factors that change the clearance rate (clearance variability between dialyzers, blood access recirculation, blood flow rate errors, dialyzer clogging, access connection reversal, dialysis session interruptions) can be eliminated. Because sodium and urea have nearly identical clearances, a conductive dialysance measurement with sodium boluses has been demonstrated to be a surrogate for urea clearance. The general method for measuring effective dialysance by means of a bolus and conductivity measurements is as follows, with reference to FIG. 7 and any other figures with like component numbers:

1. Measure initial conductivity at dialyzer inlet 314 ($Cd_{i1}$).
2. Measure initial conductivity at dialyzer outlet 315 ($Cd_{o1}$).
3. Introduce electrolyte concentrate or diluent to the dialysate stream in order to create a bolus shift in the electrolyte concentration and corresponding conductivity level.
4. Measure bolus conductivity at dialyzer inlet 314 ($Cd_{i2}$).
5. Measure bolus conductivity at dialyzer outlet 315 ($Cd_{o2}$).
6. Calculate effective clearance ($K_{eff}$). The effective clearance is calculated according to Equation 2.

$$K_{\mathit{eff}} = Q_d * \frac{(Cd_{i1} - Cd_{o1}) - (Cd_{i2} - Cd_{o2})}{(Cd_{i1} - Cd_{i2})} \quad \text{(Equation 2)}$$

K can be calculated using Equation 3 below using dialysate flow rate ($Q_d$), concentration in the dialysate entering the dialyzer ($Cd_i$) and the concentration in the dialysate exiting the dialyzer ($Cd_o$) and concentration in the blood entering the dialyzer ($Cb_i$).

$$K = Q_d * \frac{Cd_o - Cd_i}{Cb_i - Cd_i} \quad \text{(Equation 3)}$$

Since the concentration of urea entering the dialyzer is zero, this relationship can be reduced to $$K = Q_d * \frac{Cd_o}{Cb_i} \quad \text{(Equation 4)}$$

or rearranged as Equation 5

$$Cb_i = \frac{Q_d * Cd_o}{K}. \quad \text{(Equation 5)}$$

The dialysate flow rate is readily measured by means such as a flow meter 203 shown in various figures. The effective clearance can be determined as described above and with equation 2, by ionic dialysance measurements. The effective clearance determined with ionic dialysance is essentially equal to the clearance (K) for urea. Therefore, by determining the dialysate flow rate ($Q_d$) and the urea concentration of the dialysate exiting the dialyzer ($Cd_o$) the blood concentration of urea entering the dialyzer ($Cb_i$) can be determined. The urea concentration of the dialysate exiting from the dialyzer outlet can be measured by comparison of the conductivity of sample streams 306 and 307, shown in various figures and described above.

Figure 7:
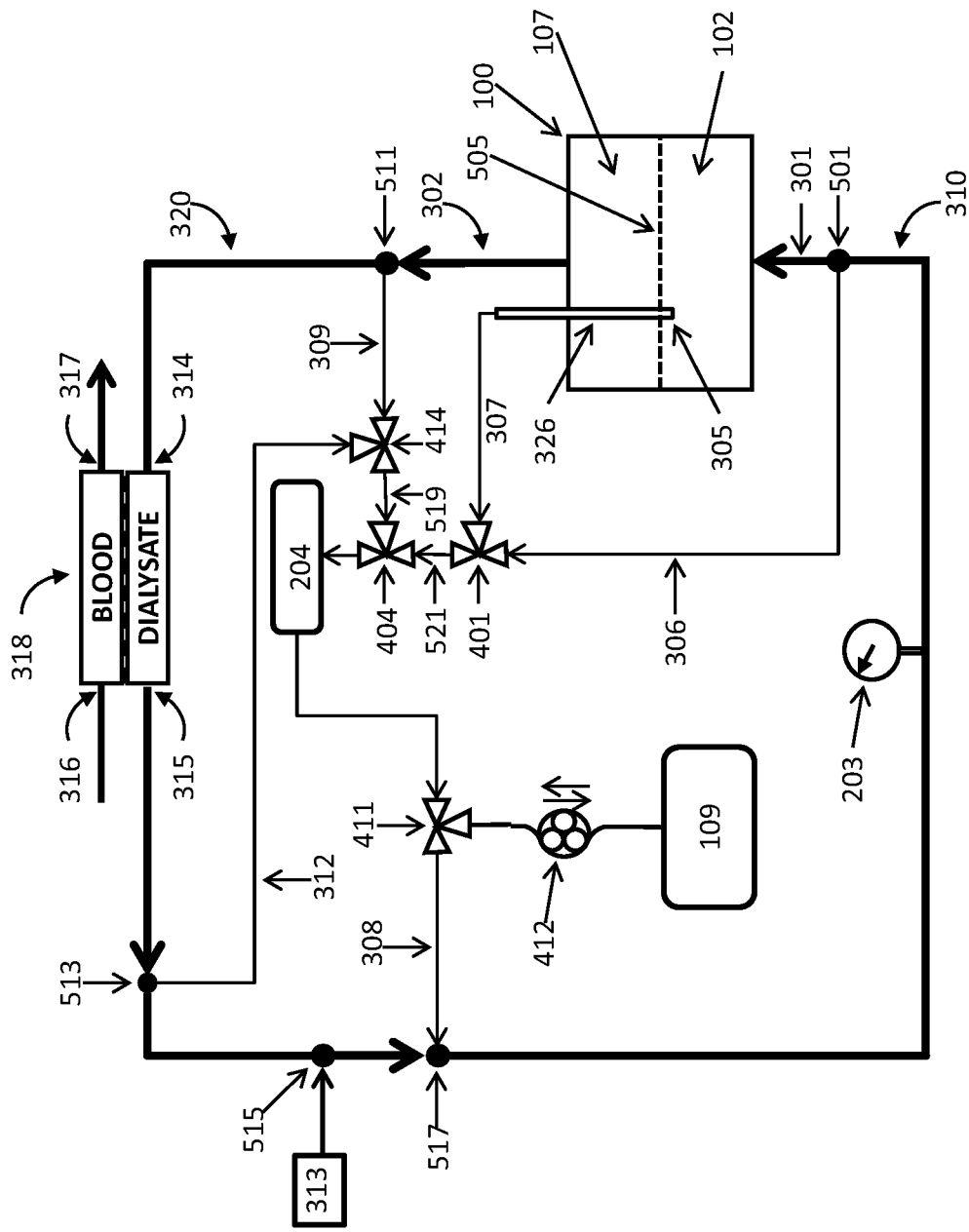
FIG. 7 shows a dialysate regeneration unit having a dialysate conductivity sensor in fluid communication with four sampling flow streams operating in accordance with certain embodiments.

FIG. 7 shows a dialysate regeneration unit or device in which the urease material 102 and the sorbent material(s) 107 can be contained in sequential layers within the regeneration cartridge 100, similar to the configuration described above with reference to FIG. 5. However, in embodiments in accordance with FIG. 7, four different sample streams 306, 307, 309, 312 can be diverted from various points in the dialysate flow path to the single conductivity sensor 204 by way of the sampling valves 401, 414 and 404 for intermittent conductivity measurement. The first sample stream 306 can be diverted from the post-dialyzer (pre-urease) sample stream 310 via junction 501 and intermittently directed to the conductivity sensor 204 by way of sampling valves 401 and 404 for conductivity measurement. The second sample stream 307, which consists of dialysate that has passed through the urease material layer 102 can be collected as described above through the sampling bypass duct 326 and intermittently directed to the conductivity sensor 204 by way of sampling valves 401 and 404 for conductivity measurement. The third sample stream 309, which consists of dialysate that has passed through sorbent cartridge 100 can be collected through junction 511 and intermittently directed to the single conductivity sensor 204 by way of sampling valves 414 and 404 for conductivity measurement. The fourth sample stream 312, which consists of dialysate exiting the dialyzer 318 can be collected through junction 513 and intermittently directed to the single conductivity sensor 204 by way of sampling valves 414 and 404 for conductivity measurement. In this respect, in any embodiment in accordance with FIG. 7 sampling valve 401 can be configured to close off flow from sample stream 307 and allow flow from sample stream 306, or vice versa. Also, sampling valve 404 can be configured to close off flow from stream 521 and allow flow from stream 519, or vice versa. Finally, sampling valve 414 can be configured to close off flow from sample stream 312 and allow flow from sample stream 309, or vice versa.

Similarly, with reference to FIG. 7, the second, post-urease, sample stream 307 can be diverted from the urease material 102 near the interface 505 between the urease material 102 and the sorbent material(s) 107 and intermittently directed to the single conductivity sensor 204 by way of the sampling bypass duct 326, sampling valve 401 and sampling valve 404 for conductivity measurement. In this case, sampling valve 401 can be configured to close off flow from sample stream 306 and allow flow from sample stream 307, while sampling valve 404 simultaneously is configured to close off flow from stream 519 and allow flow from stream 521 to the single conductivity sensor 204. With further reference to FIG. 7 the pre-urease conductivity ($C_{pre-U}$) can be obtained by switching valves 401 and 404 to permit the first sample stream 306 to flow through the conductivity meter 204. Post-urease conductivity ($C_{post-U}$) can be obtained by switching valve 401 to allow the second sample stream 307 to flow through the conductivity meter 204 to measure the conductivity of fluid exiting the urease material 102.

The post sorbent cartridge sample stream 302 of FIG. 7 can be diverted downstream of the sorbent cartridge 100 via junction 511 and intermittently directed to the conductivity sensor 204 by way of sampling valve 414 and sampling valve 404 for measurement of the dialysate or bolus conductivity at the dialyzer inlet 314. In order to accomplish this, sampling valve 414 can be configured to close off flow from sample stream 312 at the dialyzer outlet 315 and allow flow from sample stream 309, while sampling valve 404 simultaneously is configured to close off flow from sampling valve 401 and allow flow from sampling valve 414 to the conductivity sensor 204.

In addition, any embodiment can incorporate an infusate injector 313, downstream of the dialyzer and upstream of the sorbent cartridge 100 that can add one or more infusates to the dialysate, such as a buffering agent or other components typically employed to compose a dialysate solution. The infusate injector 313 can consist of a reservoir containing an infusate and a pump to deliver the infusate to the dialysate flow loop via junction 515. Alternatively, the infusate injector 313 may be located in other locations on the dialysate flow loop. In order to facilitate the determination of the conductivity change contributed by the infusate from the infusate injector 313, a sample stream 312 can be diverted downstream of the dialyzer 318 and upstream of the infusate injector 313 and intermittently directed to the conductivity sensor 204 by way of sampling valve 414 and sampling valve 404. In order to accomplish the conductivity measurement of sample stream 312, sampling valve 414 can be configured to close off flow from sample stream 309 and allow flow from sample stream 312, while sampling valve 404 simultaneously is configured to close off flow from sampling valve 401 and allow flow from sampling valve 414 to the conductivity sensor 204.

Conductivity measurements taken from sample stream 312 can then be compared to those of sample stream 306, which can be taken as described above, to determine the conductivity change resulting from the addition of the infusates to the spent dialysate. Likewise, conductivity measurements taken from sample stream 312 can also be compared to those of sample stream 309, which can be taken as described above, to determine the performance or efficiency of the dialyzer 318 with respect to the removal of impurities and waste products from the bloodstream entering inlet stream 316 and exiting outlet stream 317 of the dialyzer 318. As described above, measurements of the dialysate flow rate taken at flow rate sensor 203 can be used to calculate the total amount of infusates added to the dialysate or the total amount of impurities and waste products removed from the bloodstream over time.

Further, the embodiment of FIG. 7 can be advantageously applied to ionic dialysance measurements as describe above in connection to FIG. 6. As describe above, the system described in FIG. 7 can be used to alternately measure four different sample streams using single conductivity sensor 204, which can be summarized as follows: pre-urease or first sample stream 306, post-urease or second sample stream 307, pre-dialyzer or third sample stream 309 and post-dialyzer or fourth sample stream 312. Ionic dialysance measurements can be accomplished by selectively modifying the rate of introduction of an infusate by infusate injector 313. Initial conductivity ($Cd_{i1}$) at the dialyzer inlet 314 can be obtained by switching valves 414 and 404 to permit the third sample stream 309 to flow through the conductivity meter 204 to indicate conductivity at the dialyzer inlet 314 prior to introduction of an electrolyte bolus or diluent. The initial conductivity ($Cd_{o1}$) at the dialyzer outlet 315 can be obtained by switching valve 414 and 404 to permit the fourth sample stream 312 to flow through the conductivity meter 204 to indicate conductivity of the stream at the dialyzer outlet 315 prior to introduction of an infusate from the infusate injector 313.

With reference to FIG. 7, conductivity measurements for ionic dialysance can be obtained through the following operations. Additional conductivity measurements can then be obtained by initiating an electrolyte bolus (or diluent bolus) from the infusate injector 313 to allow an altered conductivity at the dialyzer inlet 314 and outlet 315 of the dialyzer to be obtained. A bolus can be initiated by switching valves 414 and 404 to allow for the third sample stream 309 to flow through the conductivity meter 204 and an infusate is introduced by infusate injector 313 to either raise or lower the electrolyte concentration in dialysate stream 310. Bolus conductivity ($Cd_{i2}$) at the dialyzer inlet can then be obtained by continuing to measure conductivity with valves 414 and 404 set to allow the third sample stream 309 to flow into the conductivity senor 204 until a minimum or maximum conductivity is detected in response to the bolus introduced by infusate injector 313. After a minimum or maximum conductivity for $Cd_{i2}$ is detected in response to the bolus, valve 414 is switched to allow the fourth sample stream 312 to be directed toward conductivity meter 204 and the bolus conductivity at the dialyzer outlet ($Cd_{o2}$) is obtained when a minimum or maximum conductivity is observed.

Upon obtaining conductivity values $Cd_{i1}$, $Cd_{o1}$, $Cd_{i2}$, and $Cd_{o2}$, effective clearance can be calculated using Equation 2 above. The dialysate flow rate (Qd) can be obtained from flow sensor 203. One skilled in the art will understand that pre- ($C_{pre-U}$) and post-urease ($C_{post-U}$) are not needed for the calculation of effective clearance ($K_{eff}$). As such, the dialysate regeneration unit can contain intermixed sorbent and/or urease materials as shown in FIG. 6 while allowing for ionic dialysance measurements to be taken. Further, blood urea concentration can be calculated using Equation 5 upon calculating the value of urea in the dialysate exiting the dialyzer ($Cd_o$) using the pre- and post-urease conductivity measurements.

Figure 8:
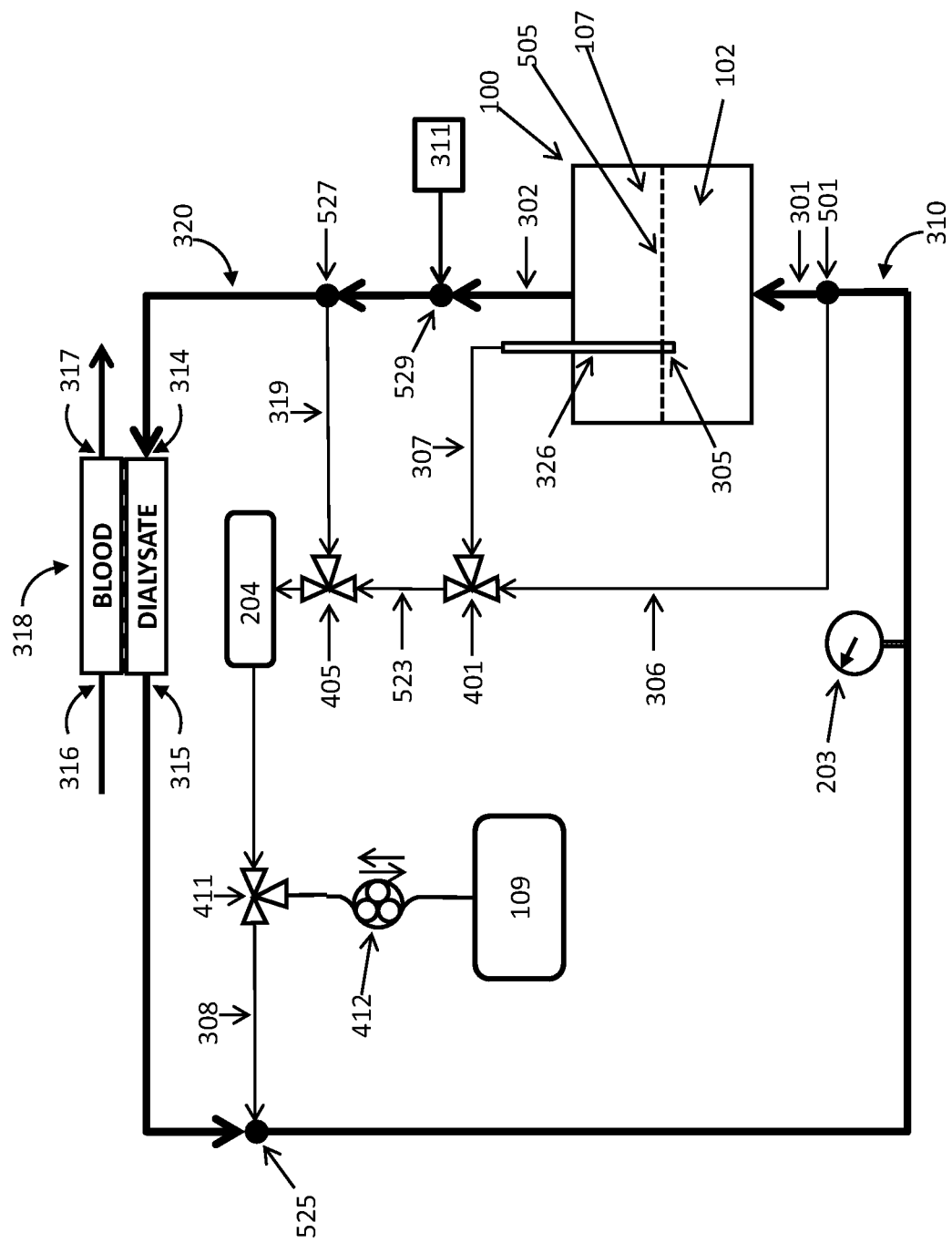
FIG. 8 shows a dialysate regeneration unit having a dialysate conductivity sensor in fluid communication with multiple sampling flow streams and an infusate injector.

As shown in FIG. 8, any embodiment can incorporate an infusate injector 311 downstream of the sorbent cartridge 100 and upstream of the dialyzer 318 that can add one or more infusates to the dialysate, such as potassium ion, calcium ions, magnesium ions or other components typically employed to compose a dialysate solution. In order to facilitate the determination of the overall conductivity change resulting from the removal of impurities and waste products by the sorbent materials 107 in the sorbent cartridge 100 and the addition of the infusates by infusate injector 311, the sample stream 319 can be diverted downstream of the sorbent cartridge 100 and infusate injector 311 and upstream of the dialyzer 318 with junction 527 and intermittently directed to the single conductivity sensor 204 by way of sampling valve 405. Infusate injector 311 is the same as infusate injector 313, shown in FIG. 7, except for its position along the dialysate flow loop.

In order to accomplish the conductivity measurement of sample stream 319, sampling valve 405 can be configured to close off flow from sampling valve 401 and allow flow from sample stream 319 to the single conductivity sensor 204. Conductivity measurements from sample stream 319 can be compared to those from sample stream 306 or sample stream 307, taken as described above with reference to FIG. 7 in order to determine the overall conductivity change resulting from the removal of impurities and waste products by the sorbent materials 107 in the sorbent cartridge 100 and the addition of the infusates by infusate injector 311. Similarly, conductivity measurements from sample stream 319 can be compared to those from sample stream 307, also taken as described above with reference to FIG. 7 in order to determine the overall conductivity change resulting from the removal of impurities and waste products by both the urea material 102 and the sorbent materials 107 as well as from the addition of the infusates by infusate injector 311. Urea content can be determined by comparing the conductivity of sample streams 306 and 307 as described for FIG. 3.

As in FIG. 7, the embodiment shown in FIG. 8 can be used to obtain ionic dialysance measurements for use in conjunction with Equations 2-5. Initial conductivity ($Cd_{i1}$) at the dialyzer inlet 314 can be obtained by switching valve 405 to permit the third sample stream 319 to flow through the conductivity meter 204. Initial conductivity ($Cd_{o1}$) at the dialyzer outlet 315 can be obtained by switching valves 401 and 405 to permit the first sample stream 306 to flow through the conductivity meter 204. Since the infusate injector 311 is not located between the dialyzer outlet 315 and the inlet 301 of the sorbent cartridge 100, the first sample stream 306 indicates the conductivity of the spent dialysate exiting the dialyzer.

A bolus can be initiated by switching valves 401 and 405 to allow for the third sample stream 319 to flow through the single conductivity sensor 204 and an infusate (bolus) is introduced by infusate injector 311 to either raise or lower the electrolyte concentration in the dialysate flow path 320. Bolus conductivity ($Cd_{i2}$) at the dialyzer inlet 314 can then be obtained by continuing to measure conductivity of the third sample stream 319 until a minimum or maximum conductivity is detected in response to the bolus introduced by infusate injector 311. After a minimum or maximum conductivity ($Cd_{i2}$) at the dialyzer inlet 314 is detected in response to the bolus, valves 401 and 405 are switched to allow the first sample stream 306 to be directed toward the single conductivity sensor 204 and the bolus conductivity ($Cd_{o2}$) at the dialyzer outlet 315 is obtained when a minimum or maximum conductivity is observed.

Upon obtaining conductivity values for $Cd_{i1}$, $Cd_{o1}$, $Cd_{i2}$, and $Cd_{i2}$, effective clearance can be calculated using Equation 2 above. The dialysate flow rate (Qd) can be obtained from flow sensor 203. As explained above, all of the values indicated by Equations 2-5 can be calculated from the obtained conductivity data.

Figure 9:
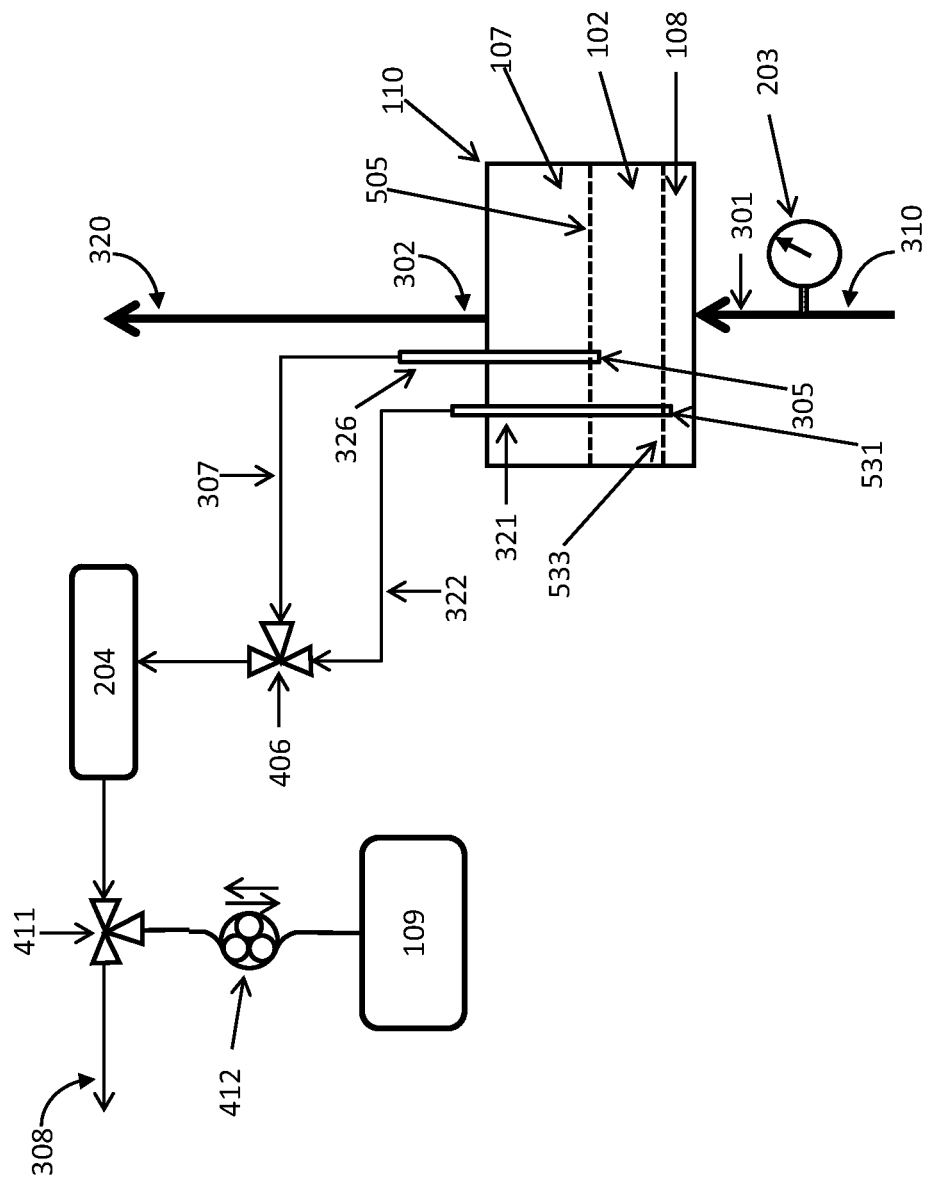
FIG. 9 shows a dialysate regeneration unit having a dialysate conductivity sensor in fluid communication with multiple sampling flow streams operating with a highly-selective ion exchange resin.

Further, any embodiment can incorporate a modified sorbent cartridge 110 that includes one or more sorbent materials 108, such as a highly-selective ion exchange resin, for example, selective for calcium ions and/or magnesium ions, upstream of the urease material 102 and an additional one or more sorbent materials 107 as shown in FIG. 9. In layer 108, the selective resin releases hydrogen ions ($H^+$) in exchange for calcium ($Ca^{2+}$) and magnesium ($Mg^{2+}$), which acts to acidify the solution and promotes the conversion of ammonia to ammonium after enzymatic urea breakdown occurs in the urease material 102. The sorbent cartridge 110 can include a post-urease sampling bypass duct 326, equivalent to that described above with reference to FIG. 5, as well as an additional dedicated sampling bypass duct 321, similar in construction to sampling bypass duct 326, but downstream of the sorbent material(s) 108 and upstream of the urease material 102. A sample stream 322 can be conducted from sampling bypass duct 321 with inlet 531 positioned immediately below the interface 533 between the urease material layer 102 and the sorbent material(s) layer 108, to ensure sample stream 322 has contacted a majority of the sorbent material layer 108, but has not contacted the urease material(s) layer 102, which could adversely affect the conductivity measurement.

In order to measure the conductivity of sample stream 322 in FIG. 9, sampling valve 406 can be configured to close off flow from sample stream 307 and allow flow from sample stream 322 to the single conductivity sensor 204. Conductivity measurements from sample stream 307, taken as described above with reference to FIG. 5 with the substitution of sampling valve 406 directing the flows from sample stream 322 and sample stream 307 in place of sampling valve 401 directing the flows from sample stream 306 and sampling stream 307 in order to determine the conductivity change resulting from the removal of impurities and waste products by the urease material 102 in the modified sorbent cartridge 110. As will be understood by one of ordinary skill in the art, the modified sorbent cartridge 110 described in FIG. 9 can be combined with any of the additional sampling configurations external to the sorbent cartridge 100 described herein, to configure additional embodiments of the invention.

Figure 10:
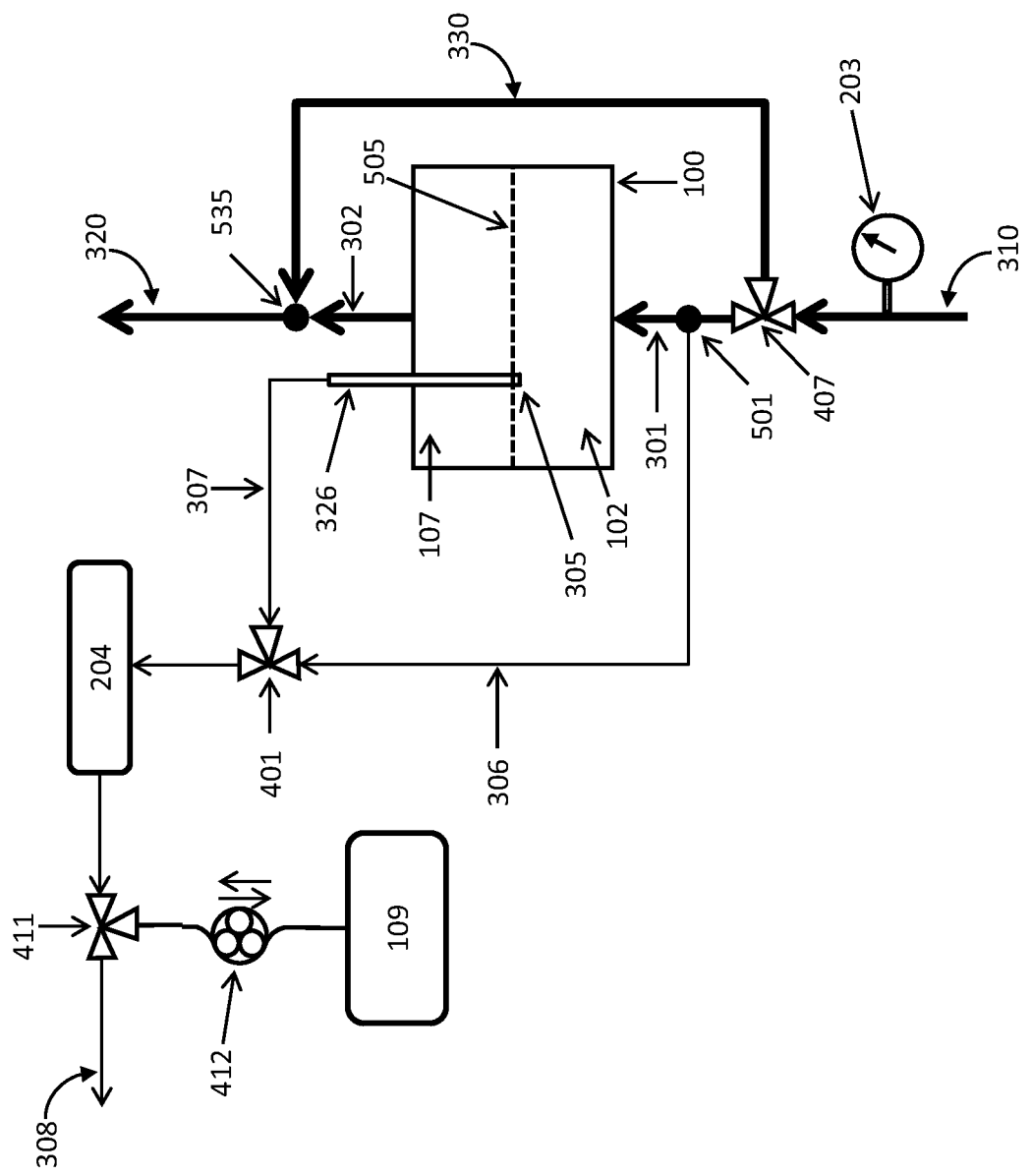
FIG. 10 shows a dialysate regeneration unit having a dialysate conductivity sensor in fluid communication with multiple sampling flow streams operating with a regeneration unit bypass flow path.

Any embodiment of the invention can include a sorbent cartridge bypass flow path 330 as shown in FIG. 10. The sorbent cartridge bypass flow path 330 can be diverted from the upstream dialysate flow path 310 and rejoin at the dialysate flow path 320 downstream of the sorbent cartridge 100. The sorbent cartridge bypass flow path 330 can incorporate a bypass valve 407, which, for example, may be a three-way valve, as depicted in FIG. 10, or a combination of two-way valves. One skilled in the art will appreciate that the bypass valve 407 can be placed as shown in FIG. 10, as well as at an intermediate point within the sorbent cartridge bypass flow path 330 or at the downstream junction 535. Thus, the sorbent cartridge bypass flow path 330 can inhibit the flow of dialysate through the sorbent cartridge 100 while continuing to circulate dialysate flow through the dialyzer. For example, the bypass flow path 330 can be utilized to facilitate equilibration of the dialysate concentration of urea and other impurities and waste products with the concentration of these components in the blood passing through the dialyzer.

As described in connection with FIG. 3, measurement of the urea concentration of the dialysate in the post-dialyzer segment 310 of the dialysate flow loop can be used to calculate and monitor clearance Kt. However, an indication of the urea content of the fluid within the dialyzer is not directly provided. During active dialysis, a concentration gradient between the dialysate and the blood is maintained to establish hemodialysis treatment. The size of the gradient depends on several factors, as such, measurement of dialysate urea content does not allow for a direct measurement to be made of the urea content of the blood. When bypass flow 330 is operated, hemodialysis treatment is suspended as the dialysate comes into equilibrium with the blood and the concentration gradient of urea and other solutes between the blood and the dialysate approaches zero. After several passes of the dialysate through the bypass flow 330, the dialysate urea concentration will reflect the blood urea concentration. When valve 307 is operated to re-establish dialysate flow through the sorbent cartridge 100, the single conductivity sensor 204 can be used to determine the performance of the urease-containing material as well as other sorbents to evaluate the content of the dialysate, which is in temporary equilibrium with the blood. As such, the system can be used to periodically determine the urea content of the blood followed by a return to hemodialysis treatment.

Blood urea concentration or BUN and dialyzer clearance (K) can be measured as follows using the embodiment shown in FIG. 10. Pre-urease conductivity ($C_{pre-U1}$) can be measured by switching valve 401 to permit the first sample stream 306 to flow to the single conductivity sensor 204 while valve 407 directs the dialysate stream 301 through junction 501 and through the sorbent cartridge 100. Initial post-urease conductivity ($C_{post-U1}$) is measured by switching valve 401 to allow the second sample stream 307 to flow through the conductivity meter 204 and a conductivity measurement is obtained as described above for FIG. 5.

Dialysate urea concentration exiting the dialyzer ($Cd_o$) is determined by the conductivity difference between measurements $Cd_{pre-U1}$ and $Cd_{post-U1}$. Dialysate flow sensor 203 can be used to obtain the dialysate flow rate (Qd).

Dialysate urea concentration is then equilibrated to blood urea concentration by switching valve 407 in FIG. 10 to divert the dialysate flow through sorbent bypass loop 330 to cause the dialysate to start the recirculating and equilibration process for a predetermined number of recirculation passes. Alternatively, conductivity of first sample stream 306 can be observed at conductivity meter 204 until it stabilizes, which will indicate that equilibration has occurred between blood and dialysate. With urea equilibrated between blood and dialysate, pre-urease conductivity ($C_{pre-U2}$) is measured by switching valve 401 to direct the first sample stream 306 through conductivity meter 204 and the conductivity measurement of the equilibrated dialysate stream 310 is recorded. The conductivity measurement can be recorded by means well known to those skilled in the art such as with a computer. With urea equilibrated between blood and dialysate, post-urease conductivity ($C_{post-U2}$) is measured by switching valve 407 to stop the bypass re-circulation and direct the flow of urea-equilibrated dialysate through sorbent cartridge 100. At the same time, valve 401 is switched to direct the second sample stream 307 to conductivity meter 204 and the conductivity measurement is recorded.

To calculate the patient's blood urea concentration ($C_{bi}$), the conductivity difference between $C_{pre-U2}$ and $C_{post-U2}$ can be correlated to urea concentration as indicated in Scheme 1. Clearance can be calculated according Equation 4 by using the blood urea concentration as $C_{bi}$; determined in the preceding step and using the difference between the conductivity readings ($C_{dpost-U1} - C_{dpre-U1}$) to determine dialyzer outlet urea concentration $Cd_o$. It should be noted that individual conductivity measurements such as the equilibrated urea concentration can be performed differently and can be optionally measured before any dialysis has altered the patient's BUN.

The examples of FIGS. 3-10 show how the sorbent cartridge 100 or 110 can be used for urea sensing in conjunction with a hemodialysis fluid circuit. Further, in certain embodiments the fluid circuit may be configured for hemofiltration, hemodiafiltration, or peritoneal dialysis. For example, FIG. 11 shows how the sorbent cartridge 100 can be utilized in a hemofiltration circuit to measure approximate blood urea concentration, dialysate urea concentration, and urea removal. The sorbent cartridge 100 includes a urease material 102 and a sorbent material 107. The sorbent cartridge outlet 302 is directed to a replacement fluid flow path 328. A single conductivity sensor 204 is used to measure the conductivity of the dialyzer effluent flow path 327 via the sampling streams 306 and 307 before and after the dialysate passes through the urease layer 102. Since ultrafiltrate has approximately the same urea concentration as whole blood, the subject's approximate BUN can be determined by measuring the conductivity change of the filtrate across the urease material 102. The urea concentration of the filtrate stream 310 can be measured and multiplied by the filtration rate measured by the flow sensor 203 to determine the urea removal rate. The measurement method described can be repeated through the course of a therapy session and integrated to calculate the total urea removed during therapy.

Figure 12:
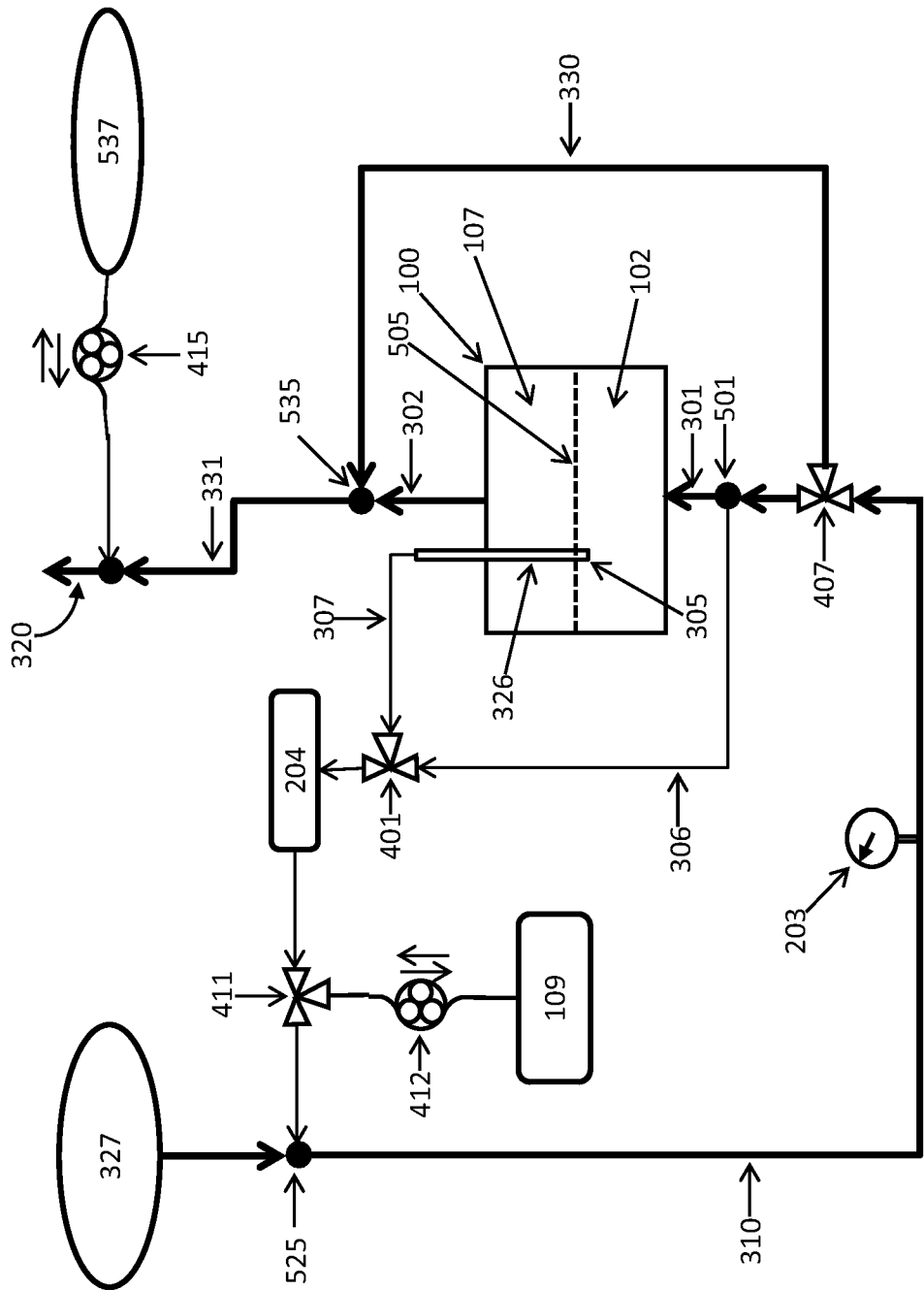
FIG. 12 shows a dialysate regeneration unit having a dialysate conductivity sensor in fluid communication with multiple sampling flow streams operating for use in hemodiafiltration.

FIG. 12 shows how the sorbent cartridge 100 can be utilized in a hemodiafiltration circuit to measure blood urea concentration, dialysate urea concentration, and urea removal. The sorbent cartridge 100 includes a urease material 102 optionally configured as a layer and a sorbent material 107 optionally configured as a layer. The control pump 415 can be operated to transfer a fluid bolus from the replacement fluid reservoir 328 into the dialysate flow path 320 or to transfer dialysate from the dialysate flow path 320 to the replacement fluid reservoir 537. The common conductivity meter 204 measures the conductivity of the dialyzer effluent flow path 327 via the sampling streams 306, 307 before and after the dialysate passes through the urease layer 102 as described in FIG. 10. The effluent flow rate is measured at the flow sensor 203, and blood urea concentration or BUN can be calculated at the start of the therapy session, or at any time during the therapy session as described in FIG. 10.

Figure 13:
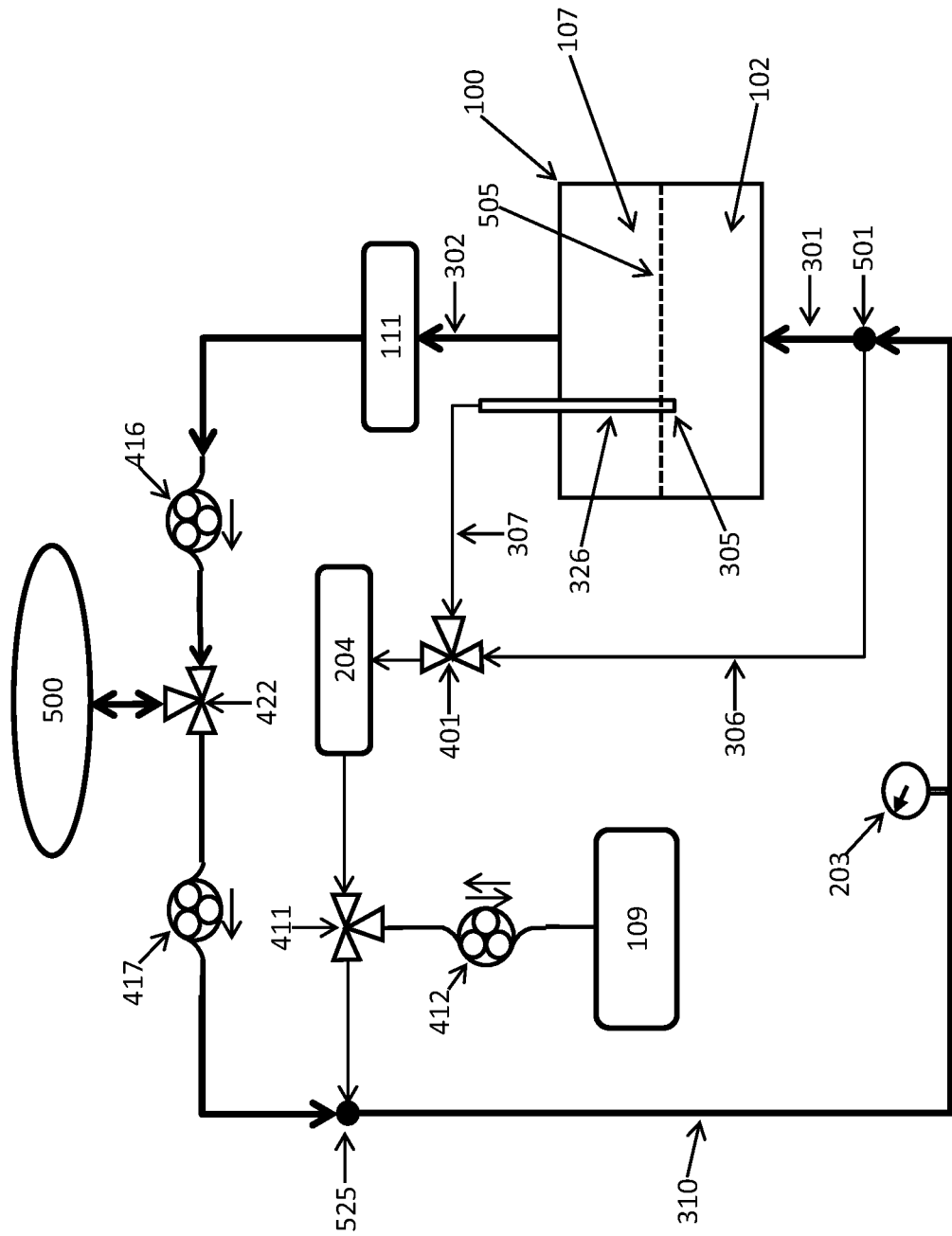
FIG. 13 shows a dialysate regeneration unit having a dialysate conductivity sensor in fluid communication with multiple sampling flow streams operating for use in peritoneal dialysis.

FIG. 13 shows a configuration for using the sorbent cartridge 100 to measure the patient's urea concentration, spent dialysate urea concentration, and total urea removal in a peritoneal dialysis circuit. The sorbent cartridge 100 includes a urease material 102 and a sorbent material 107. A common conductivity meter 204 measures conductivity of the dialysate stream 310 before and after passing through the urease containing layer 102. In various embodiments, the dialysate flow sensor 203 or the speed of pump 417 can measure the flow rate of the effluent. The injection pump 416 can be operated to transfer dialysate from the dialysate reservoir 111 into the peritoneal cavity 500 of a subject and the extraction pump 417 can be operated to transfer dialysate from the peritoneal cavity 500 into the main dialysate flow path 310 for return to the sorbent cartridge 100. The dialysate reservoir 111 can be an expandable reservoir that temporarily stores the purified dialysate exiting sorbent cartridge 100 downstream of the sorbent outlet flow path 302. In any embodiment, the purified dialysate can be rebalanced with prescribed concentrations of electrolytes either before or after reservoir 111.

If the dialysate dwell time in the peritoneal cavity 500 is sufficiently long, the dialysate can equilibrate to the subject blood urea concentration and the blood urea concentration or BUN can be determined by measuring the conductivity change of the dialysate across the urease containing layer 102 as described for FIG. 10. The urea concentration of the main filtrate flow path 310 can be measured and multiplied by the dialysate flow rate measured by flow sensor 203 to determine the urea removal rate. Multiple such measurements can be repeated through the course of a therapy session and integrated to measure total urea removed.

Figure 14:
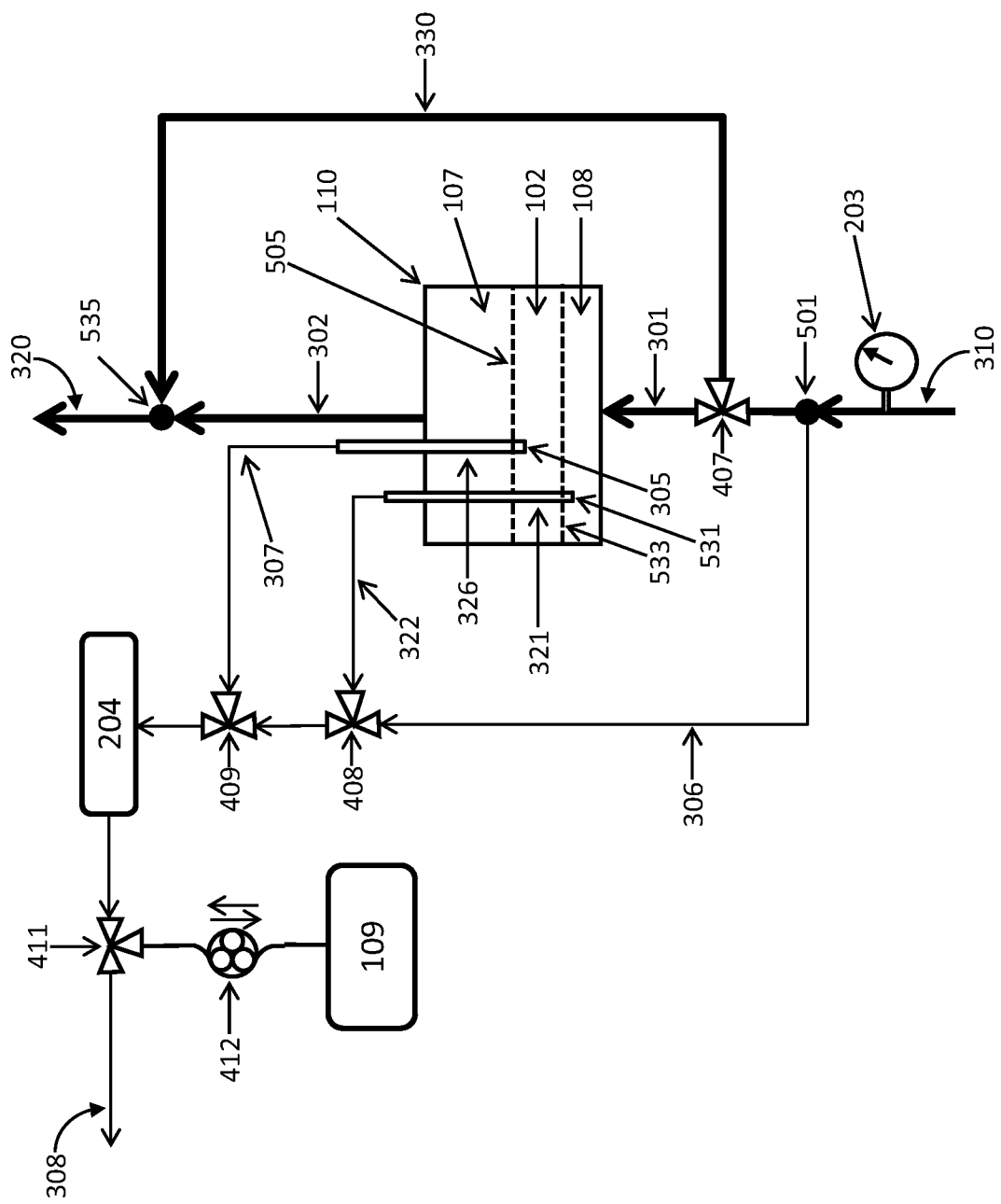
FIG. 14 shows a dialysate regeneration unit with an ion-specific exchange resin and having a dialysate conductivity sensor in fluid communication with multiple sampling flow streams operating in accordance with certain embodiments.

FIG. 14 shows an embodiment employing a sorbent cartridge 110 similar to that shown in FIG. 9 having a sorbent layer 108 containing an ion exchange resin highly selective to $Ca^{2+}$ and $Mg^{2+}$ and releasing $H^+$ in exchange. Valves 408 and 409 alternate the first sample stream 306, second sample stream 322, and third sample stream 307 through a single or common conductivity meter 204 to obtain a precise conductivity difference between the fluid passing through the three sample streams, as follows: first sample stream 306 (post-dialyzer); second sample stream 322 (pre-urease); and third sample stream 307 (post-urease). Also, the flow diagram shown in FIG. 14 includes a sorbent cartridge bypass flow path 330 as described above for FIGS. 10 and 12.

In addition to BUN, total blood concentration of calcium and magnesium ions can also be determined. The first sorbent layer 108 contains a cation exchange resin highly selective for removal of the divalent $Ca^{2+}$ and $Mg^{2+}$ ions from the dialysate stream, such that substantially all $Ca^{2+}$ and $Mg^{2+}$ ions are removed, but only an insignificant proportion of the other cations such as potassium and sodium are removed by layer 108. An example of such a material is a chelating cation exchange resin. An example of a commercially available chelating cation exchange resin is Chelex®100 from Bio-Rad Laboratories, Hercules, Calif. This cation exchange can be expressed according to the following Scheme 2.

(Scheme 2)

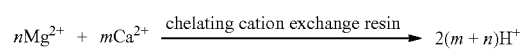

The electrolytic conductivity of a single $H^+$ ion is approximately three-times greater than the electrolytic conductivity of individual $Ca^{2+}$ and $Mg^{2+}$ ions being removed by sorbent layer 108. Further, since two $H^+$ ions are released for each $Ca^{2+}$ or $Mg^{2+}$ ion removed, the electrolytic conductivity of the ions exchanged is on the order of six-times greater at the outlet of sorbent layer 108 than at the inlet to sorbent layer 108. This creates a readily measured conductivity increase that is proportional to the total amount of the total combined divalent $Ca^{2+}$ and $Mg^{2+}$ ions in the dialysate stream in the post dialyzer dialysate flow.

Measurement of the total combined blood concentration of Calcium and Magnesium and also the BUN are performed as follows. Dialysate solute concentration is equilibrated to blood solute concentration by switching valve 409 to divert the dialysate flow through sorbent bypass loop 330 to cause the dialysate to start the recirculating and equilibration process and continues to recirculate for a predetermined number of recirculation passes. Alternatively, valves 408 and 409 can be positioned to pass the first sample stream 306 to conductivity meter 204 and the conductivity reading observed until it stabilizes, which will indicate that equilibration has occurred between blood and dialysate. With solutes now equilibrated between blood and dialysate, post-dialyzer conductivity ($C_{post-dialyzer}$) is measured by switching valves 408 and 409 to direct the first sample stream 306 through conductivity meter 204 and the conductivity measurement of the equilibrated dialysate stream 310 is recorded. With solutes equilibrated between blood and dialysate, pre-urease conductivity ($C_{pre-U}$) is measured by switching valve 409 to stop the bypass re-circulation and to direct the flow of urea-equilibrated dialysate to enter dialysate regeneration unit 110 through inlet 301. At the same time, valve 408 is switched to direct the second sample stream 322 to conductivity meter 204 and the pre-urease conductivity measurement is recorded.

With solutes equilibrated between blood and dialysate, post-urease conductivity ($C_{post-u}$) is measured by switching valve 409 to direct the sample stream 307 through conductivity meter 204 and the post-urease conductivity measurement is recorded. Because the dialysate and blood solutes are equilibrated, the patient's total combined blood concentration of calcium and magnesium is now determined by the conductivity increase between observations $C_{post-dialyzer}$ and $C_{pre-U}$.

Because the dialysate and blood urea are equilibrated, the patient's blood urea concentration can be determined by the conductivity increase between observations $C_{pre-U}$ and $C_{post-U}$ according to Scheme 1. The effective clearance, $K_{eff}$, of either the urea or calcium/magnesium can be further calculated by taking a second set of conductivity readings from each sample stream in the non-equilibrated state and then using the ionic dialysance method of Equation 2 to calculate $K_{eff}$ for urea as explained in relation to FIG. 9. If the infusates containing calcium and magnesium ions are stopped when the second set of readings are taken, then Equation 2 can also be used to determine $K_{eff}$ for calcium and magnesium. If the infusates containing calcium and magnesium were not turned off during the second set of conductivity readings, but instead being infused at a known concentration by a sufficiently accurate metering system, then equation 3 can be used to determine the $K_{eff}$ for calcium and magnesium. The $K_{eff}$ for urea and calcium and magnesium can be measured periodically throughout a therapy session and changes in the $K_{eff}$ can be used to determine issues with the therapy. For example, declines in $K_{eff}$ could indicate the occurrence of access recirculation and/or poor blood flow from the access and/or clotting or clogging of the dialyzer and/or dialysate flow error and/or blood flow error. Some methods for determining the underlying cause of a decrease in $K_{eff}$ can include increasing the patient's anticoagulant dose to reduce clotting of the dialyzer. Also, the blood and/or dialysate flow could be increased to determine their effect on $K_{eff}$ and if necessary maintained at higher flow rates in order to achieve a desired $K_{eff}$.

As shown in FIG. 14, It will be understood that the number of conductivity measurements can depend upon the number of material layers used in the sorbent system. Hence, a fourth measurement can be taken to obtain the concentration of a third solute, a fifth measurement to obtain the concentration of a fourth solute, and so on until all material layers and sensor types in the sorbent system have been measured. Conductivity measurement across additional sorbent layers will require additional sampling bypass ducts similar to sampling bypass duct 321 and 326 at the new material interfaces (not shown). Also, additional sampling valves, similar to 408 and 409 will be required (not shown) to divert the new sample streams to the conductivity sensor 204.

Figure 15:
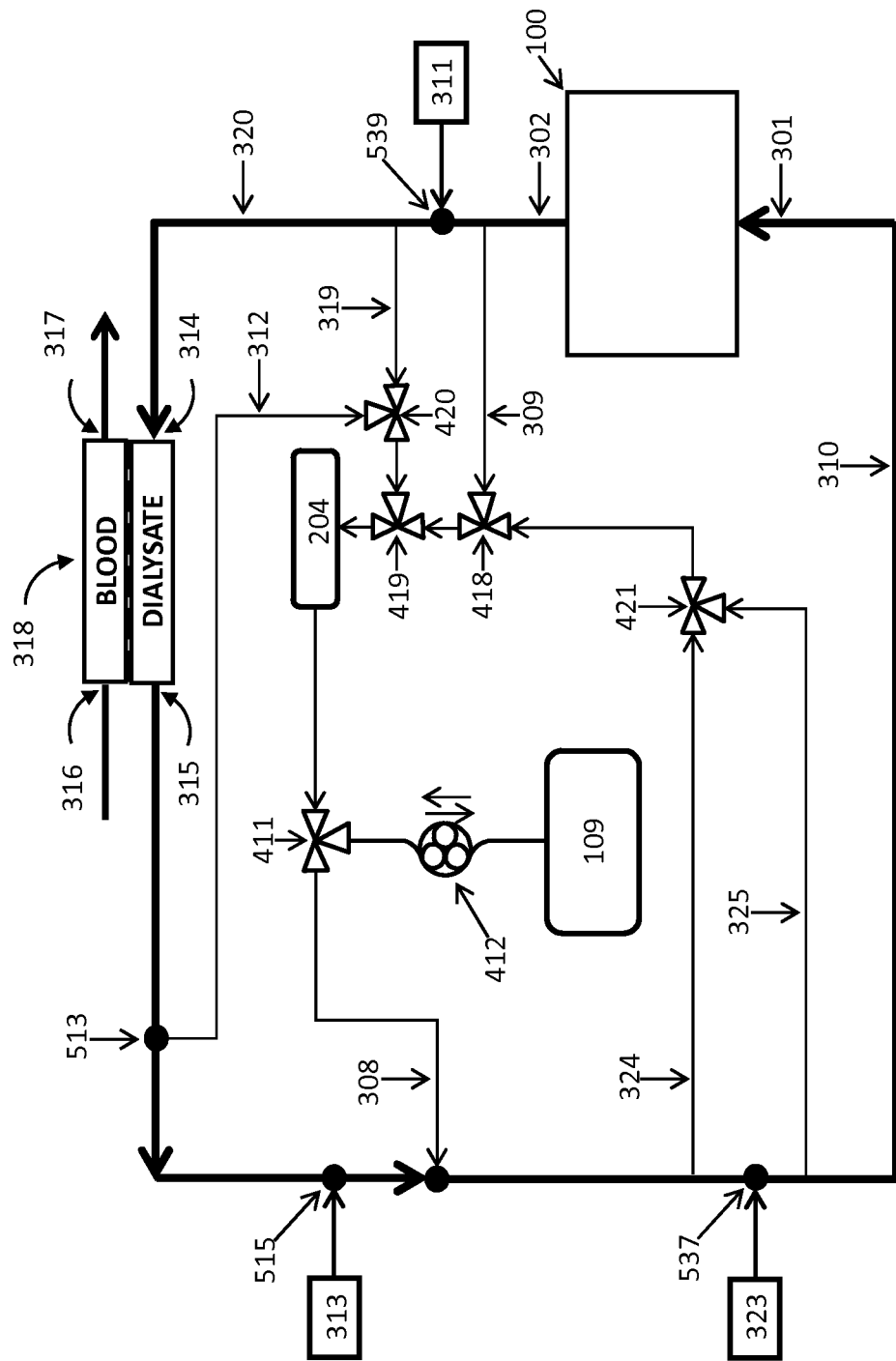
FIG. 15 shows a dialysate regeneration unit having a dialysate conductivity sensor in fluid communication with multiple sampling flow streams in an alternative configuration connected to a water source.

As shown in FIG. 15, any embodiment of the invention can combine various concepts described herein with a fresh water/dialysate source 323 to dilute the dialysate. The fresh water/dialysate source 323 can consist of a reservoir containing water and a pump to deliver water to the dialysate flow loop. Non-limiting types of water that can be used include tap water, potable water, bottled water, deionized water and distilled water. For example, the fresh water/dialysate source 323 can enter the dialysate at a junction point 537 downstream of the dialyzer 318 and the infusate injector 313 and upstream of the sorbent cartridge 100, as depicted in FIG. 15. One skilled in the art will recognize that additional configurations can be used in certain embodiments of the invention, for example, the fresh water/dialysate source 323 can enter the dialysate at a junction point downstream of the dialyzer 318 and upstream of the infusate injector 313.

In combination with the fresh water/dialysate source 323, a pre-water source sample stream 324 and a post-water source sample stream 325 can be incorporated into the dialysate flow path 310 and directed to the conductivity sensor 204 by way of a sampling valve 421, such as the three-way valve shown in FIG. 15. The flow from sampling valve 421 can be further directed to the conductivity sensor 204 by way of sampling valve 418 and sampling valve 419, facilitating conductivity measurement from at least five junction points along the dialysate flow path 310 and 320. Of course, one skilled in the art will recognize that conductivity measurements can be taken from any number of sample streams along the dialysate flow path using a single conductivity sensor 204 by configuring additional sampling valves in a similar manner.

As further shown in FIG. 15, any embodiment of the invention can combine various concepts described herein with a buffer source 311 to change the buffer concentration of the dialysate. The buffer source 311 can consist of a reservoir containing a buffer solution and a pump to deliver the buffer source to the dialysate flow loop. Non-limiting types of buffer source that can be used include aqueous solutions of bicarbonate, lactate and acetate. For example, the buffer source 311 can enter the dialysate at a junction point 539 upstream of the dialyzer 318 and downstream of the sorbent cartridge 100, as depicted in FIG. 15. One skilled in the art will recognize that additional configurations can be used in certain embodiments of the invention, for example, the buffer source 311 can enter the dialysate at a junction point downstream of the dialyzer 318 and upstream of the fresh water/dialysate source 323.

In combination with the buffer source 311, a pre-buffer source sample stream 309 and a post-buffer source sample stream 319 can be incorporated into the dialysate flow path 320 and directed to the single conductivity sensor 204 by way of sampling valves 418, 419, and 420.

Thus, conductivity measurements can be taken from sample streams 309, 319, 312 by configuring the corresponding sampling valves 418, 419, 420 as described above with reference to FIG. 7, with the substitution of the sampling valves 418, 419, 420 for the sampling valves 401, 414, 404, respectively. In addition, conductivity measurements can be taken from sample stream 324 by configuring sampling valve 421 to close off flow from sample stream 325 and allow flow from sample stream 324, while configuring the downstream sampling valves 418 and 419 to close off flow from sample streams 309 and 319 and allow flow from sampling valve 421 to the conductivity sensor 204. Conductivity measurements from sample in dialysate conductivity resulting from dilution of the dialysate with water from the fresh water/dialysate source 323.

Figure 16:
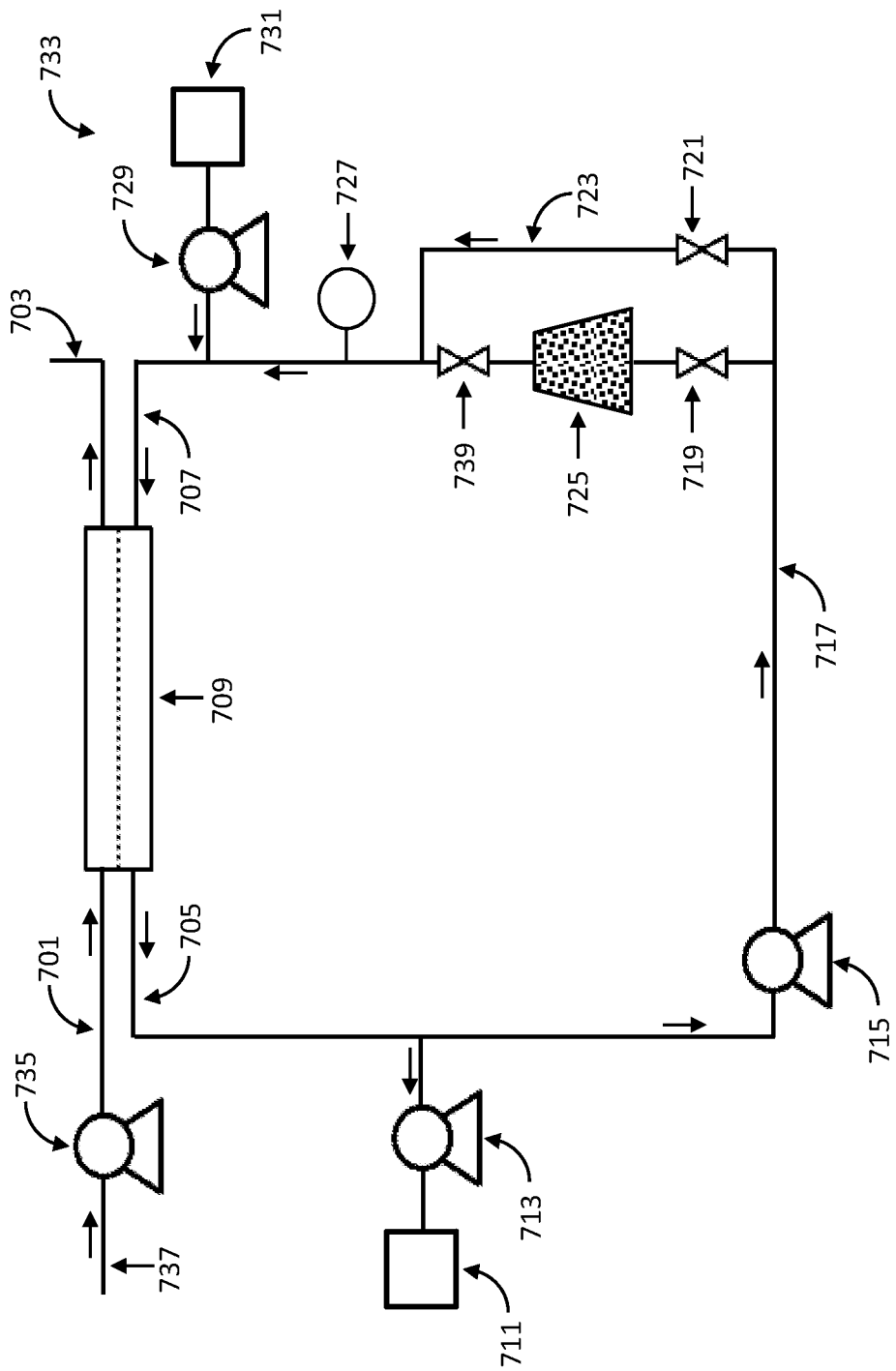
FIG. 16 shows a dialysate regeneration unit having a bypass flow loop around a sorbent cartridge.

FIG. 16 is a simplified flow diagram for a controlled compliant recirculating dialysate loop utilizing a sorbent cartridge 725 for dialysate regeneration and a sorbent cartridge bypass loop 723 for achieving equilibration between the dialysate and blood. Sorbent cartridge 725 can include sorbent materials and function as described for sorbent cartridges 100 and 110 shown in various FIGS. In general, the sorbent cartridge 725 is designed to remove certain species from the dialysate, such as but not limited to urea, creatinine, phosphate, sulfate, calcium, magnesium, potassium and beta-2-microglobulin. Blood from a patient is directed along flow path 737 with pump 735 and enters a dialyzer 709 through a blood inlet flow path 701 and exits the dialyzer 709 through a blood outlet flow path 703 and is returned to the patient. Dialysate is recirculated and regenerated in the dialysate flow loop 717. Dialysate exits the dialyzer 709 through the dialysate outlet flow path 705 and a portion of the dialysate is removed from the dialysate flow loop 717 with a control pump 713 and is collected in a reservoir 711. Dialysate is recirculated through the dialysate flow loop with the dialysate pump 715 and continues to flow towards a sorbent cartridge 725 and a sorbent cartridge bypass loop 723. The position of valves 719, 721 and 739 determine if the dialysate flows through the sorbent cartridge 725 or through the sorbent cartridge bypass loop 723. Other valve positions and valve types are possible to achieve flow through either the sorbent cartridge 725 or the sorbent cartridge bypass loop 723 and are well known to those skilled in the art. Next, dialysate flows to pass a sensor system 727. Sensor system 727 may include a single sensor or multiple sensors. The specific sensors making up sensor system 727 may include one or several of the following, but is not limited to, a conductivity sensor, ion-selective sensor, osmotic pressure sensor, pH sensor, urea sensor, and creatinine sensor. After the sensor system 727 the dialysate flows to pass a reconstitution system 733 which acts to change the composition of the dialysate before the dialysate re-enters the dialyzer through the dialysate inlet flow path 707. The reconstitution system 733 also functions to replace certain species that are removed by the sorbent cartridge 725 such as calcium, magnesium and potassium. The reconstitution system 733 as shown in FIG. 16 includes a reconstitution pump 729 and a reconstitution reservoir 731. The reconstitution reservoir can contain, but is not limited to, electrolyte solutions such as salts of calcium, magnesium, potassium, acetate, chloride and sodium, which will be added to the dialysate via pump 729 in order to change the chemical composition of the dialysate. The reconstitution system may also include multiple pumps and reservoirs (not shown), each containing a different solution for delivery to the dialysate flow loop 717. Other examples of chemical species that can be delivered with the reconstitution system 733 include bicarbonate, glucose, and lactate. The reconstitution system 733 can also include a reservoir containing water that will act to dilute the concentration of species in the dialysate.

In certain embodiments the sorbent cartridge 725 can consist of ion-exchange materials that will remove certain waste species in exchange for sodium. Therefore, in order to maintain a certain dialysate sodium concentration it may become necessary to remove sodium from the dialysate by direct removal of the sodium, or by dilution of the sodium concentration by adding water to the dialysate loop 717.

In certain embodiments for the system illustrated in FIG. 16 the volume of the dialysate flow loop 717 can be less than 1 liter and as small as 0.5 liters. The combination of using a controlled compliant flow path, along with a sorbent cartridge 725 for dialysate regeneration, water feed from the reconstitution system 733 for sodium management, and a control pump 713 for the removal of a certain volume of dialysate from the dialysate flow loop 717, allows the dialysate flow loop to have a small volume. In certain embodiments the dialysate flow loop volume 717 can be 0.5 liters or less.

Figure 17:
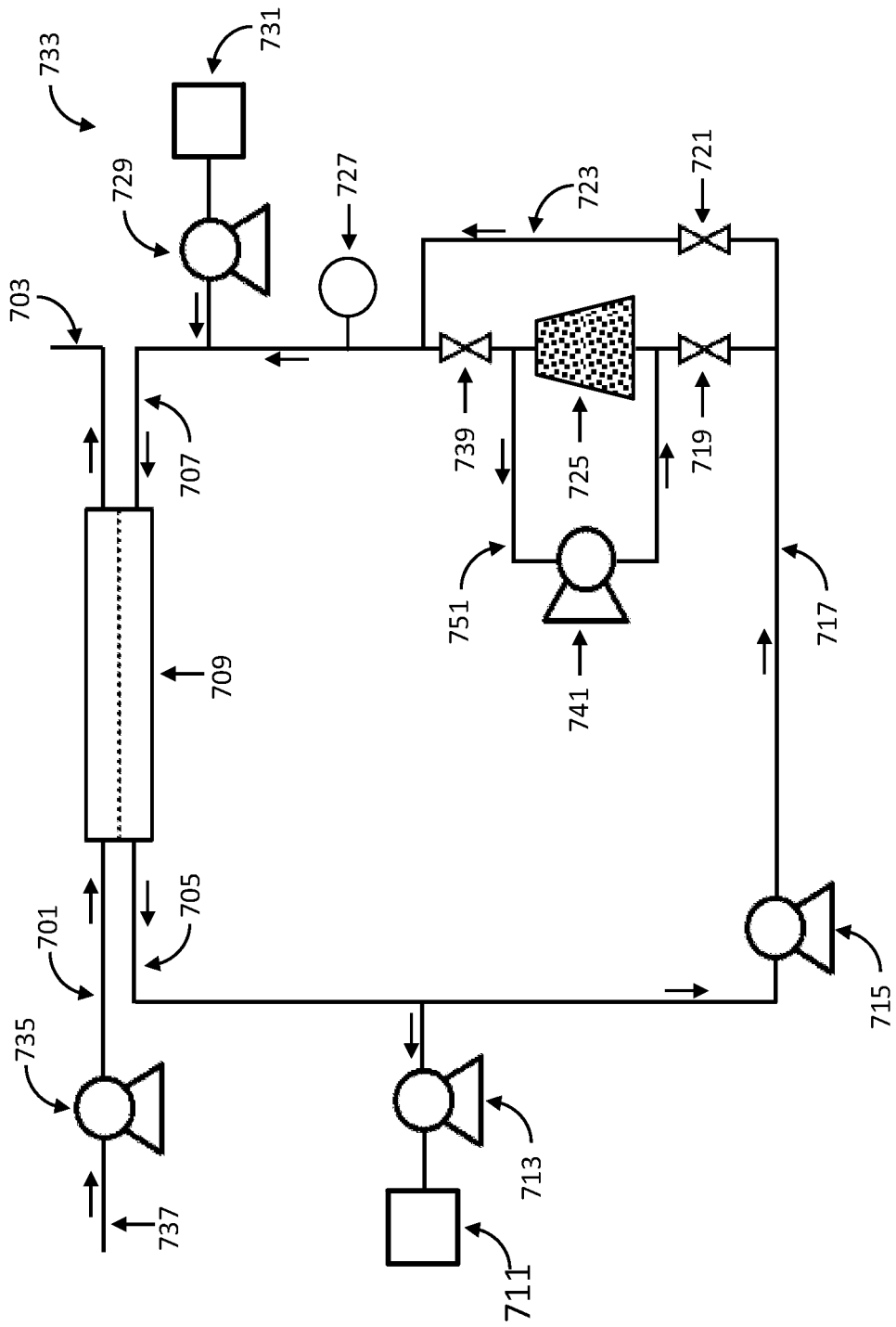
FIG. 17 shows a dialysate regeneration unit having a bypass flow loop and a recirculating flow loop around a sorbent cartridge.

FIG. 17 shows a flow diagram similar to the one in FIG. 16, except it includes a sorbent cartridge recirculation loop 751. The sorbent cartridge recirculation loop 751 includes a recirculating pump 741 that recirculates the dialysate remaining in the sorbent cartridge 725 while the dialysate from the dialysate flow loop 717 is directed through the sorbent cartridge bypass loop 723. The open or closed status of the two-way valves 719, 739 and 721 and operation of recirculating pump 741 determine if dialysate will be recirculated through the sorbent cartridge recirculation loop 751, flow through the sorbent cartridge bypass loop 723 or flow through the sorbent cartridge 725. For example, by closing valves 719 and 739 and opening valve 721 and operating pump 741 the dialysate contained in the sorbent cartridge 725 will be recirculated through the sorbent cartridge recirculation loop 751 and the remaining dialysate in the dialysate flow loop 717 will flow through the sorbent cartridge bypass loop 723. It will be apparent to those skilled in the art that other valve positions and valve types, such as three-way valves, can be utilized to achieve the same outcomes. In certain embodiments, where the sorbent cartridge 725 is configured, as described above, to direct various flow paths to a conductivity sensor in order to measure urea and/or calcium and magnesium concentration, it can be beneficial to recirculate the dialysate remaining in the sorbent cartridge 725 in order to remove certain species still present in the dialysate contained in the sorbent cartridge 725. Removal of any residual species present in the dialysate contained in the sorbent cartridge 725, by recirculation through the sorbent cartridge recirculation loop 751 may improve the accuracy of concentration measurements after dialysate equilibration with the blood has occurred. In certain embodiments the sorbent cartridge 725 can be of a size that can contain several hundred milliliters of dialysate, for example 100 to 1000 milliliters. Therefore, any remaining volume of dialysate contained in the sorbent cartridge 725 will contain a certain concentration of species, for example urea, that has not been removed yet, and this urea, for example, will affect the concentration reading obtained using the sorbent cartridge sensor systems described above after dialysate equilibration has occurred with the blood. Continual recirculation of the dialysate with the sorbent cartridge recirculation loop 751 helps ensure complete removal of any residual species present in the dialysate contained in the sorbent cartridge 725 during equilibration of the dialysate with the blood.

Figure 18:
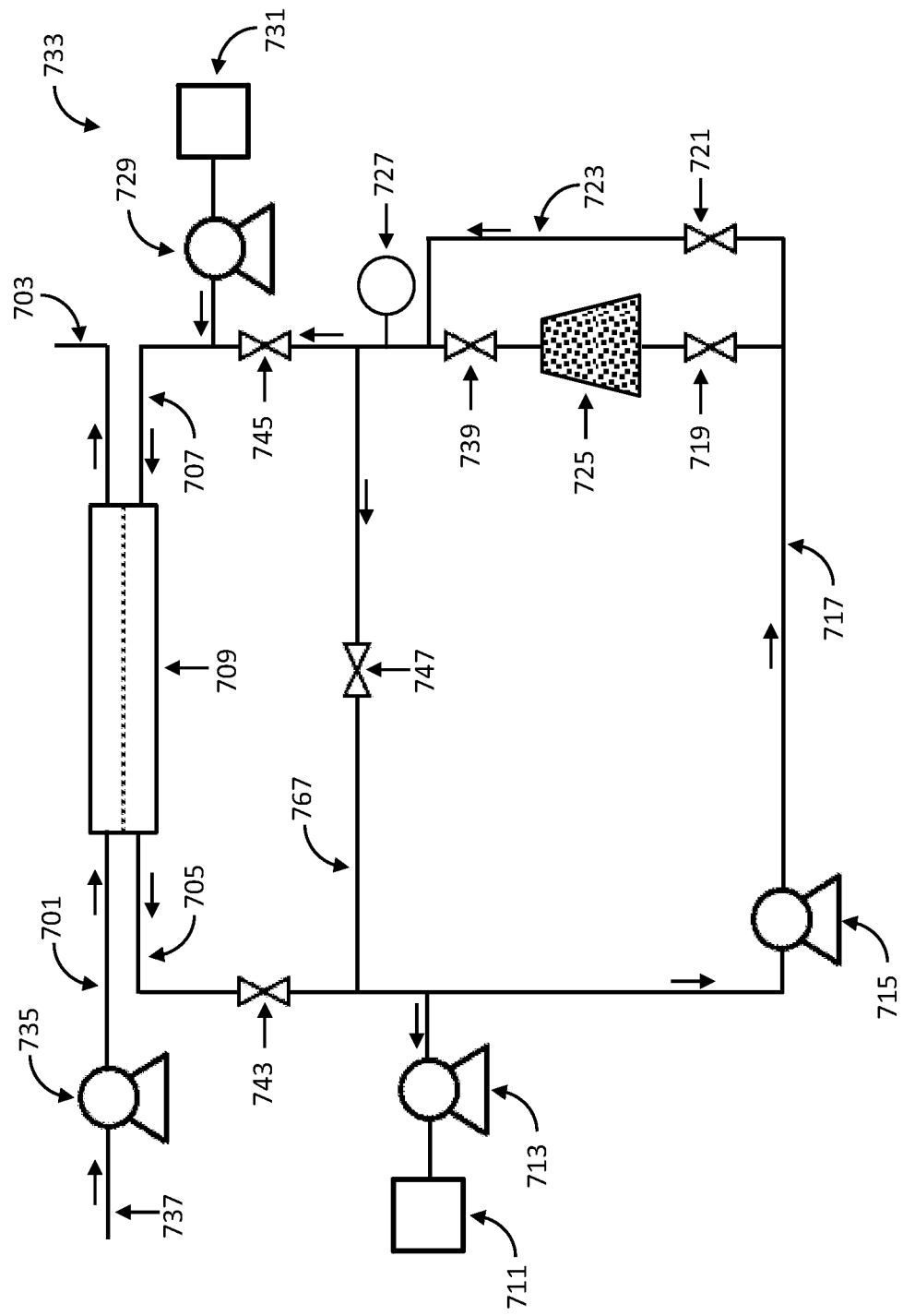
FIG. 18 shows a dialysate regeneration unit having a bypass flow loop around a sorbent cartridge and a bypass flow loop around a dialyzer.

FIG. 18 shows a flow diagram similar to the one shown in FIG. 16, except it includes a dialyzer bypass flow path 767. The dialyzer bypass flow path 767 can be used to circulate dialysate through the sorbent cartridge 725 without having the dialysate pass through the dialyzer 709. Two-way valves 747, 745 and 743 determine where the dialysate will flow. For example, by closing valves 745 and 743 and opening valve 747, the dialysate will flow through the dialyzer bypass flow path 767 and will not flow through the dialyzer 709. It will be apparent to those skilled in the art that other valve positions and valve types, such as three-way valves, can be utilized to achieve the same flow outcomes. Recirculating the dialysate through the sorbent cartridge 725 without passing the dialysate through the dialyzer will completely remove certain species from the dialysate. After the complete removal of certain species from the dialysate, such as urea, the dialysate flow can be directed back through the dialyzer and concentration changes over time of certain species in the dialysate can be measured with sensor system 727 and used to determine the performance of the dialyzer throughout the therapy and/or the decrease in concentration of certain species in the blood throughout the therapy.

Figure 19:
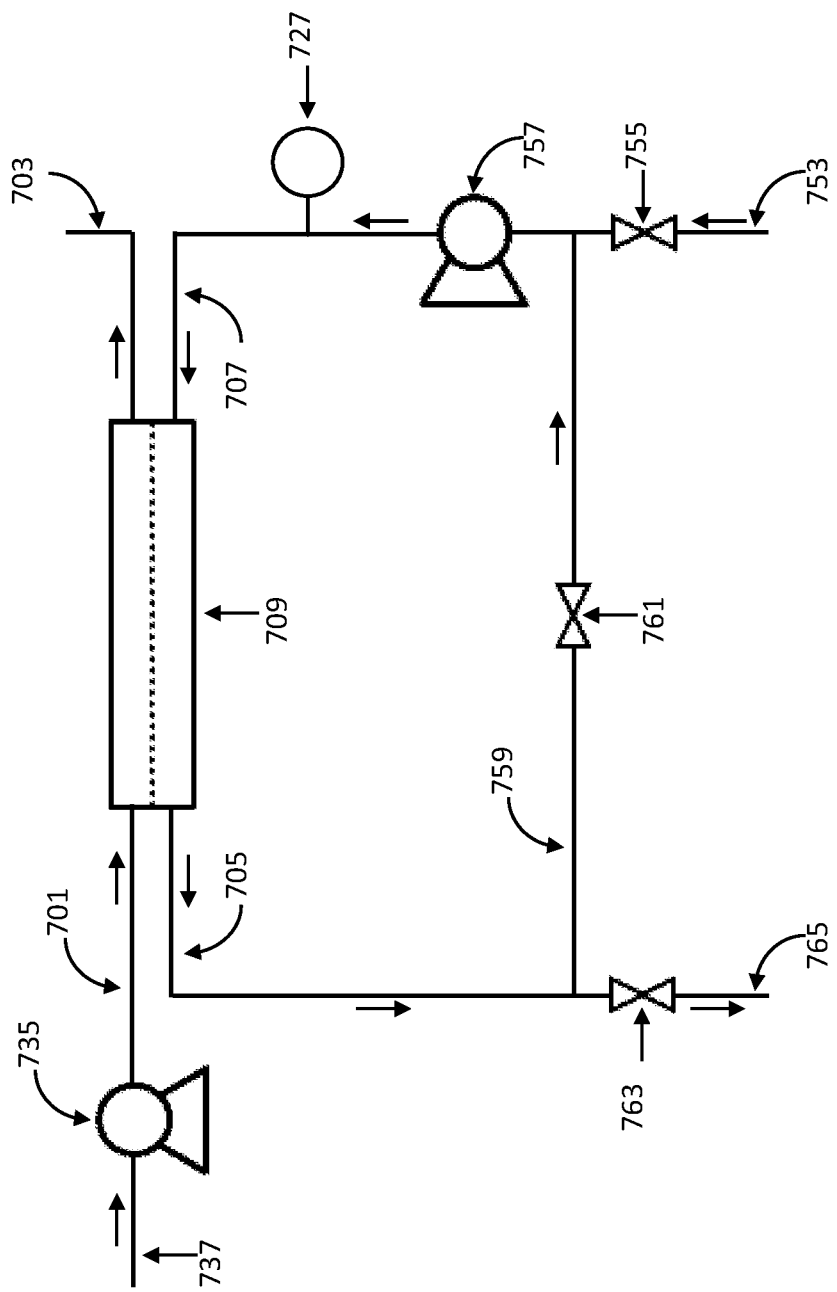
FIG. 19 shows a dialysis flow diagram for a single-pass system with a bypass flow loop around a dialyzer.

FIG. 19 shows a flow diagram for a single-pass hemodialysis system utilizing a bypass flow loop 759 to achieve periodic equilibration between the dialysate and blood. Prepared dialysate enters the system through flow path 753 by operation of dialysate pump 757 and continues to pass sensor system 727. The dialysate continues through the dialyzer 709 as described before for FIG. 16. After exiting the dialyzer 709 through the dialysate outlet flow path 705 the dialysate exits the system through flow path 765. By closing valves 755 and 763 and opening valve 761 the dialysate will be directed through the dialysate recirculation loop 759 and will eventually equilibrate with the blood flowing through the dialyzer 709, thereby allowing the determination of blood concentration levels for certain species by utilization of sensor system 727. The dialysate recirculation loop 759 can be prepared to have a small volume, around 500 milliliters or less to minimize the time required to reach equilibration between the dialysate and blood.

FIGS. 20 through 23 illustrate the effect of various parameters on equilibration time between dialysate and blood. The governing equations used to generate the graphs are derived from a total and differential mass balance on a species between the dialysate and blood. Equation 6 shows the total mass balance for an arbitrary species at any given time during equilibration:

$$V_D \cdot C_D + V_B \cdot C_B = V_B \cdot C_{Bo} \quad \text{[Eq. 6]}$$

where $V_D$ is dialysate volume in liters, $C_D$ is dialysate concentration at time t in mg/dL, $V_B$ is the patient volume for a particular species in liters. For urea $V_B$ would be equal to the urea distribution volume described above. $C_B$ is the blood concentration in mg/dL at time t and $C_{Bo}$ is the blood concentration at a time defined as zero in mg/dL. Equation 7 shows the differential mass balance for the dialysate:

$$V_D \cdot (dC_D/dt) = K(C_B - C_D) \quad \text{[Eq. 7]}$$

where $dC_D/dt$ is the differential change in dialysate concentration with time and K is the dialyzer clearance for an arbitrary species as described above. The use of equations 6 and 7 assumes instantaneous transfer of species between the blood compartment of the body and extra-vascular compartments and assumes the generation of species is negligible and removal of species by means other than dialysis are also negligible. Equations 6 and 7 also assume no filtration is occurring across the dialyzer and that the dialyzer clearance K does not depend on the concentration of blood or dialysate. Equations 6 and 7 can be solved, assuming the initial dialysate concentration is zero to yield the following non-linear equation 8:

$$C_D = C_{Bo}[(1/V_D)/(1/V_B + 1/V_D)][1 - e^{\wedge}[-Kt(1/V_B + 1/V_D)]] \quad \text{[Eq. 8]}$$

Also, the concentration of blood during equilibration can be determined by rearrangement of Eq. 8 and the total mass balance equation 6.

Figure 20:
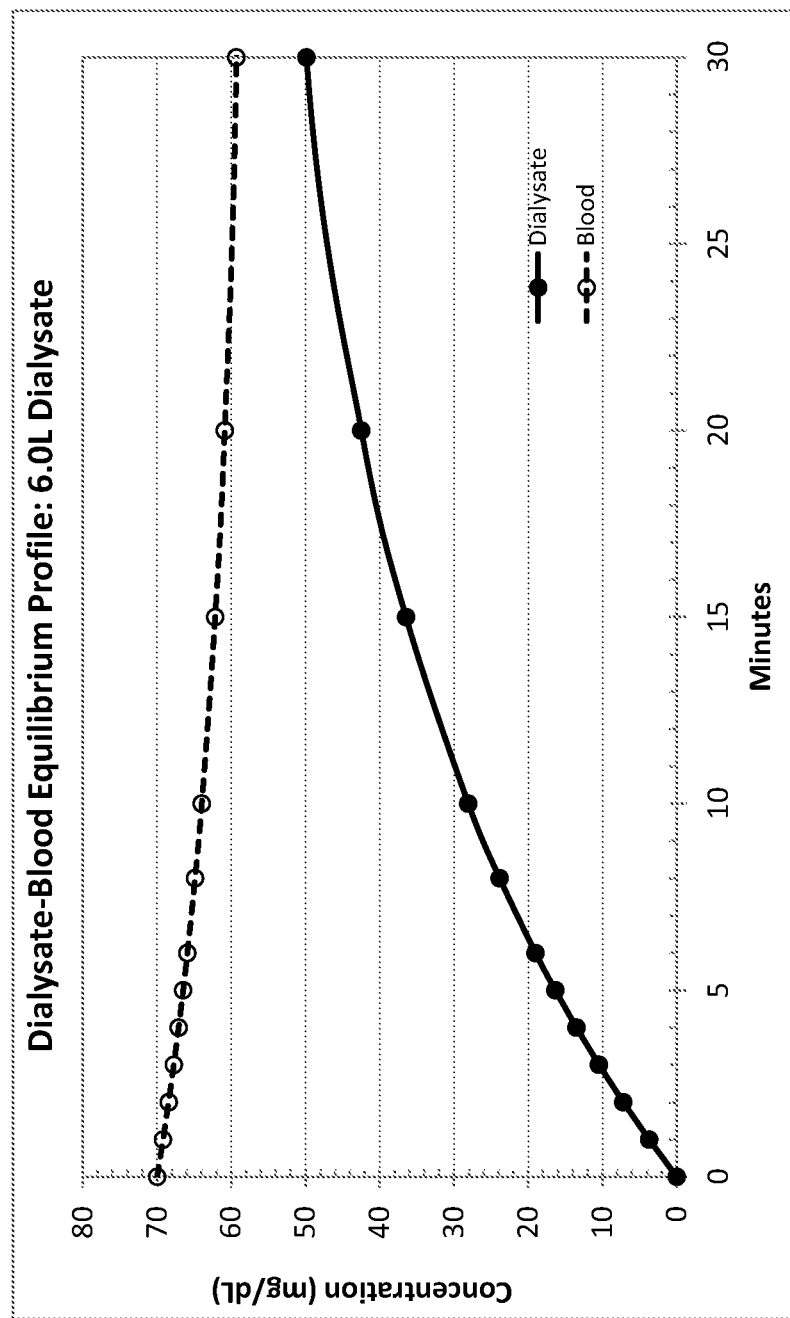
FIG. 20 is a graph showing the effect of a 6 liter dialysate volume on equilibration time between dialysate and blood.
Figure 21:
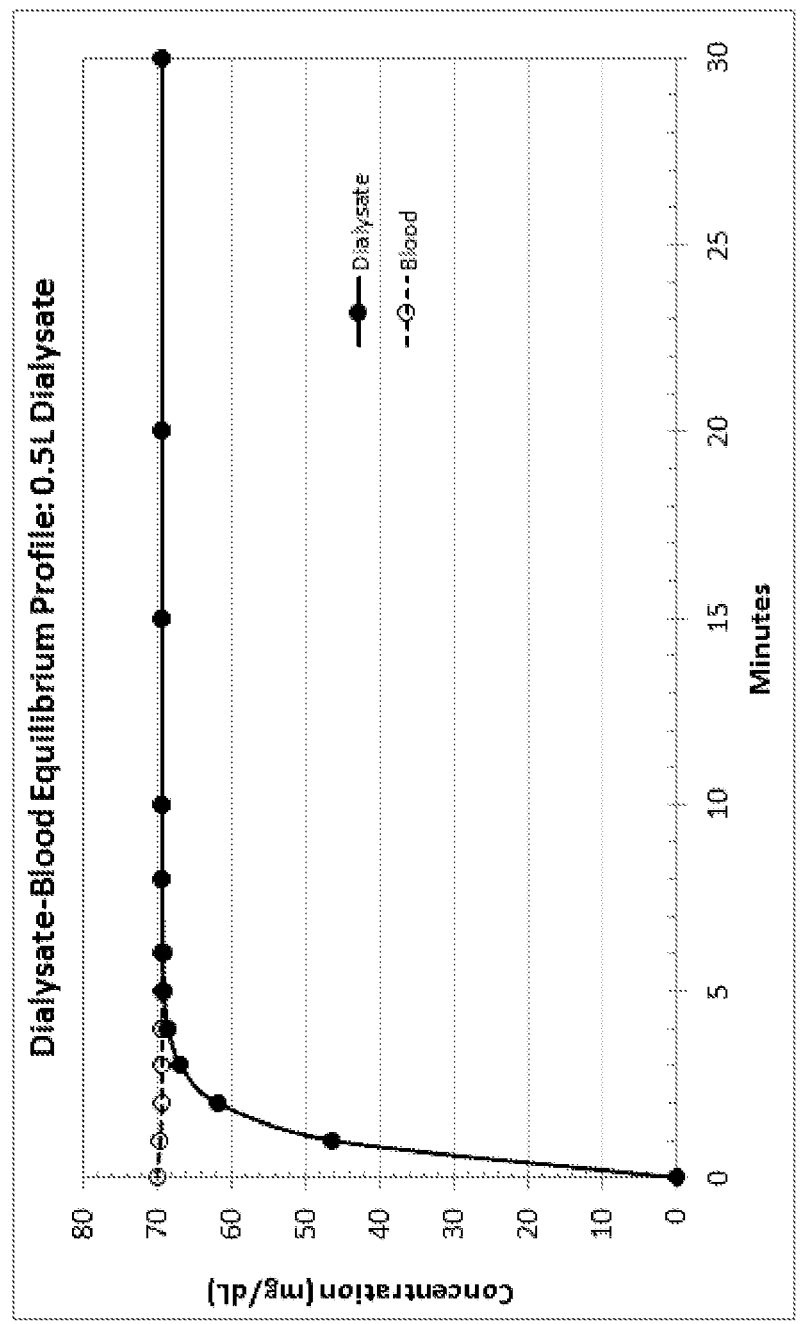
FIG. 21 is a graph showing the effect of a 0.5 liter dialysate volume on equilibration time between dialysate and blood.
Figure 22:
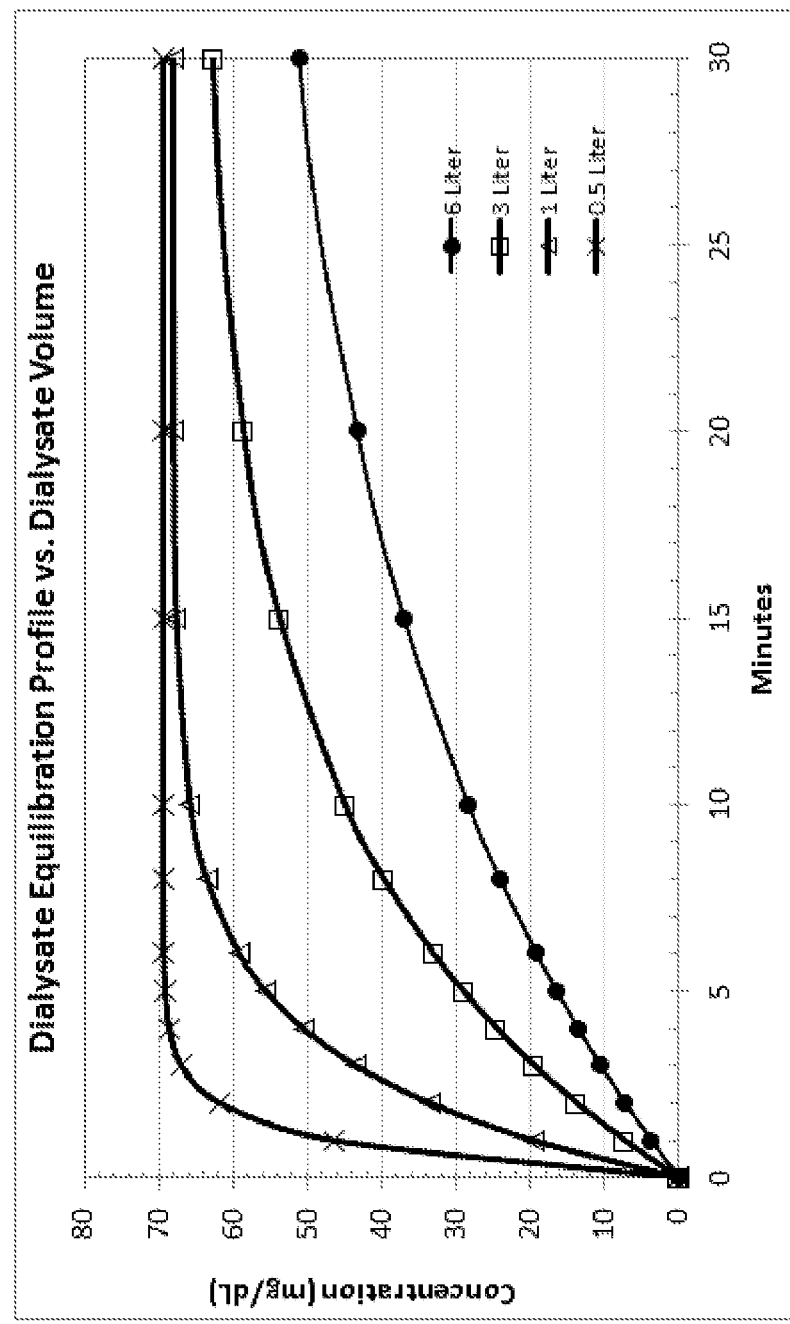
FIG. 22 is a graph showing the effect of various dialysate volumes on the concentration change of dialysate over time during equilibration.

FIG. 20 is generated using the equations described above to illustrate the change in dialysate and blood concentration of urea during equilibration. The results are shown for a 6 liter dialysate volume, a dialyzer clearance of 290 milliliters/minute and a starting blood urea, BUN concentration of 70 mg/dL. The dialyzer clearance of 290 milliliters/minute is used based on a blood flow of 400 ml/min and a dialysate flow of 400 milliliters/minute and a dialyzer size of 1.5 meters squared. Likewise, FIG. 21 shows the change in dialysate concentration and blood over time for urea during equilibrium with the same conditions as for FIG. 20, except with a dialysate volume of 0.5 liters. The time to reach equilibration between blood and dialysate with 6 liters of dialysate takes over 30 minutes compared to less than 5 minutes if the dialysate volume is 0.5 liters, illustrating the significant advantage to having a small dialysate volume in terms of minimizing equilibration time. FIGS. 20 and 21 also show the blood concentration of urea over time during equilibration. As shown in FIG. 21 the blood concentration does not change by a significant amount during equilibration resulting in an accurate determination of the actual blood concentration. However, FIG. 20 shows a significant decline in blood concentration during equilibration, which will result in an inaccurate determination of blood concentration at the time point of interest. FIG. 22 also illustrates the effect of dialysate volume on the change in dialysate concentration of urea over time during equilibration with blood. The data shown in FIG. 22 is generated under the same conditions as the data in FIGS. 20 and 21, except dialysate volumes of 1 liter and 3 liters are also shown. FIG. 22 also illustrates the significant effect dialysate volume has on equilibration time, even at volumes as low as 1 liter. Therefore, there is significant advantage to having a dialysate flow path with a small volume of 0.5 liters or less, as described in various embodiments of the invention.

Figure 23:
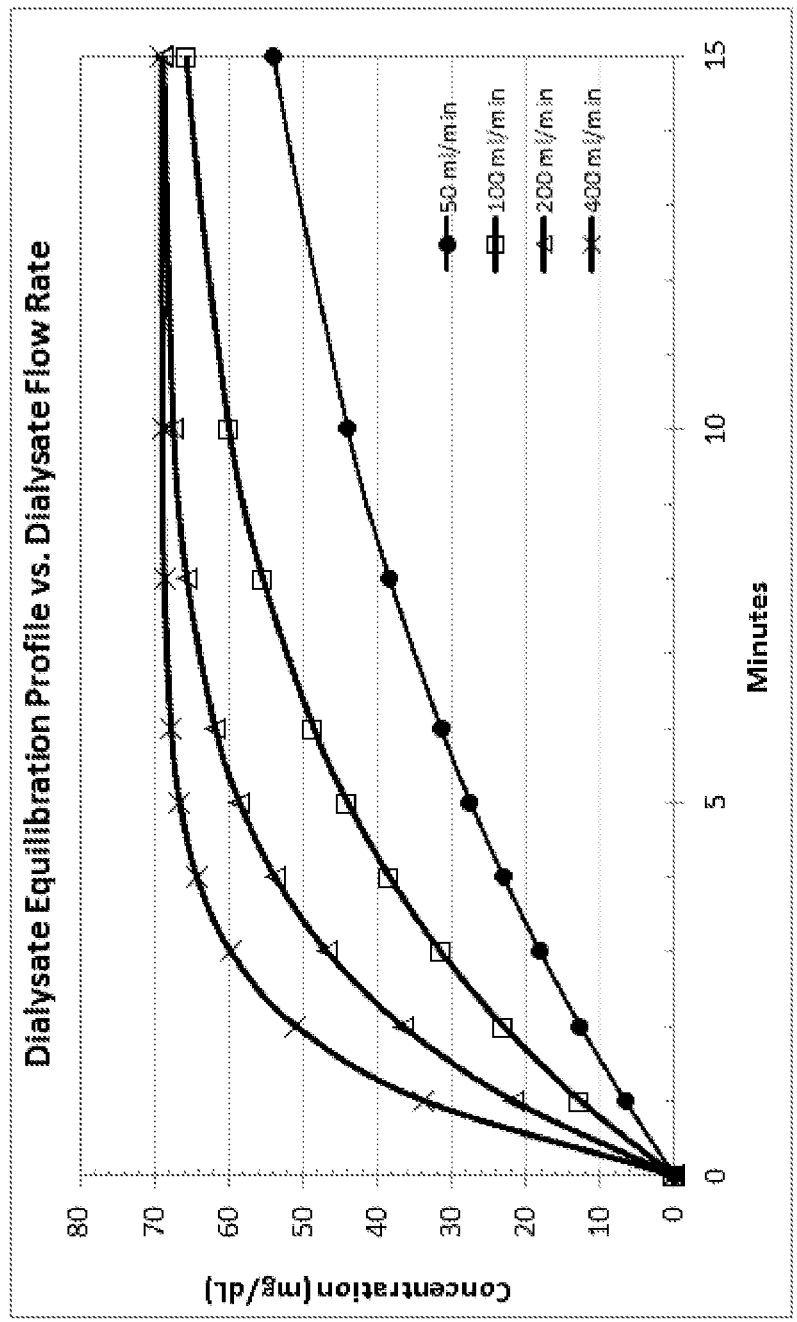
FIG. 23 is a graph showing the effect of dialysate flow rate on equilibration time between dialysate and blood.

FIG. 23 shows the effect of dialysate flow rate on the change in dialysate concentration over time during equilibration with blood. The data is generated assuming a starting blood urea BUN concentration of 70 mg/dL, a blood flow rate of 400 ml/min, a 1.5 meter square dialyzer and a dialysate volume of 0.5 liters. The dialyzer clearance at dialysate flow rates of 50, 100, 200 and 400 ml/min are assumed to be 50, 100, 190 and 290 ml/min, respectively. FIG. 23 illustrates the significant effect dialysate flow rate has on equilibration time. For example, a dialysate flow rate of 100 ml/min requires 15 minutes for equilibration, compared to only 5 minutes required for a dialysate flow rate of 400 ml/min. Therefore, increasing the dialysate flow rate during equilibration will reduce the time to reach equilibrium. For example, if a dialysis therapy requires a dialysate flow rate of 100 ml/min, due to capacity and flow limitations of the sorbent cartridge, during equilibration the dialysate flow rate can be increased above 100 ml/min without affecting the sorbent cartridge because the dialysate flow will not flow through the sorbent cartridge. Likewise, the blood flow can also be increased during equilibration, which will increase the dialyzer clearance, K, and thereby decrease the equilibration time. In some cases it may beneficial to increase the blood and dialysate flow, in order to minimize the equilibration time.

The filtration rate across the dialyzer will also decrease the time to reach equilibration. Therefore, continuing to perform ultrafiltration on the patient during the equilibration period will help decrease the equilibration time. In FIGS. 16, 17 and 18 the control pump 713 can be used to provide ultrafiltration across the dialyzer. In certain embodiments the ultrafiltration rate can be increased during equilibration to achieve a further reduction in equilibration time.

Another feature of the systems described for FIGS. 16, 17 and 18, is the use of a conductivity sensor as part of the sensor system 727. A conductivity sensor can be used in several ways. First, the conductivity of the dialysate can be monitored during equilibration to determine when equilibration is reached. In general the conductivity of the dialysate is a measure of the sodium concentration because it is the major conductive species present. If the blood sodium concentration differs from the dialysate sodium concentration, the conductivity of the dialysate can be monitored until a plateau is reached, which would indicate that the sodium concentration of the blood has equilibrated with the sodium concentration of the dialysate. Because sodium and urea occupy approximately the same volume in a patient and transfer across the dialyzer at similar rates, equilibration of sodium will also indicate equilibration with urea. The same is also true for calcium, magnesium, potassium and chloride with respect to sodium and urea. In certain cases the dialysate sodium concentration and blood sodium concentration will be close to the same value, which would lead to a negligible change in dialysate conductivity during equilibration. In such cases the dialysate sodium concentration can be temporarily increased by adding a sodium bolus to the dialysate with the reconstitution system 733 described above for FIGS. 16, 17 and 18. Likewise the reconstitution system 733 can also temporarily decrease the sodium concentration of the dialysate by adding water to dilute the dialysate. The temporary change in sodium concentration of the dialysate will result in a sodium concentration difference between the blood and dialysate and ultimately a conductivity difference that can be monitored during equilibration to determine when equilibration is complete.

Another advantage of the equilibration method is the ability to determine a patient's pre-dialysis blood sodium concentration. In some cases it is beneficial to the patient if their blood sodium concentration before and after a dialysis session remains the same, which can result in less fluid gain between dialysis sessions. By utilizing the equilibration method at the start of a dialysis session, a patient's initial blood conductivity can be determined. However, as shown, accurate determination of the patient's blood conductivity requires minimization of the equilibration time between the blood and dialysate, which can be achieved utilizing several of the methods described for certain embodiments including low volume dialysate, increased dialysate and blood flow rates, and continuation of ultrafiltration during the equilibration. As stated before the conductivity of the blood and dialysate is approximately equal to the sodium concentration of the blood and dialysate. Therefore, the conductivity of the blood at the start and end of a dialysis session can be determined using the equilibration techniques described. The therapy can then be adjusted by changing the delivery of solutions with the reconstitution system 733 in order to ensure the blood conductivity at the end of the session matches the conductivity at the beginning of the session, as determined with the equilibration method. The sensor system 727 can also include a sodium sensor for measuring sodium directly, such as an ion-selective electrode for sodium. The patient's initial pre-dialysis sodium concentration, pH, conductivity values, ammonium ion or urea concentrations, can also be used to set target values for any one of conductivity, pH, sodium concentration, ammonium ion, or urea values for the dialysate to be used during the dialysis session. In some cases the dialysate conductivity can be controlled with a closed-loop system between the conductivity sensor and the reconstitution system 733. Sensor types, such as ion-selective electrodes and pH can be used in a similar manner as described herein for closed-loop control and to make measurements by calculating a difference based on any one of pH, sodium and urea concentrations, and ammonium ion concentrations.

Figure 24:
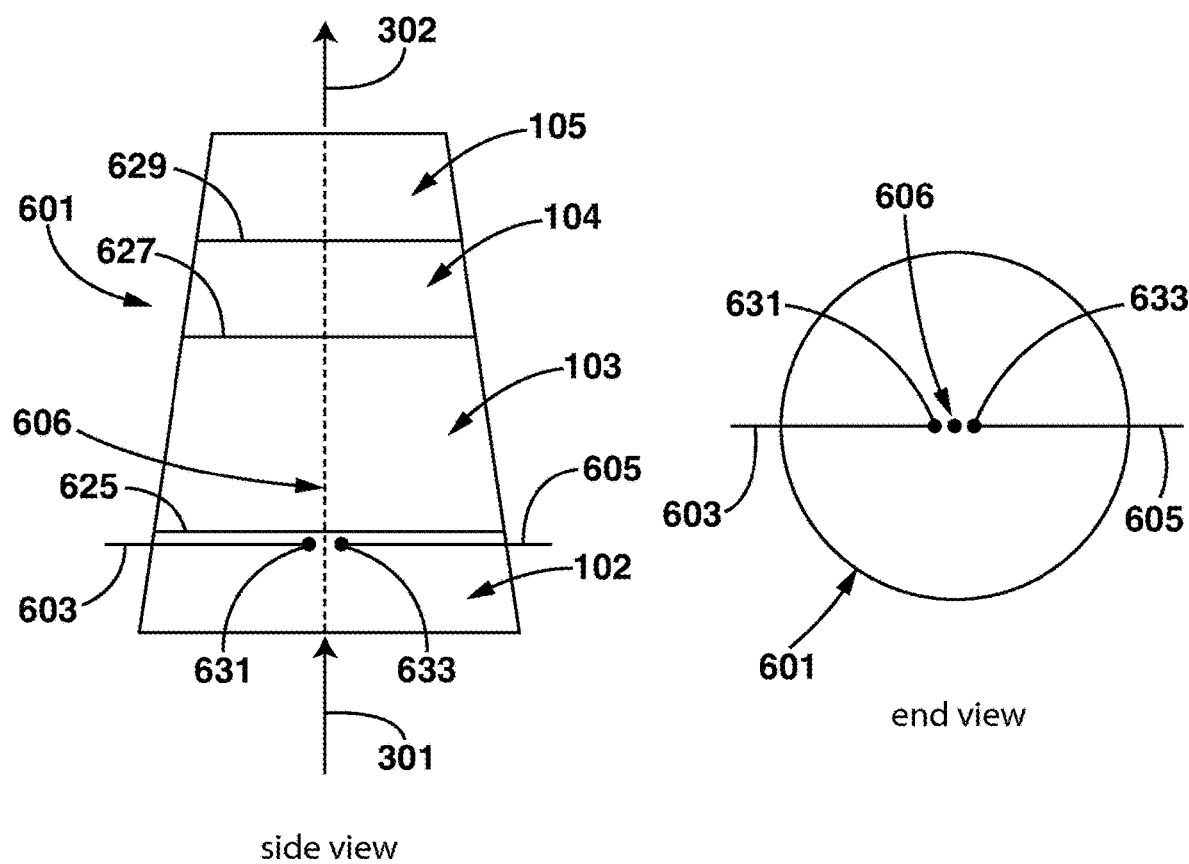
FIG. 24 shows a sorbent cartridge with built in electrodes for measuring conductivity perpendicular to the central axis.

FIG. 24 shows a diagram for a sorbent cartridge design that includes built-in conductivity electrodes 603 and 605. The sorbent cartridge 601 is similar to sorbent cartridge 100 described for FIG. 1, except for the addition of conductivity electrodes 603 and 605. Dialysate enters the sorbent cartridge 601 through the inlet flow path 301 and exits through the outlet flow path 302 after passing through multiple sorbent material layers 102, 103, 104, and 105 as described for FIG. 1. However, the number of sorbent materials contained in the sorbent cartridge can be varied and the position of the sorbent materials can be changed. As shown in FIG. 24 the sorbent materials are in discrete layers separated by interfaces 625, 627 and 629. The interface 625 represents where the first sorbent material 102 ends and the second sorbent material 103 begins. Likewise, interface 627 represents where the second sorbent material 103 ends and the third sorbent material 104 begins. Also, interface 629 represents where the third sorbent material 104 ends and the fourth sorbent material 105 begins. Four or more sorbent layers and the required number of interface layers are contemplated by the present invention. A central axis 606 is shown which represents a straight line, parallel to the direction of flow through the sorbent cartridge 601, to which the sorbent cartridge 601 is symmetrical. The electrode pair, 603 and 605, include one conductivity sensor that is built into the sorbent cartridge 601. The electrodes 603 and 605 can be fastened through the wall of the sorbent cartridge 601. Various means for fastening the electrodes 603 and 605 can be envisioned and are well known to those of skill in the art. Non-limiting examples of fastening methods may include welding and adhesive bonding, and mechanical fixation among others. The electrodes may also be fastened at each end of the sorbent cartridge as opposed to the sides, which is the configuration shown in FIG. 24. The electrodes 603 and 605 have an active electrode head 631 and 633, respectively. An electrical conductivity measurement occurs when a potential is applied across the electrode heads 631 and 633 and the current is measured. The conductivity can then be calculated with Ohm's law (V=IR), where V is the applied potential, I is the measured current and R is the resistivity, which is equal to the inverse of the conductivity. The electrode heads 631 and 633 can be made from various materials known to those with skill in the art including, but not limited to platinum, platinum-iridium, titanium, gold-plated nickel, and graphite and can be positioned at any varying radii from the central axis 606. For example, electrode heads 631 and 633 can be positioned near or at a perimeter, periphery or circumference of a sorbent layer, or near or on the central axis 606. In embodiments where the sorbent layer has a circumference as measured from the central axis 606, the electrode heads can be positioned at any one of 7r/8, 3r/4, r/2, r/3, r/4, r/5, r/8, r/16, r/32, and r/64 where r is the radius measured from the central axis 606.

The portion of the electrodes 603 and 605 leading out of the sorbent cartridge 601 can be made from the same material as the electrode head, or other conductive materials and can serve to both stabilize the electrode heads 631 and 633 within the sorbent cartridge 601 and provide a path to apply the potential and measure the current across the electrode heads 631 and 633. The potential can be applied by various sources and methods well known to those of skill in the art, including with an external power supply. The resulting current can be measured by various ways well known to those of skill in the art, including with an ammeter. It is also possible to determine the conductivity by applying a current across the electrode heads 631 and 633 and measuring the resulting potential.

The electrode heads 631 and 633 shown in FIG. 24 can be placed in various positions within the sorbent cartridge 601. As shown in FIG. 24 both electrode heads 631 and 633 are positioned close to the central axis 606 as shown in the side-view and end-view of FIG. 24. The electrode heads as positioned in FIG. 24, will measure conductivity across a distance perpendicular to the central axis 606. The electrode heads 631 and 633 are also located in sorbent material 102 near interface 625. However, other positions for the electrode heads 631 and 633 are considered. For example, the electrode heads 631 and 633 can be placed in any sorbent material layer and at any distance away from the interface. Also, the electrode heads 631 and 633 can be located any position from the central axis. The distance between the electrode heads 631 and 633 can also be varied. In some cases it is beneficial to have a minimum distance between the electrode heads 631 and 633 in order to avoid local conductivity measurements that may be high or low, compared to other locations within the sorbent cartridge. In certain embodiments, the electrode heads 631 and 633 are positioned in the same sorbent material layer. Finally, multiple electrodes may be placed throughout the sorbent cartridge 601 in order to measure multiple conductivities at multiple positions within the sorbent cartridge 601. In the case of multiple electrodes present in the sorbent cartridge 601 a multiplexer can be used.

Figure 25:
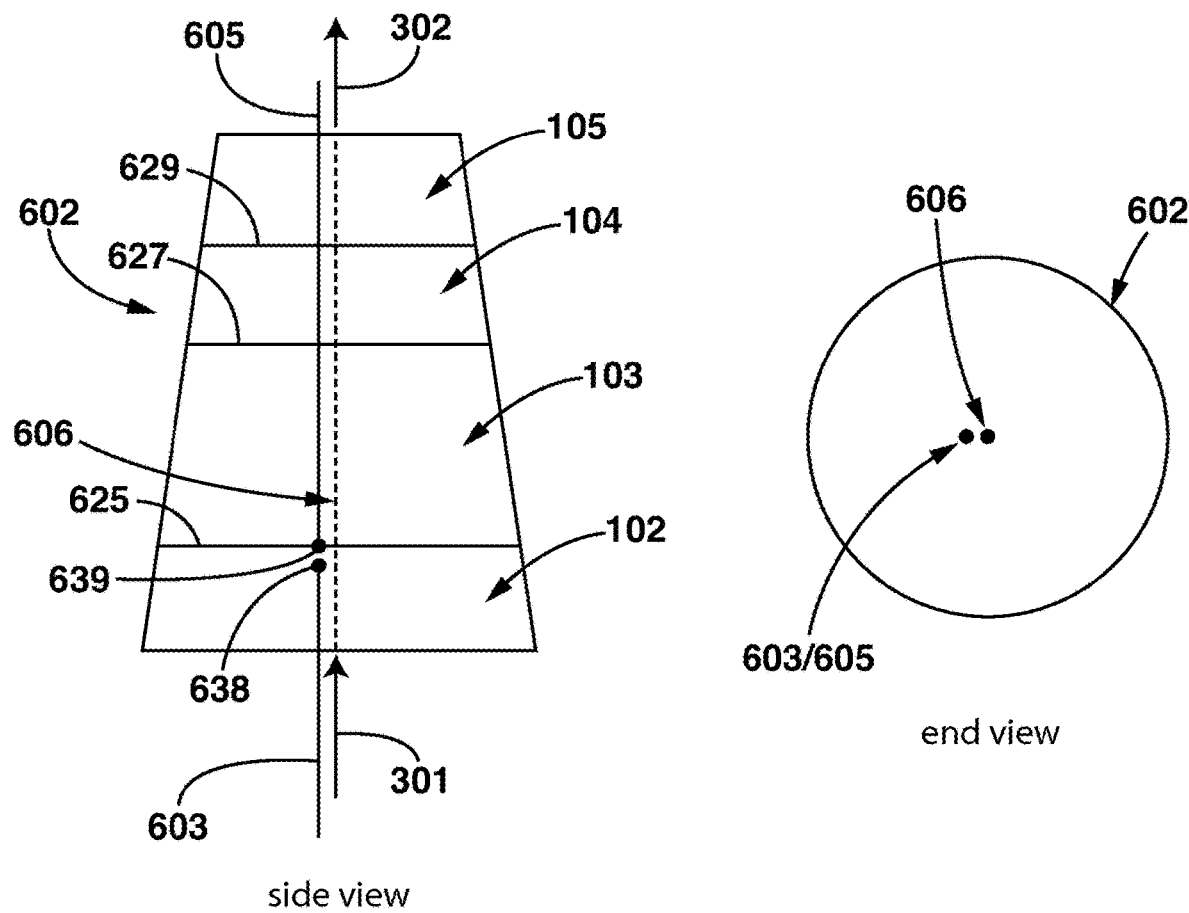
FIG. 25 shows a sorbent cartridge with built in electrodes for measuring conductivity parallel to the central axis.

FIG. 25 shows a sorbent cartridge 601 with electrodes 603 and 605 similar to the ones shown in FIG. 24, except the electrode heads 631 and 633 are positioned to measure conductivity across a distance parallel to the central axis 606. The electrode heads 631 and 633 can also be placed in the various positions described above with reference to FIG. 24, for example, at different material layers in the sorbent cartridge The positioning of the electrode heads 640 and 641 farther apart allows the conductivity to be measured across a distance parallel to the direction of flow through the sorbent cartridge and can be used to determine changes in capacity of a particular sorbent material and cumulative removal of species from the dialysate.

Figure 26:
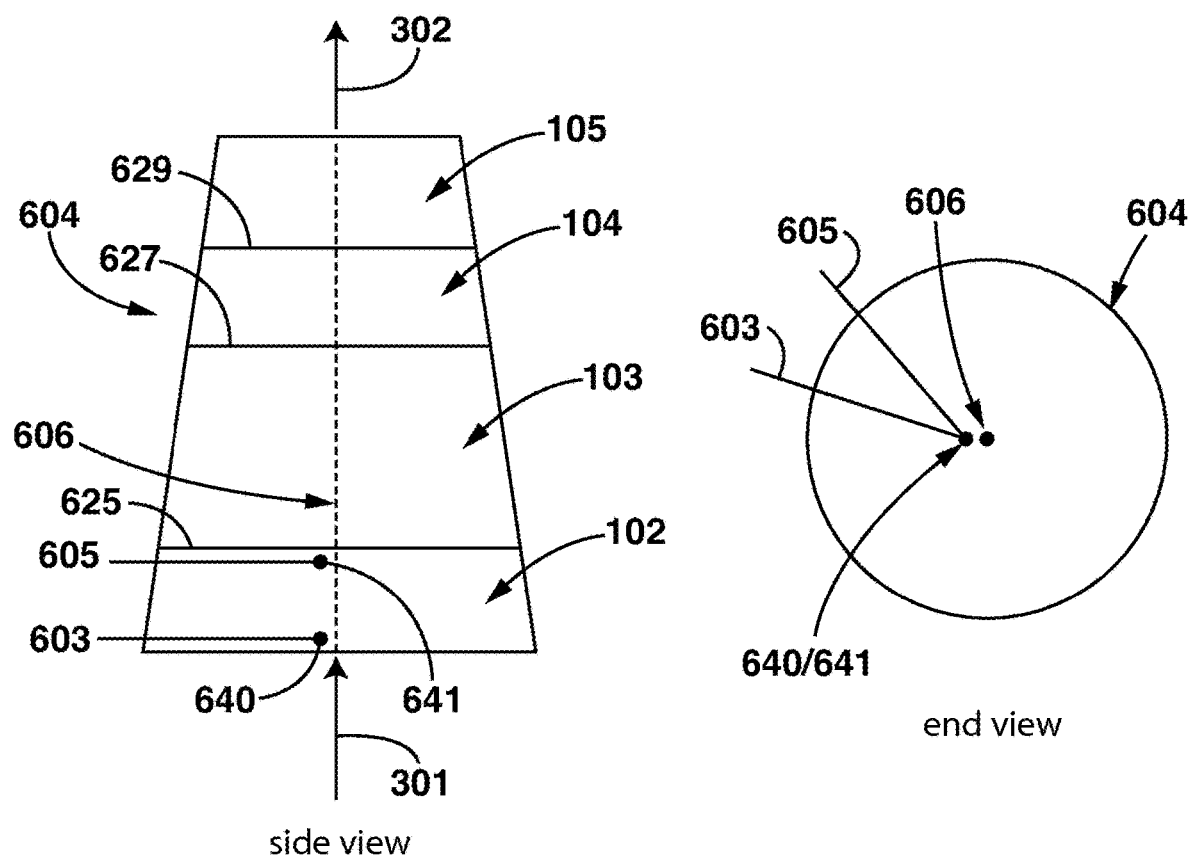
FIG. 26 shows a sorbent cartridge with built in electrodes for measuring conductivity parallel to the central axis over a distance spanning a sorbent material layer.

FIG. 26 is similar to FIG. 25 except the distance between the electrode heads 640 and 641 is farther apart. The electrode heads 640 and 641 can also be placed in the various positions described above with reference to FIG. 24.

Figure 27:
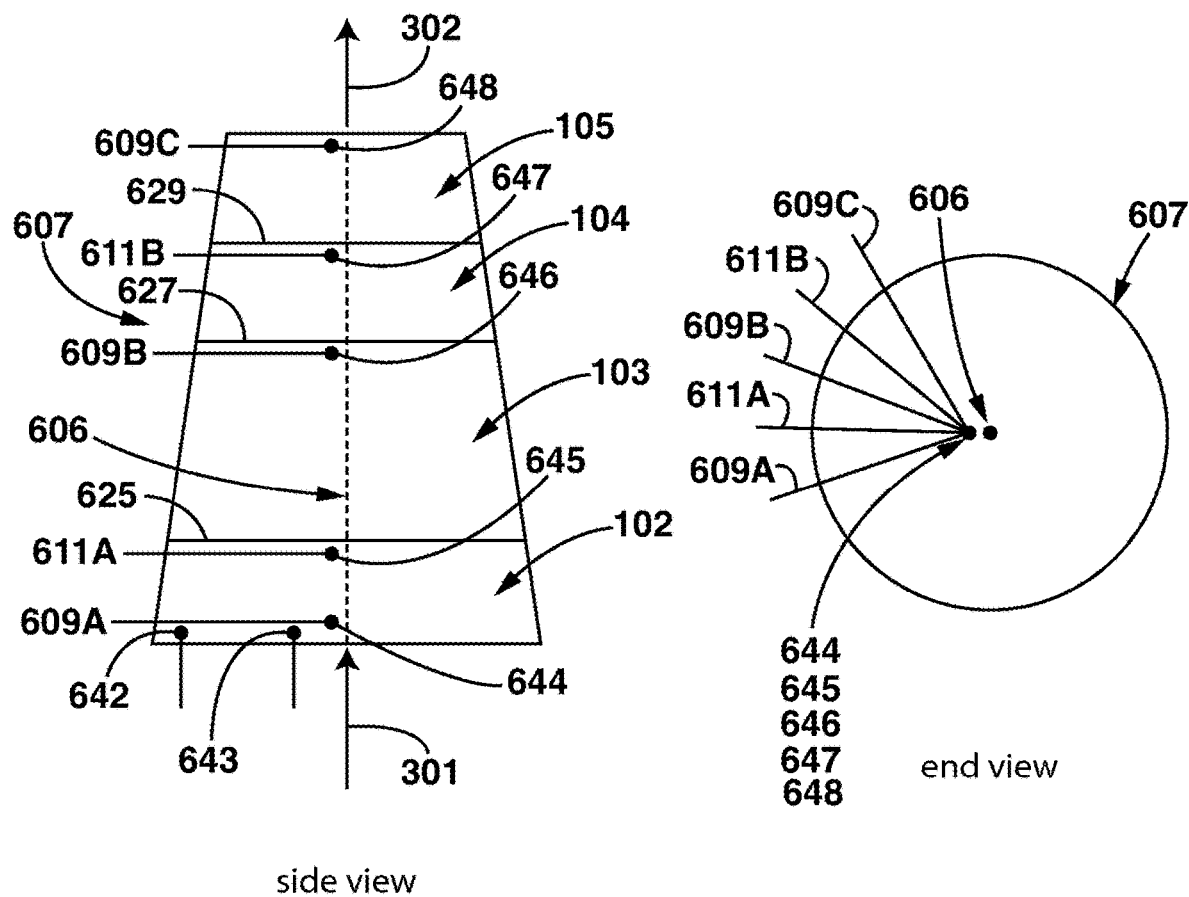
FIG. 27 shows a sorbent cartridge with built in electrodes for measuring conductivity parallel to the central axis over a distance spanning multiple sorbent material layers.

FIG. 27 is similar to FIG. 26, except several electrodes 609A, 609B, 609C, 611A and 611B are shown. This configuration allows multiple electrode pairs to be selected resulting in multiple conductivity measurements. For example, a potential can be applied across electrodes 609A and 609B and the conductivity measured or a potential can be applied across electrodes 609A and 611A. Other combination of electrodes can be envisioned to gather specific measurements as may be required between the various material layers in the sorbent.

Figure 28:
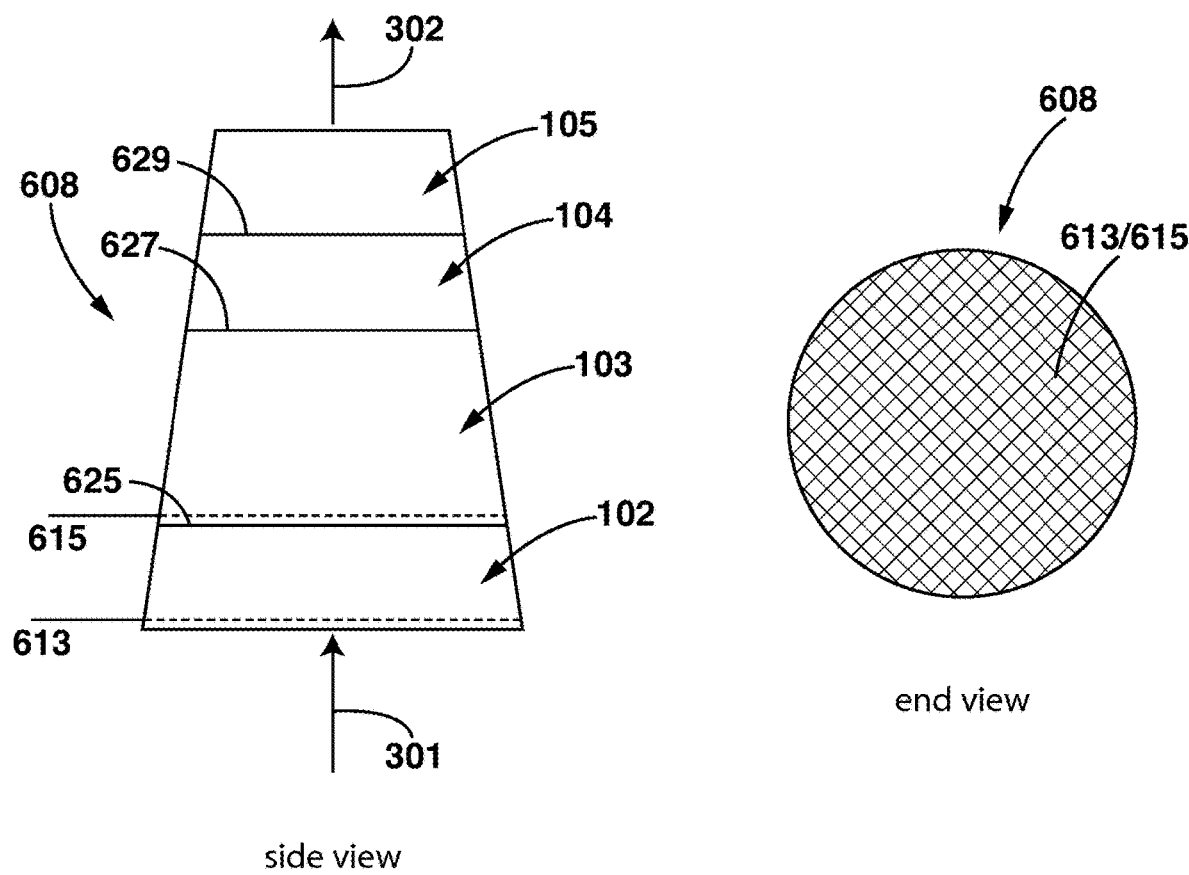
FIG. 28 shows a sorbent cartridge with built in mesh electrodes for measuring conductivity parallel to the central axis over a distance spanning multiple sorbent materials.

FIG. 28 is similar to FIG. 27, except the electrodes are made out of mesh and function to not only measure conductivity as described for FIG. 27, but also function to provide flow redistribution as dialysate flows through the sorbent cartridge 608 and provide separation between the sorbent layers. The mesh electrodes can have a mesh size of 1 to 100 microns and the mesh opening can be configured in various geometries, such as squares (as shown in FIG. 28 side-view), circles or rectangles (not shown).

Figure 29:
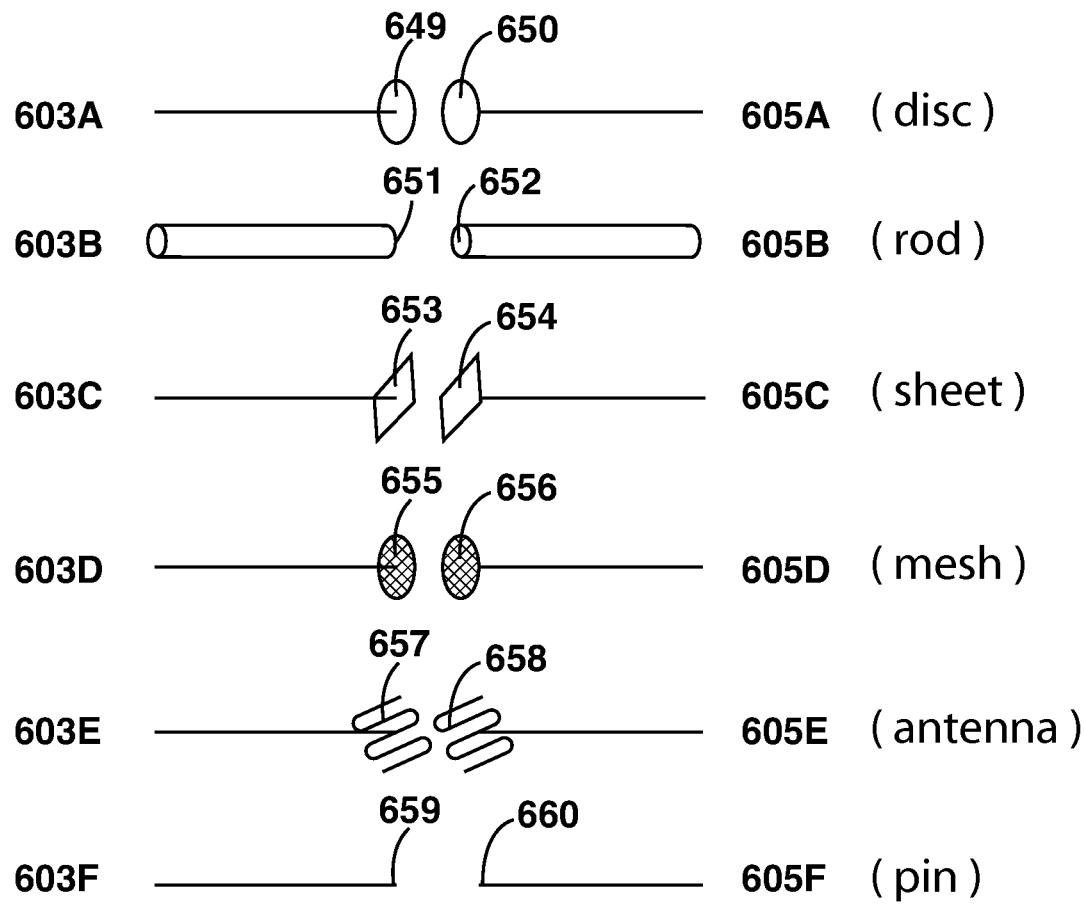
FIG. 29 shows different electrode designs.

FIG. 29 shows different electrode designs that can be used in embodiments described above with reference to FIGS. 24, 25, 26 and 27. It will be obvious to those skilled in the art that other electrode designs can be used. Disc electrodes 603A and 605A have an electrode head 649 and 650 in the shape of a disc. Rod electrodes 603B and 605B refer to electrodes in the shape of a rod or cylinder, with one end functioning as an electrode head 651 and 652. Sheet electrodes 603C and 605C refer to an electrode with an electrode head 653 and 654 in the shape of a sheet. The sheets can be square, rectangular, circular or other solid planar geometries. The mesh electrodes 603D and 605D refer to an electrode with an electrode head 655 and 656 consisting of a mesh, where a mesh is the same as that described for a mesh electrode. Antenna electrodes 603E and 605E refer to an electrode with an electrode head 657 and 658 in the shape of an antenna, where the antenna shape refers to a serpentine structure of conductive wires or strips. Pin electrodes 603F and 605F refer to a rod electrode with a small diameter and an electrode head 659 and 660. Other electrodes and electrode head geometries known within the art are contemplated and can be used in the present invention.

Figure 30:
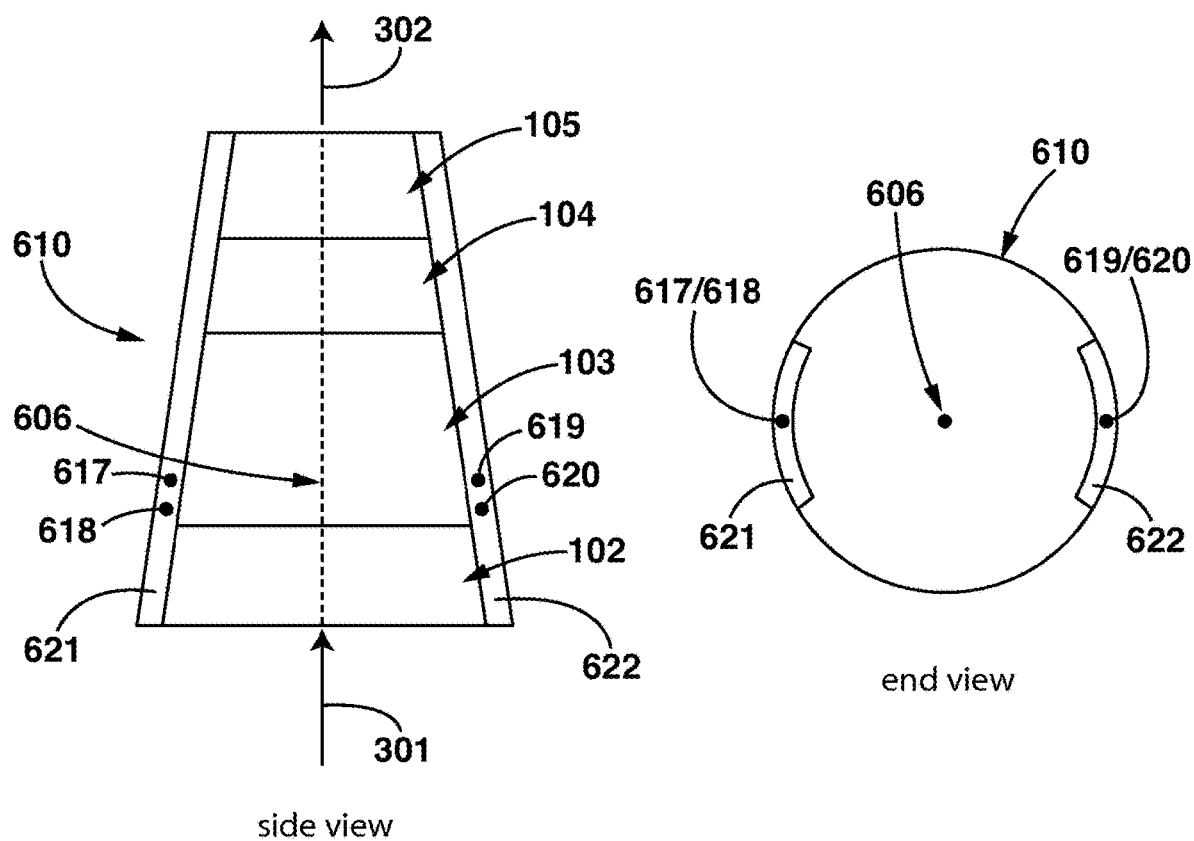
FIG. 30 shows a sorbent cartridge with electrodes built into the wall of the sorbent cartridge for measuring conductivity.

FIG. 30 shows a sorbent cartridge 610 with electrode strips 621 and 622 built into the wall of the sorbent cartridge 610. The electrode strips 621 and 622 contain active electrode areas 617, 618, 619 and 620 that can be used in various pair configurations to measure conductivity. The electrode strips 621 and 622 can be built into the wall of the sorbent cartridge by bonding, welding or other methods well known to those of skill in the art. The electrode strips can also include flex circuits. The sorbent cartridge could also contain a single electrode strip that wraps around the whole perimeter of the sorbent cartridge wall. The use of electrode strips built into the wall of a sorbent cartridge simplifies the construction and incorporation of electrodes into a sorbent cartridge. The electrode strips can be connected external to the sorbent cartridge in order to apply a potential and measure current across active electrode areas.

The FIGS. and specific examples provided herein illustrate a possible embodiment of the invention and are non-limiting with respect to the specific physical geometries of the various components depicted in the illustrations. It will be apparent to one skilled in the art that various combinations and/or modifications can be made in the systems and methods described herein depending upon the specific needs for operation. Moreover, features illustrated or described as being part of one embodiment may be used on another embodiment to yield a still further embodiment.

The invention claimed is:

1. A method for determining an effective clearance of a dialyzer, comprising:
   measuring a first conductivity value of a dialysate flowing from an outlet of the dialyzer not having contacted a urease containing material layer of a sorbent regeneration system;

measuring a second conductivity value of the dialysate flowing from the outlet of the dialyzer after the dialysate has contacted the urease containing material layer of the sorbent regeneration system;

intermittently providing an electrolyte bolus or diluent to a dialysate flow path and measuring a bolus conductivity of the dialysate passing to the dialyzer to provide a third conductivity value;

measuring a bolus conductivity of the dialysate passing from the dialyzer to provide a fourth conductivity value;

measuring a dialysate flow rate; and determining the effective clearance of the dialyzer from the third and fourth conductivity values.

2. The method of claim 1, further comprising:
determining a BUN (blood urea nitrogen) and/or a blood concentration of a solute from the effective clearance of the dialyzer from the first and second conductivity values.

3. The method of claim 1, further comprising the step of determining a urea content of the dialysate flowing from the dialyzer based at least in part on a difference in conductivity between the first and second conductivity values.

4. The method of claim 1, wherein the dialysate contacts a plurality of materials of the sorbent regeneration system in a sequential order; wherein the plurality of materials are contained in one or more sorbent cartridges, and wherein at least one material includes an ion exchange resin selective for calcium ions and magnesium ions and releasing hydrogen ions in exchange.

5. The method of claim 1, further comprising:
determining a third conductivity value of the equilibrated dialysate that has contacted an additional material layer other than the material layer(s) contacted by the dialysate of the first or second conductivity value; and determining a blood solute concentration of at least a second blood solute from either the second and third conductivity values or the first and third conductivity values.

6. The method of claim 1, further comprising calculating one or more of the selected measures: URR (urea reduction ratio), Kt/V, eKt/V (equilibrated Kt/V), and PCR (protein catabolic rate), wherein K stands for dialyzer clearance rate, t stands for dialysis time, and V stands for volume of distribution of urea; and wherein Kt/V, eKt/V and PCR are each determined based on a difference between the first and second conductivity values; and wherein URR is determined by calculating a first BUN (blood urea nitrogen) prior to dialysis and a second BUN (blood urea nitrogen) post dialysis.

* * * * *